US007192916B2

(12) United States Patent
Jessell et al.

(10) Patent No.: US 7,192,916 B2
(45) Date of Patent: Mar. 20, 2007

(54) GENE ENCODING MNR2 AND USES THEREOF

(75) Inventors: Thomas M. Jessell, New York, NY (US); Yasuto Tanabe, Kyoto (JP); Christopher William, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 351 days.

(21) Appl. No.: 09/820,598

(22) Filed: Mar. 29, 2001

(65) Prior Publication Data
US 2003/0104374 A1 Jun. 5, 2003

Related U.S. Application Data

(63) Continuation of application No. PCT/US99/22517, filed on Sep. 29, 1999, which is a continuation-in-part of application No. 09/162,524, filed on Sep. 29, 1998, now Pat. No. 6,387,656.

(51) Int. Cl.
    *C07K 14/00* (2006.01)
(52) U.S. Cl. .......................................... 514/2; 530/350
(58) Field of Classification Search ............... 530/350; 514/2
See application file for complete search history.

(56) References Cited

U.S. PATENT DOCUMENTS 6,387,656 B1    5/2002  Jessell et al.
2002/0197678 A1*  12/2002  Jessell et al. ............. 435/69.1

FOREIGN PATENT DOCUMENTS

WO    WO 0018884    4/2000

OTHER PUBLICATIONS

Ahlgren, U. et al. (1996) "The Morphogenesis of the Pancreatic Mesenchyme Is Uncoupled from That of the Pancreatic Epithelium in IPF1/PDX1-deficient Mice", *Development* 122:1409-1416 (Exhibit 4).
Ahlgren, U. et al. (1997) "Independent Requirement for ISL1 in Formation of Pancreatic Mesenchyme and Islet Cells", *Nature* 385:257-260 (Exhibit 5).
Ahlgren, U. et al. (1998) "β-Cell-Specific Inactivation of the Mouse *Ipf1/Pdxl* Gene Results in Loss Of the β-Cell Phenotype And Maturity Onset Diabetes", *Genes & Dev.* 12:1763-1768 (Exhibit 6).
Aigner, L., et al. (1995) "Overexpression of the Neural Growth-Associated Protein GAP-43 Induces Nerve Sprouting in the Adult Nervous System of Transgenic Mice", *Cell* 83:269-278 (Exhibit 7).
Anderson, D.J. et al. (1997) "The Determination of the Neuronal Phenotype" in *Molecular and Cellular Approaches to Neural Development*, eds. Cowan, W.M., Jessell, T.M., and Zipursky, S.L. (Oxford University Press; New York, Oxford), pp. 26-63.

Apelqvist, A., et al. (1997) "Sonic Hedgehog Directs Specialised Mesoderm Differentiation in the Intestine and Pancreas", *Current Biology* 7:801-804 (Exhibit 8).
Appel, B., (1999) "LIMitless Combinations?", *Neuron* 22:3-5 (Exhibit 9).
Arber et al. (1999) "Requirement for the Homeobox Gene *Hb9* in the Consolidation of Motor Neuron Identity", *Neuron* 23:659-674.
Bang, A.G. et al. (1996) "Regulation of Vertebrate Neural Cell Fate by Transcription Factors", *Curr. Opin. Neurobiol.* 6:25-32.
Barber, R.P. et al. (1991) Generation Patterns of Immunocytochemically Identified Cholinergic Neurons at Autonomic Levels of the Rat Spinal Cord. *J. Comp. Neurol.* 311:509-519 (Exhibit 10).
Basler, K. et al. (1993) "Control of Cell Pattern in the Neural Tube: Regulation of Cell Differentiation by Dorsalin-1, a Novel TGF Beta Family Member", *Cell* 73:687-702.
Begley, C.G. et al. (1992) "Molecular Characterization of *nscl*, a Gene Encoding a Helix-loop-helix Protein Expressed in the Developing Nervous System", *Proc. Natl. Acad. Sci. USA* 89:38-42.
Bitgood, M.J. et al. (1995) "Hedgehog and *Bmp* Genes Are Coexpressed at Many Diverse Sites of Cell-Cell Interaction in the Mouse Embryo", *Dev. Biol.* 172:126-138 (Exhibit 11).
Branch, A.D. (1998) "A Good Antisense Molecule Is Hard To Find", *Trends in Biochemical Sciences* 23: 45-50.
Briscoe, J. et al. (1999) "Homeobox Gene *Nkx2.2* and Specification of Neuronal Identity by Graded Sonic hedgehog Signalling", *Nature* 398:622-627 (Exhibit 12).
Burke, A.C. et al. (1996) "Virally Mediated Misexpression of *Hoxc-6* in the Cervical Mesoderm Results in Spinal Nerve Truncations", *Dev. Biol.* 178:192-197.
Cepko, C.L. (1999) "The Roles of Intrinsic and Extrinsic Cues and bHLH Genes in the Determination of Retinal Cell Fates", *Curr. Opin. Neurobiol* 9:37-46 (Exhibit 13).
Chen, R. et al. (1997) "Dachshund and Eyes Absent Proteins Form a Complex and Function Synergistically to Induce Ectopic Eye Development in Drosophila", *Cell* 91:893-903.
Chiang, C. et al. (1996) "Cyclopia and Defective Axial Patterning in Mice Lacking Sonic Hedgehog Gene Function", *Nature* 383:407-413.
Crook, ed. (1998) in *Basic Principles of Antisense Therapeutics* (Springer-Verlag; New York), pp. 1 and 4.

(Continued)

*Primary Examiner*—Karen Cochrane Carlson
(74) *Attorney, Agent, or Firm*—John P. White; Cooper & Dunham LLP

(57) ABSTRACT

This invention provides isolated nucleic acids encoding a motor neuron restricted MNR2 protein, and a homeobox HB9 protein. Also provided are purified MNR2 and HB9 proteins, antibodies recognizing these proteins, transgenic animals expressing these proteins, and functionally equivalent analogs of these proteins. Finally, methods are disclosed for inducing differentiation of somatic motor neurons, and for treating diseases related to the lack of normally functioning motor neurons, neurodegenerative diseases, acute nervous system injury, and neuromuscular disease.

5 Claims, 27 Drawing Sheets

OTHER PUBLICATIONS

Database Tumor Gene Index (Jun. 1998) Accession No. A1560820. NCI-CGAP. National Cancer Institute, Cancer Genome Anatomy Project (CGAP), Tumor Gene Index.

Deguchi et al. (1991) "Nucleotide Sequence of a Novel Diverged Human Homeobox Gene Encodes a DNA Binding Protein", *Nucleic Acids Research* 19:3742.

Ding, Q. et al. (1998) "Diminished Sonic Hedgehog Signaling and Lack of Floor Plate Differentiation in Gli2 Mutant Mice", *Development* 125:2533-2543.

Dutta, S. et al. (1998) "Regulatory Factor Linked to Late-Onset Diabetes?", *Nature* 392:560 (Exhibit 4).

Edlund, H. (1998) "Perspectives in Diabetes: Transcribing Pancreas", *Diabetes* 47:1817-1823 (Exhibit 15).

Edlund, T. et al. (1999) "Progression from Extrinsic to Intrinsic Signaling in Cell Fate Specification: a View from the Nervous System", *Cell* 96:211-224 (Exhibit 16).

Ensini, M. et al. (1998) "The Control of Rostrocaudal Pattern in the Developing Spinal Cord: Specification of Motor Neuron Subtype Identity Is Initiated by Signals from Paraxial Mesoderm", *Development* 125:969-982 (Exhibit 17).

Ericson, J. et al. (1992) "Early Stages of Motor Neuron Differentation Revealed by Expression of Homeobox Gene Islet-1", *Science* 256:1555-60.

Ericson, J. et al. (1996) "Two Critical Periods of Sonic Hedgehog Signaling Required for the Specification of Motor Neuron Identity", *Cell* 87:661-673.

Ericson, J. et al. (1997) "Graded Sonic Hedgehog Signaling and the Specification of Cell Fate in the Ventral Neural Tube", *Cold Spring Harbor Symp. Quant. Biol.* 62:451-466 (Exhibit 18).

Ericson, J. et al. (1997) "Pax6 Controls Progenitor Cell Identity and Neuronal Fate in Response to Graded Shh Signaling", *Cell* 90:169-180.

Fedtsova, N. et al. (1997) "Inhibitory Effects of Ventral Signals on the Development of Brn-3.0-expressing Neurons in the Dorsal Spinal Cord", *Dev. Biol.* 190:18-31.

Goridis, C. (1999) "Transcriptional Control of Neurotransmitter Phenotype", *Curr. Opin. Neurobiol.* 9:47-53 (Exhibit 19).

Goulding, M. (1998) "Specifying Motor Neurons and Their Connections", *Neuron* 21:943-946 (Exhibit 20).

Halder, G. et al. (1995) "Introduction of Ectopic Eyes by Targeted Expression of the Eyeless Gene in Drosophila", *Science* 267:1788-1792.

Harrison, K.A. et al. (1994) "A Novel Human Homeobox Gene Distantly Related to Proboscipedia Is Expressed in Lymphoid and Pancreatic Tissues", *J. Biol. Chem.* 269:19968-19975.

Hebrok, M. et al. (1998) "Notochord Repression of Endodermal Sonic Hedgehog Permits Pancreas Development", *Genes & Dev.* 12:1705-1713 (Exhibit 21).

Hynes, M. et al. (1997) "Control of Cell Pattern in the Neural Tube by the Zinc Finger Transcription Factor and Oncogene Gli-1", *Neuron* 19:15-26.

Ingham, P.W. (1995) "Signaling by Hedgehog Family Proteins in Drosophila and Vertebrate Development", *Curr. Opin. Genet. Dev.* 5:492-498.

Jonsson, J. et al. (1994) "Insulin-Promoter-Factor 1 is Required for Pancreas Development in Mice", *Nature* 371:606-609 (Exhibit 22).

Jurata, L.W. et al. (1998) "The Nuclear LIM Domain Interactor Nli Mediates Homo-and Heterodimerization of Lim Domain Transcription Factors", *J. Biol. Chem.* 273:3152-3157.

Kalter, H. (1993) "Case Reports of Malformations Associated with Maternal Diabetes: History and Critique", *Clin. Genet.* 43:174-179 (Exhibit 23).

Kim, S.K. et al. (1997) "Notochord to Endoderm Signaling is Required for Pancreas Development", *Development* 124:4243-4252 (Exhibit 24).

Krapp, A. et al. (1998) "The bHLH Protein PTF1-p48 is Essential for the Formation of the Exocrine and the Correct Spatial Organization of the Endocrine Pancreas", *Genes & Dev.* 12:3752-3763 (Exhibit 25).

Lance-Jones, C. et al. (1981) "Pathway Selection by Embryonic Chick Motoneurons in an Experimentally Altered Environment", *Proceedings of the Royal Society of London, Series B, Biological Sciences* 214:19-52 (Exhibit 26).

Landmesser, L. (1978a) "The Distribution of Motorneurons Supplying Chick Hind Limb Muscles", *J. Physiol.* 284:371-389 (Exhibit 27).

Landmesser, L. (1978b) "The Development of Motor Projection Patterns in the Chick Hind Limb", *J. Physiol.* 284:391-414 (Exhibit 28).

Langman, J. et al. (1966) "Behavior of Neuroepithelial Cells During Closure of the Neural Tube", *J. Comp. Neurol.* 127:399-411.

Leber, S.M. et al. (1995) "Migratory Paths of Neurons and Glia in the Embryonic Chick Spinal Cord", *J. Neurosci.* 15:1236-1248.

Lee, J. et al. (1997) "Gli1 Is a Target of Sonic Hedgehog That Induces Ventral Neural Tube Development", *Development* 124:2537-2552.

Liem, K.F. et al. (1997) "A Role for the Roof Plate and its Resident TGF-beta-related Proteins in Neuronal Patterning in the Dorsal Spinal Cord", *Cell* 91:127-138.

Lin, J.H. et al. (1998) "Functionally Related Motor Neuron Pool and Muscle Sensory Afferent Subtypes Defined by Coordinate *ETS* Gene Expression", *Cell* 95:393-407 (Exhibit 29).

Liu, I.S.C. et al. (1994) "Developmental Expression of a Novel Murine Homeobox Gene (*Chx10*): Evidence for Roles in Determination of the Neuroretina and Inner Nuclear Layer", *Neuron* 13:377-393 (Exhibit 30).

Lo, L. et al. (1998) "MASH1 Activates Expression of the Paired Homeodomain Transcription Factor Phox2a, and Couples Panneuronal and Subtype-specific Components of Autonomic Neuronal Identity", *Development* 125:609-620.

Lo, L. et al. (1999) "Specification of Neurotransmitter Identity by Phox2 Proteins in Neural Crest Stem Cells", *Neuron* 22:693-705 (Exhibit 31).

Lumsden, A. et al. (1996) "Patterning the Vertebrate Neuraxis", *Science* 274:1109-1115.

Markham, J.A. et al. (1991) "Migration Patterns of Sympathetic Preganglionic Neurons in Embryonic Rat Spinal Cord", *J. Neurobiol.* 22:811-822 (Exhibit 32).

Marti, E. et al. (1995) "Requirement of 19k Form of Sonic Hedgehog for Induction of District Ventral Cell Types", *Nature* 375:322-325.

Matise M.P. et al. (1998) "Gli2 Is Required for Induction of Floor Plate and Adjacent Cells, but Not Most Ventral Neurons in the Mouse Central Nervous System", *Development* 125:2759-2770.

Matsuoka, T. et al. (1997) "Glycation-dependent, Reactive Oxygen Species-mediated Suppression of the Insulin Gene Promoter Activity in HIT Cells", *J. Clin. Invest.* 99:144-150 (Exhibit 33).

Naya, F.J. et al. (1997) "Diabetes, Defective Pancreatic Morphogenesis, and Abnormal Enteroendocrine Differentiation in BETA2/NeuroD-deficient Mice", *Genes & Dev.* 11:2323-2334 (Exhibit 34).

O'Brien, M.K. et al. (1990) "Development and Survival of Thoracic Motoneurons and Hindlimb Musculature Following Transplantation of the Thoracic Neural Tube to the Lumbar Region in the Chick Embryo: Anatomical Aspects", *J. Neurobiol.* 21:313-340 (Exhibit 35).

O'Brien, M.K. et al. (1990) "Development and Survival of Thoracic Motoneurons and Hindlimb Musculature Following Transplantation of the Thoracic Neural Tube to the Lumbar Region in the Chick Embryo: Functional Aspects", *J. Neurobiol.* 21:341-355 (Exhibit 36).

Offield, M.F. et al. (1996) "PDX-1 is Required for Pancreatic Outgrowth and Differentiation of the Rostral Duodenum", *Development* 122:983-995 (Exhibit 37).

Ohlsson, H. et al. (1993) "IPF1, a Homeodomain-containing Transactivator of the Insulin Gene", *EMBO J.* 12:4251-4259 (Exhibit 38).

Olson, L.K. et al. (1998) "Glucose Rapidly and Reversibly Decreases INS-1 Cell Insulin Gene Transcription via Decrements in STF-1 and C1 Activator Transcription Factor Activity", *Mol. Endocrinol.* 12:207-219 (Exhibit 39).

Osumi, N. et al. (1997) "Pax-6 Is Involved in Specification of the Hindbrain Motor Neuron Subtype", *Development* 124:2961-2972.

Pabst, O. et al. (1998) "Nkx2.9 Is a Novel Homeobox Transcription Factor Which Demarcates Ventral Domains in the Developing Mouse CNS", *Mech. Dev.* 73:85-93.

Pattyn, A. et al. (1997) "Expression and Interactions of the Two Closely Related Homeobox Genes Phox2a and Phox2b During Neurogenesis", *Development* 124: 4065-4075.

Pattyn, A. et al. (1999) "The Homeobox Gene *Phox2b* is Essential for the Development of Autonomic Neural Crest Derivatives", *Nature* 399:366-370 (Exhibit 40).

Pfaff, S. L. et al. (1996) "Requirement for LIM Homeobox Gene Isl1 in Motor Neuron Generation Reveals a Motor Neuron-dependent Step in Interneuron Differentiation", *Cell* 84:309-320.

Pfaff, S. et al. (1998) "Neuronal Diversification: Development of Motor Neuron Subtypes", *Curr. Opin. Neurobiol.* 8:27-36.

Pharmacia Biotech catalogue (1995) p. 277.

Pharmacia Biotech catalogue (1995) pp. 104-111.

Pictet, R., & Rutter, W.J. (1972) "Development of the Embryonic Endocrine Pancreas" in *Handbook of Physiology*, eds., D.F. Steiner, and N. Frenkel (Williams and Wilkins; Washington, D.C.) pp. 25-66 (Exhibit 41).

Pignoni, F. et al. (1997) "The Eye-Specification Proteins So and Eya Form a Complex and Regulate Multiple Steps in Drosophila Eye Development", *Cell* 91:881-891.

Riddle, R.D. et al. (1995) "Induction of the LIM Homeobox Gene *Lmx1* by WNT7a Establishes Dorsoventral Pattern in the Vertebrate Limb", *Cell* 83:631-640.

Roelink, H. et al. (1995) "Floor Plate and Motor Neuron Induction by Different Concentrations of the Amino-Terminal Cleavage Product of Sonic Hedgehog Autoproteolysis", *Cell* 81:445-455.

Ross, A.J. et al. (1998) "A Homeobox Gene, *HLXB9*, is the Major Locus for Dominantly Inherited Sacral Agenesis", *Nat. Genet.* 20:358-361 (Exhibit 42).

Roztocil, T. et al. (1997) "NeuroM, a Neural Helix-loop-helix Transcription Factor, Defines a New Transition Stage in Neurogenesis", *Development* 124:3263-3272.

Ruiz i Altaba et al. (1993) "Ectopic Neural Expression of a Floor Plate Marker in Frog Embryos Injected with the Midline Transcription Factor Pintallavis", *Proc. Natl. Acad. Sci USA* 90:8268-8272.

Ruiz i Altaba et al. (1995) "Restrictions to Floor Plate Induction by Hedgehog and Winged-helix Genes in the Neural Tube of Frog Embryos", *Mol. Cell Neurosci.* 6:106-121.

Saha, M.S. et al. (1997) "Dorsal-Ventral Patterning During Neural Induction in Xenopus: Assessment of Spinal Cord Regionalization with xHB9, a Marker for the Motor Neuron Region", *Dev. Biol.* 187:209-223.

Sander M. et al. (1997) "Genetic Analysis Reveals that PAX6 is Required for Normal Transcription of Pancreatic Hormone Genes and Islet Development", *Genes Dev.* 11:1662-1673 (Exhibit 43).

Sasaki, H. et al. (1994) "HNF-3 Beta as a Regulator of Floor Plate Development", *Cell* 76:103-115.

Schaeren-Wiemers, N. et al. (1993) "A Single Protocol to Detect Transcripts of Various Types and Expression Levels in Neural Tissue and Cultured Cells: in Situ Hybridization Using Digoxigenin-labeled cRNA Probes", *Histochemistry* 100:431-440.

Sharma, A. et al. (1995) "The Reduction of Insulin Gene Transcription in HIT-T15 Beta Cells Chronically Exposed to High Glucose Concentration Is Associated with the Loss of RIPE3b1 and STF-1 Transcription Factor Expression", *Mol. Endocrinol.* 9:1127-1134 (Exhibit 44).

Sharma, K. et al. (1998) "LIM Homeodomain Factors Lhx3 and Lhx4 Assign Subtype Identities for Motor Neurons", *Cell* 95:817-828 (Exhibit 45).

Slack, J.M.W. (1995) "Developmental Biology of the Pancreas", *Development* 121:1569-1580 (Exhibit 46).

Sockananthan, S. et al. (1998) "Motor Neuron- Derived Retinoid Signaling Specifies the Subtype Identity of Spinal Motor Neurons", *Cell* 94:503-514 (Exhibit 47).

Sosa-Pineda, B. et al. (1997) "The *Pax4* Gene Is Essential for Differentiation of Insulin-producing Beta Cells in the Mammalian Pancreas", *Nature* 386:399-402 (Exhibit 48).

Spooner, B.S. et al. (1970) "The Development of the Dorsal and Ventral Mammalian Pancreas In Vivo and In Vitro", *J. Cell. Biol.* 47:235-246 (Exhibit 49).

Stoffers, D.A. et al. (1997) "Early-onset Type-II Diabetes Mellitus (MODY4) Linked to *IPF1*", *Nature Genet.* 17:138-139 (Exhibit 50).

Stoffers, D.A. et al. (1997) "Pancreatic Agenesis Attributable to a Single Nucleotide Deletion in the Human *IPF1* Gene Coding Sequence", *Nature Genet.* 15:106-110 (Exhibit 51).

St-Onge, L. et al. (1997) "*Pax6* Is Required for Differentiation of Glucagon-producing Alpha-cells in Mouse Pancreas", *Nature* 387:406-409 (Exhibit 52).

Sussel, L. et al. (1998) "Mice Lacking the Homeodomain Transcription Factor Nkx2.2 Have Diabetes Due to Arrested Differentiation of Pancreatic Beta Cells", *Development* 125:2213-2221 (Exhibit 53).

Tanabe, Y. et al. (1995) "Introduction of Motor Neurons by Sonic Hedgehog Is Independent of Floor Plate Differentiation", *Curr. Biol.* 5:651-658.

Tanabe, Y. et al. (1996) "Diversity and Pattern in the Developing Spinal Cord", *Science* 274:1115-1123.

Tanabe, Y. et al. (1998) "Specification of Motor Neuron Identity by the MNR2 Homeodomain Protein", *Cell* 95:67-80.

Tanaka, H. et al. (1984) "Developmental Changes in Unique Cell Surface Antigens of Chick Embryo Spinal Motor Neurons and Ganglion Cells", *Dev. Biol.* 106:26-37.

Thaler et al. (1999) "Active Suppression of Interneuron Programs with Developing Motor Neurons Revealed by Analysis of Homeodomain Factor HB9", *Neuron* 23:675-687.

Tosney, K.W. et al. (1985) "Development of the Major Pathways for Neurite Outgrowth in the Chick Hindlimb", *Dev. Biol.* 109:193-214 (Exhibit 54).

Tsuchida, T. (1994) "Topographic Organization of Embryonic Motor Neurons Defined by Expression of LIM Homeobox Genes", *Cell* 79:957-70.

Varela-Echavarria, A. et al. (1996) "Differential Expression of LIM Homeobox Genes among Motor Neuron Subpopulations in the Developing Chick Brain Stem", *Mol. Cell. Neurosci.* 8:242-257.

Weintraub, H. (1993) "The MyoD Family and Myogenesis: Redundancy, Networks, and Thresholds", *Cell* 75:1241-1244.

Wessells, N.K. &. Cohen, J.H. (1967) "Early Pancreas Organogenesis: Morphogenesis, Tissue Interactions, and Mass Effects", *Dev. Biology* 15:237-270 (Exhibit 55).

Westendorf, J.M. et al. (1994) "Cloning of cDNAs for M-Phase Phosphoproteins Recognized by the MPM2 Monoclonal Antibody and Determination of the Phosphorylated Epitope", *Proc. Natl. Acad. Sci. USA* 91:714-718.

Wetts, R. et al. (1995) "Transient and Continuous Expression of NADPH Diaphorase in Different Neuronal Populations of Developing Rat Spinal Cord", *Dev. Dyn.* 202:215-228 (Exhibit 56).

Wildling, R. et al. (1993) "Agenesis of the Dorsal Pancreas in a Woman with Diabetes Mellitus and in Both of Her Sons", *Gastroenterology* 104:1182-1186 (Exhibit 57).

Yamada, T. et al. (1993) "Control of Cell Pattern in the Neural Tube: Motor Neuron Induction of Diffusible Factors From Notochord and Floor Plate", *Cell* 73:673-686; and.

Zhao, D. et al. (1996) "Molecular Identification of a Major Retinoic-Acid-Synthesizing Enzyme, a Retinaldehyde-Specific Dehydrogenase", *Eur. J. Biochem.* 240:15-22 (Exhibit 58).

Supplementary Partial European Search Report issued by the European Patent Office on Nov. 10, 2004 in connection with European Patent Application No. 99949964.3, filed Apr. 27, 2001, European Publication No. 111761, published Jul. 25, 2001, on behalf of the Trustees of Columbia University in the City of New York.

\* cited by examiner

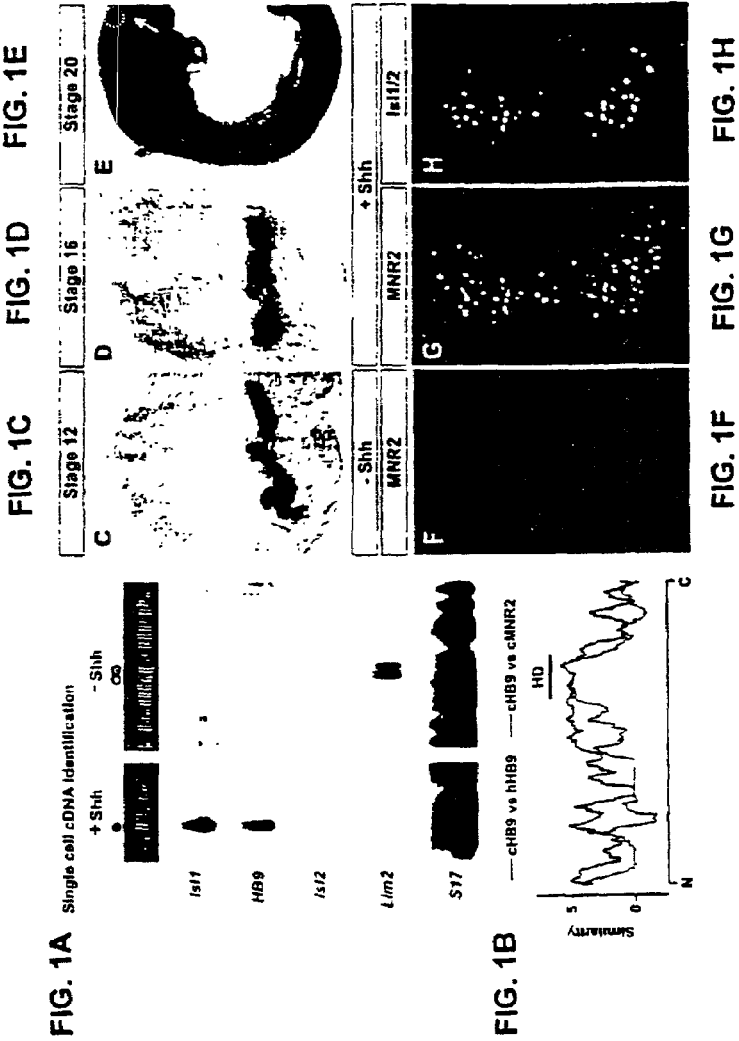

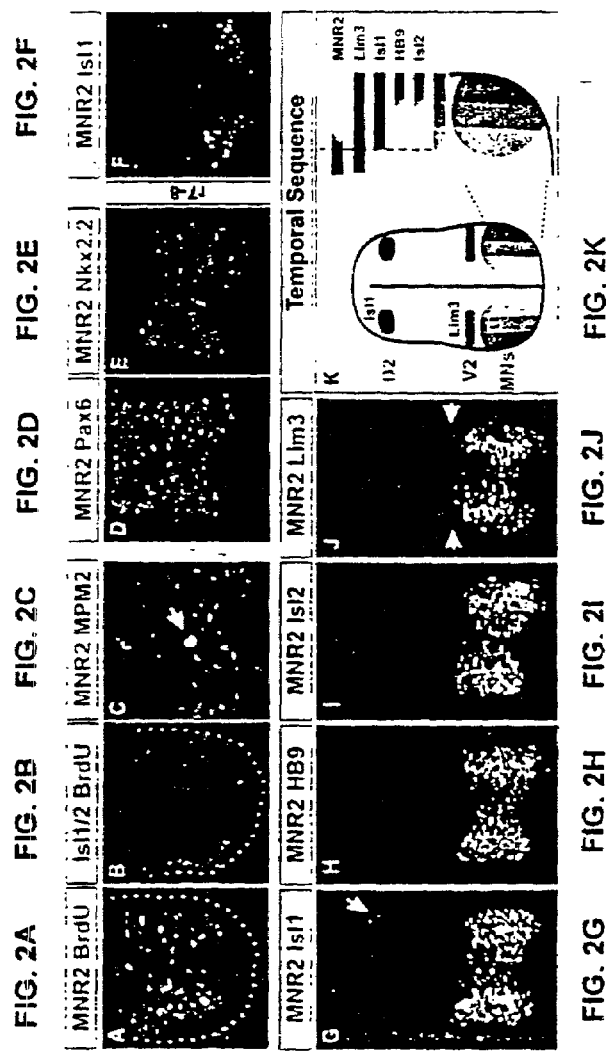

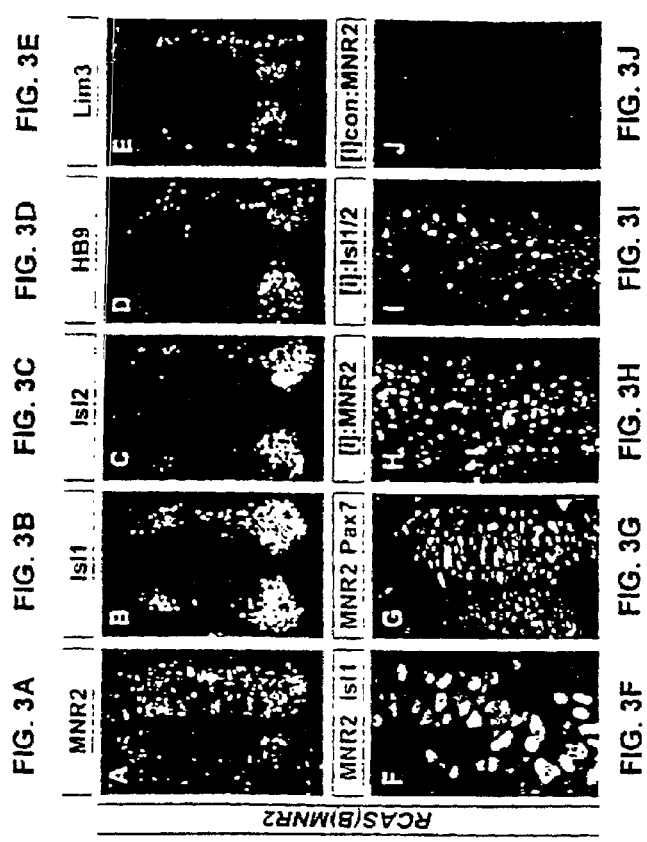

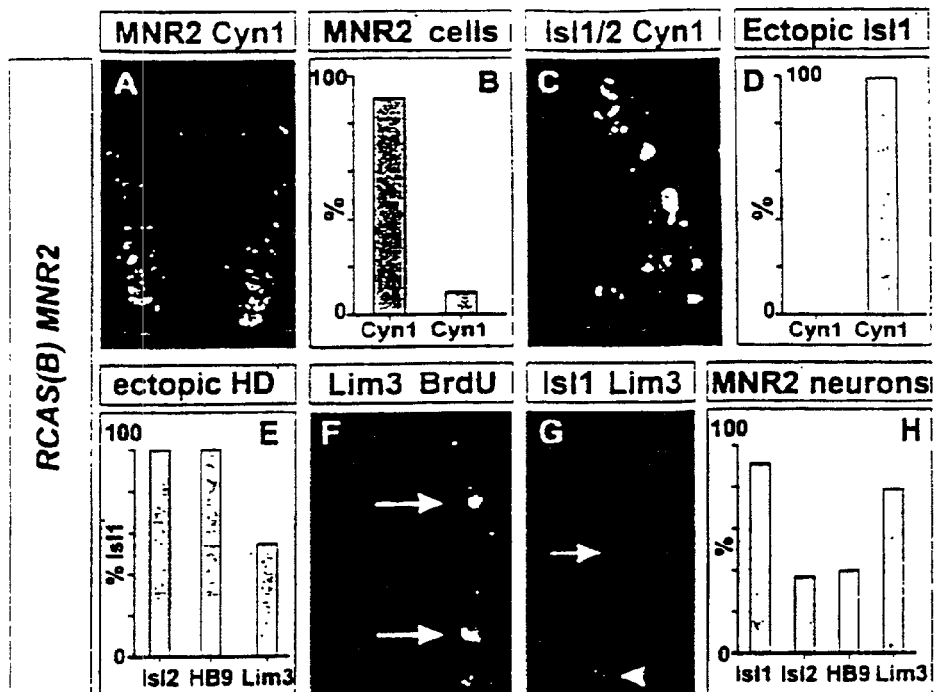
FIG. 4A  FIG. 4B  FIG. 4C  FIG. 4D
FIG. 4E  FIG. 4F  FIG. 4G  FIG. 4H
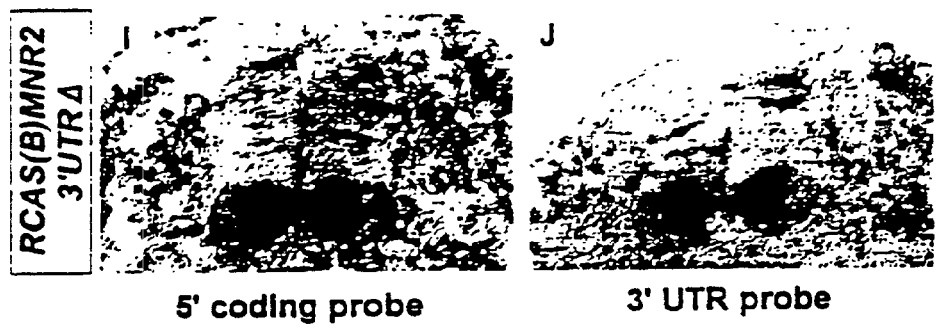
5' coding probe          3' UTR probe
FIG. 4I                  FIG. 4J

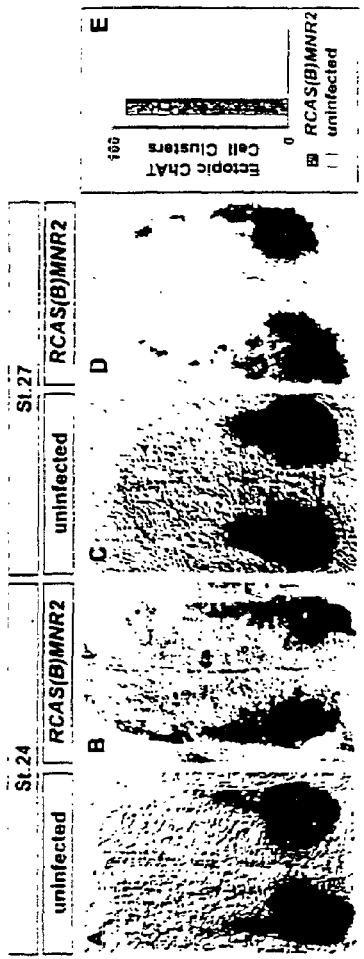

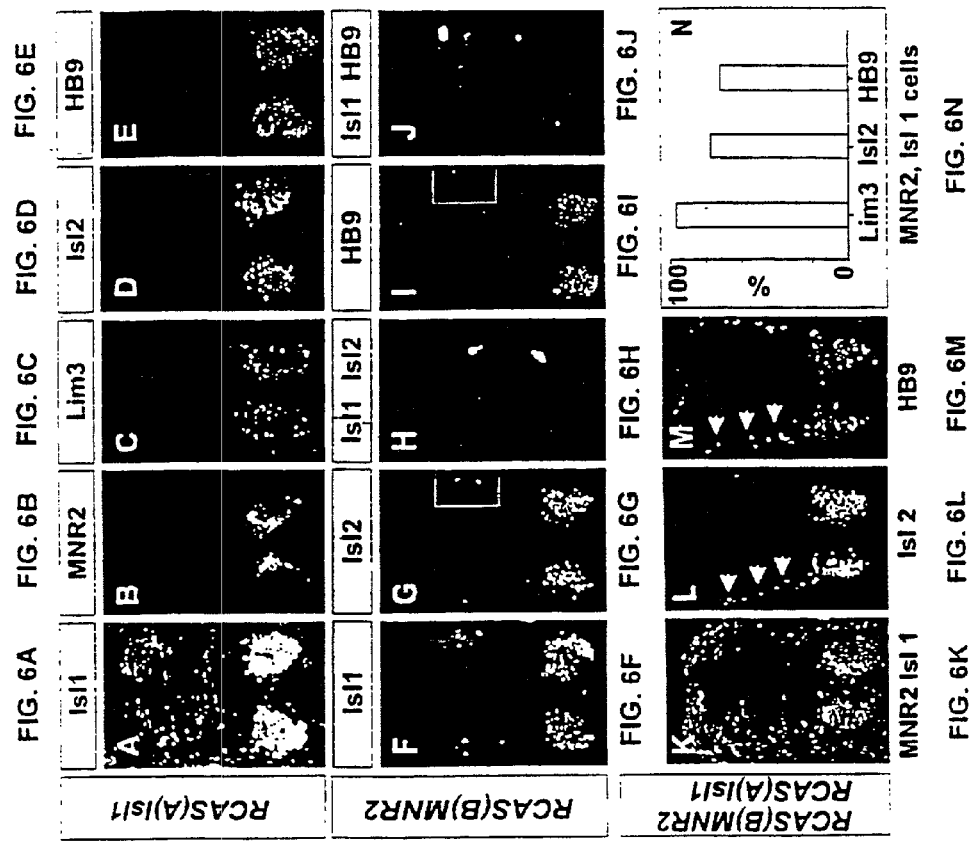

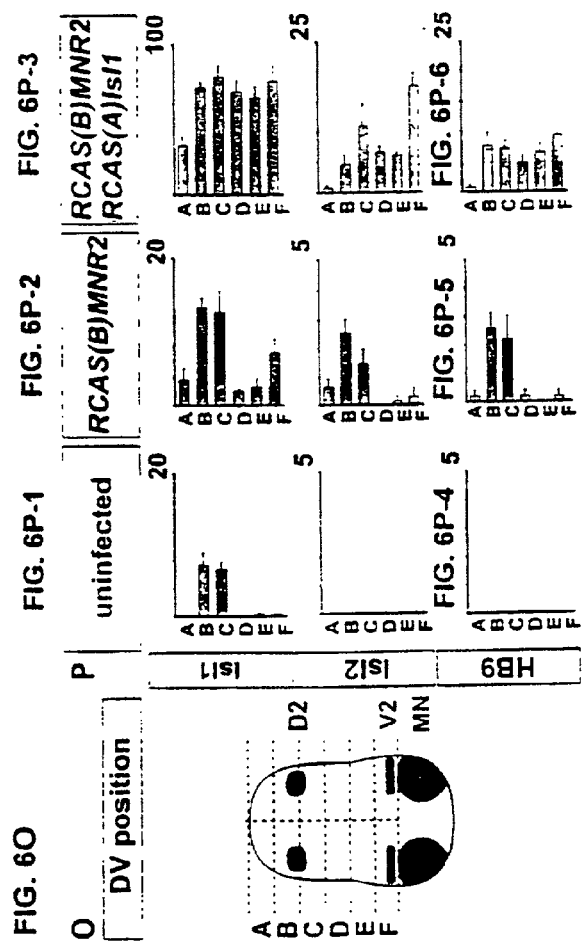

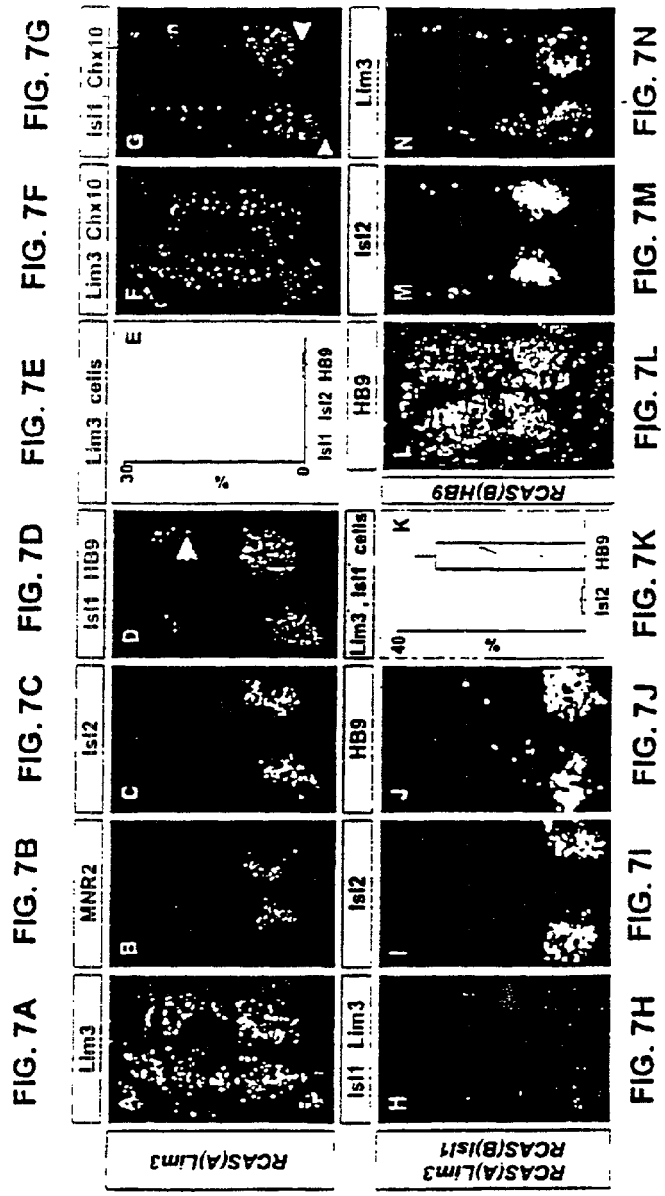

FIG. 9A
Interneuron Pattern
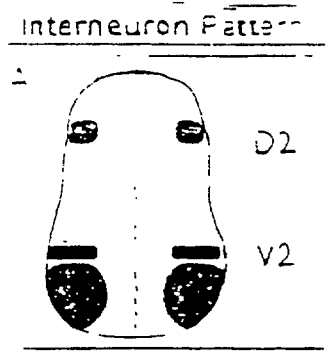
FIG. 9B
RCAS 3 MNR2
FIG. 9C  FIG. 9D  FIG. 9E
LH2    Isl1    LH2  Isl1
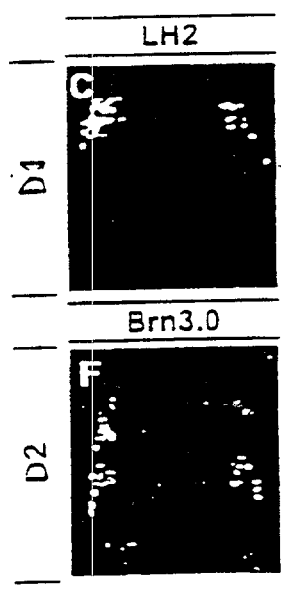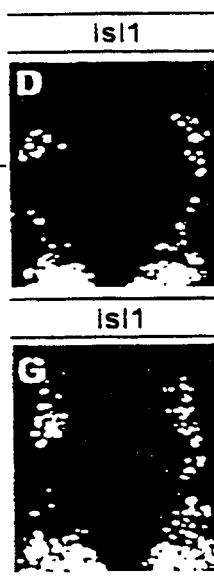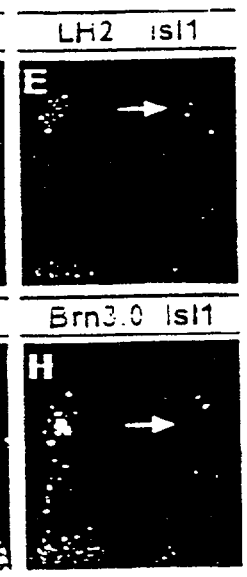
Brn3.0  Isl1   Brn3.0 Isl1
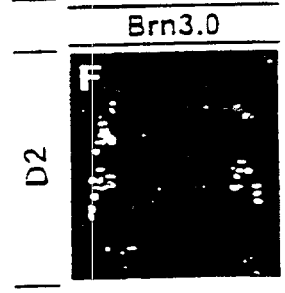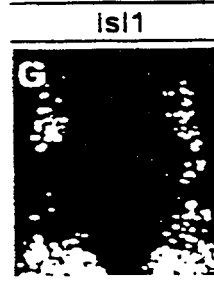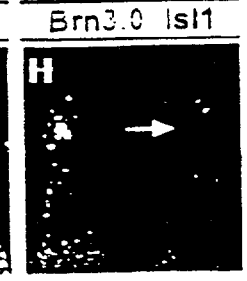
FIG. 9F  FIG. 9G  FIG. 9H

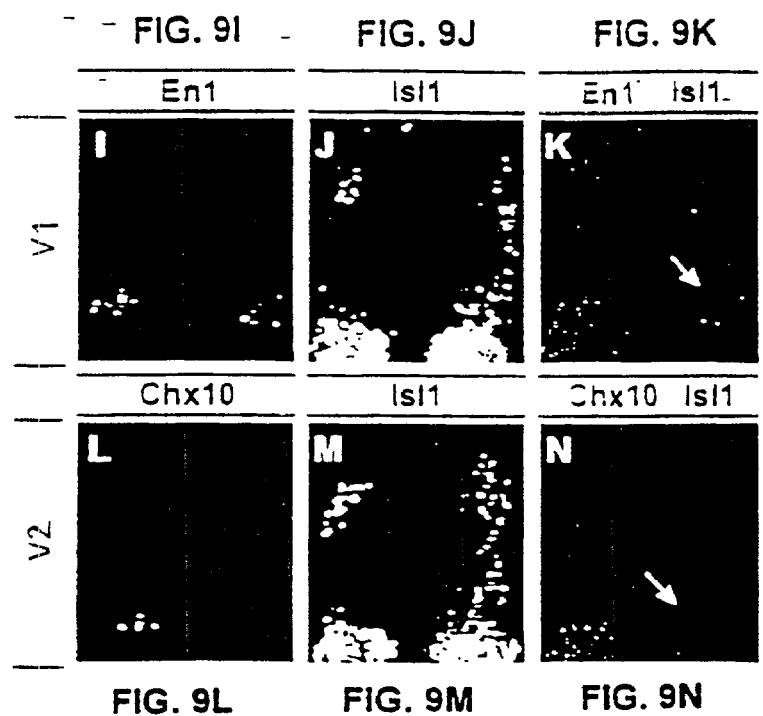

FIG. 10

SEQ. ID NO. 1 cMNR2-protein

```
  1 MIKPMEKSQN FRIEALLAEK PPRSASPPGL SPAGSPGPAG RTDTPSPRAP QAATPIGPAG
 61 FVPKPGLLHL PGPGLGTLPA LYPPAVYPLP ALGGQHAAFA YTAFPQLPPP GAEHLKAAVA
121 GSFPLEQWIR AGMLVPRLSD FHATPQSALM GKSRRPRTAF TSQQLLELEN QFKLNKYLSR
181 PKRFEVATSL MLTETQVKIW FQNRRMKWKR SRKAKEQGMA VEPEKPRGLG KADESLLPSQ
241 PGQQAGDSPE FVGCSPGTGF LCRSAELGYD PDSSCSGGEE DEEEDDGMD TAERKMGSVL
```

FIG. 11   cMNR2-dna

SEQ. ID NO. 2

```
   1 CAGATCTGCT CCCAGATGCT CTGCCTCTCC TTGAAGGCCA GAGTCGGTGG GTCCGGGCCA
  61 GCTCTGCTCC TGCTCACCCG CCTGTCCCAG AGCAGCCAAG GCTTTCATCT CCACCTGTTT
 121 CTGGTGCCTT CACCTGGAGA AGACCAAACC GAGCAAATAA ATAACAATCT GCCCGTATGC
 181 ACCTGCTCCA TGGGCTTCTT GGGCGGATAG ACGATGCAGG GTTGTGCCCC CTGCGTGCAG
 241 CCAGCTCGGG CCCCTGATG TCCCCGTGCC AAAGAGGAAC GGGCACGGGGT
 301 GTGAAGAGCA GGATCGGCC CCGGGGTGTG CCGAGGGCT GCGGAAGCCG GGGAGGCAG
 361 GCCGGGCCGA CGGGGCGGGG GGCCGGCGG GAGCCAATAG GGAGCTGGGG CAGGTGGAGG
 421 GGGGGTTAA AACCCCCCG GTGGCGGCGG GCAAGCGAGT GCCCGGGAGG AGGAGCGGTG
 481 AGGAGGGCTG CCCCTGAGGG CAGCGGAGGC CGGCGCGGCC CCGCGAGTGA ATGCCCGCCG
 541 GTGCCGGGGT GGCCCGCGGC TGCCCGGCCG GGGCCGGTCC TGGCAGCCGA GCGGCGGGGG
 601 GAGGCACGCT GCGTTTCGC GGGGCCCGGC CGGCCATGC ACAAACCCAT GGAGAAGTCC
 661 CAAAACTTCC GCATCGAGGC GCTCCTGGCT GAGAAGCCGC CGCGAGCGC CTCGCTCCCG
 721 GGGCTCAGCC CCGCGGCAG CCCCGGCCCC GCCGGCCGTA CCGACACCCC CTCGCTTGCTG
 781 GCTCCCCAGG CCGCACCCG CCTCGGCCG GGGCCTTCG TCCCCAAACC CGGCTTGCTG
 841 CACCTCCCCG GCCCCGGGCT GGGCACCCTG CCGGCCTCT ACCCGCCTGC CGTGTACCCG
 901 CTGCCGGCCT TGGGGGCCA GCACGCCGCT TTCGCCTACA CCGCCTTCCC CCAGCTGCCG
 961 CCGCCCGGCC CCGACACCT GAAGGCGGGG GTGCGCCGTT CCTTCCCGCT GGAGCAGTGC
1021 ATCCGAGCCG GATGCTCGT GCCGAGCTC GCCCCGCACC TCCGACTTCC ACGCCACCCC ACAGTCCCGC
1081 TTGATGGAA AGTCCTGGCCG TCAAGTCAA CAAGTATCTG GCCCAGCAGCT GCTGGAGCTG
1141 GAGAACCAGT TCAAGTCAA GCAGGTGAAG GTGTGTGAA GAGGCTTGA GAGGCTTGA GGTGGCCACG
1201 TCGCTGATCC TCACTGAGAC GCAAAGACT ATCTGTTCC AGAACCCCG AGTCAAGTCG
1261 AAGCGGAGCC GCAAAGCCAA GGAGCAGGGG ATGGCAGTGG AGCCCGAGAA GCCACGGGGG
1321 CTTGGCAAAG CTGATCGAGAG TCTGCTGCCC CCCCGGAACG GGCTTCCTGT GCTCGCAGCGC CGAGCTGCGC
1381 CCCGAGTTTG TGGGGTGCAG ACTCCTCTG TTCAGGGGGA GAGGAGGATG AGGAAGAGA GGACGATGG
1441 TATGACCCGG ACTCCTCTG CGGAGAGGAA GATGGGCTCT GTGTGTGAA GAGGTTCCCG GGTGAGGAGT
1501 ATGGACACTG CGGAGAGGAA GATGGGCTCT GTGTGTGAA GAGGTTCCCG GGTGAGGAGT
1561 TGGACCAGTC TCGGCTGGCA GACACAGACT GTGCCATCT GTGCACACGC GGCTGAGGGG
1621 AGCCTGCCC CCCCTCCTT TAACTTATGT TCTATTTATGT GTGTGACAGC
1681 TCCTGTGTGT ATCTTGGGGT TTCCCCACAT CCCTCCCCTA TAAAGCTGTT ATCCGG
```

FIG. 12

SEQ. ID NO. 3 cHB9-protein

```
  1 MEKSKNFRID ALLAVDPPKA AAQSAPLALV TGGSGGGSPP SSSSSSSSSS SSSSELPADC
 61 PRTDSPSPPR LLPAHCALLP KAAFLGGGGP GGGHPQHHAL GLHPAGPGGP GLYGHPVYGY
121 PALGGGHPAL SYSYSQVQGA HPAHPSADPI KLSAGTFQLD QWLRASTAGM ILPKMPDFGS
181 QAQSNLLGKC RRPRTAFTSQ QLLELEHQFK LNKYLSRPKR FEVATSLMLT ETQVKIWFQN
241 RRMKWKRQKK AKEQAAQEAE NEKGGGGED KSGPRELLLP GPEKGGGRRL RELPDSEPED
301 EEEEEEEEE AEAGRCCPYH SSDCSEADEE DSQSGGRPGA PPPPAQPQ*
```

FIG. 13
SEQ. ID NO. 4 cHB9 - DNA

```
   1  CCGGGCTGGC  CTCTCGCCGC  CTCCGCCGCT  CCCATGGAAA  AATCCAAAAA  TTTCCGCATC
  61  GACGGCTGC   TGGCTGTCGA  TCCCCCAAG   GCGGGGCGC   AGAGCGCTCC  GCTGGCCCTG
 121  GTCACCGGCG  GTCCGGCGG   CGGCAGCCCT  CCGTCTTCGT  CGGATCCCTC  CTGCTTGTCG
 181  TCCTCCTCTT  CTTCCTGACTT CCCCGCCGAC  TGCCCGCGCA  CCGACAGCCC  CTCTCCCCT
 241  CGCCTGCTGC  CCGCGCACTG  CGCGCTGCTG  CCCAAAGCCG  CCTTCCTGGG  CGGGGGGGA
 301  CCCGGGGGCG  GCCACCCGCA  GCACCACGCC  CTGGGGCTGC  ACCCGCGGG   GCCGGGCGG
 361  CCGGGCCTCT  ACGGGCACCC  GGTGTACGGC  TACCCGGCGT  TGGGCGGGCA  GCACCCGGCG
 421  CTCTCCTATT  CCTATTCGCA  AGTGCAGGGA  GCGCACCCCG  CGCATCCCTC  CGCCGACCCC
 481  ATCAAGCTGA  GCGCCGGCAC  CTTTCAGCTG  GACCAGTGGC  TGCGGGCGAG  CACGCCGGC
 541  ATGATCCTGC  CCAAAATGGC  CGACTTCGGC  TCTCAGGCGC  ATTCAACCT   GCTGGGAAG
 601  TGCCGGCGGC  CGCACCCGC  CTTCACCAGC  CAGCAGCTGC  TGGAGCTGGA  GCACCAGTTT
 661  AAACTCAACA  AGTACCTCTC  CCGGCCCAAG  CGCTTCGAGG  AACCGCCGCA  GCGCCAGAAA
 721  ACCGAGACGC  AGTGAAGAT   TTGGTTCCAG  AACCGCCGCA  TGAAATGGAA  GCGCCAGAGA
 781  AAGGCGAAGG  AGCAGGCGGC  GCAGGAGGCA  ACTGCTGCTG  CCCGCCCGG   AGAAAGGCGG  CGGAGCCGG
 841  GACAAAAGCG  GGCCGAGGGA  CGAGCCCGAG  GACGAGGAGG  AGAAGAAGA   GGAGAAGAAG
 901  CTGAGGGAGC  TGGCTGCTGC  CCGGCAGCC   CTGCCGGTG   CTGCCTCCGA  GCGGACGAG
 961  GAGGCGAGG   CCGGGCCGGG  CTGCCCGGTG  ACGGCCGGAG  GCCCCCCCGC  CACCCCCGC  ACAGCCGCAG
1021  GAGGCTCGC   AGTGCCACG   GCCGCCCCGT  CGGGGCCGCC  GAGCCTCCTG  GCCCCGCTCT
1081  TGAGCCCACG  GCCCCATCCC  TCCCTGCTCG  GAGGGGACG   CGGAAAGGGA  TCTCCCGTCT
1141  CCATCCCGCT  CTCCCCGGCT  AGGGAGGATT  CACACAGTGT  TATTATTGAC  CCACGACTTG
1201  GCCGAGCGGG  CCCGCCCCC   CCTATCGGAA  CCGTTTCCTT  CTTACCATAT  ATCGGGAAAA
1261  AGCCCCCCTC  CATGAACCTT  AAAACTGCTG  CAGATCTCAA  TACTGTCTTT  ATTGTTATA
1321  GTGTTTATGT  CATGAACCTT  AAAAAAGGCA  AAATGAATTC  CTCTACTTAT  GCATGCTAAA  TTATTACCCA
1381  TCCTATTTAT  AAAAAGGCA   AAATGAATTC  CTCTACTTAT  GCATGCTAAA  TTATTACCCA
1441  GCCCCTTCCG  CCTGAGGTGG  GGGGAGGAA   TATAAATAAA  GAGCGTTTTG  TACTGTGAAA
1501  AAAAAAAAA   AAAA
``` e9.5 ⟶ e10

Lim3 / BrdU   e9.75 ——— HB9 / BrdU ⟶ e10

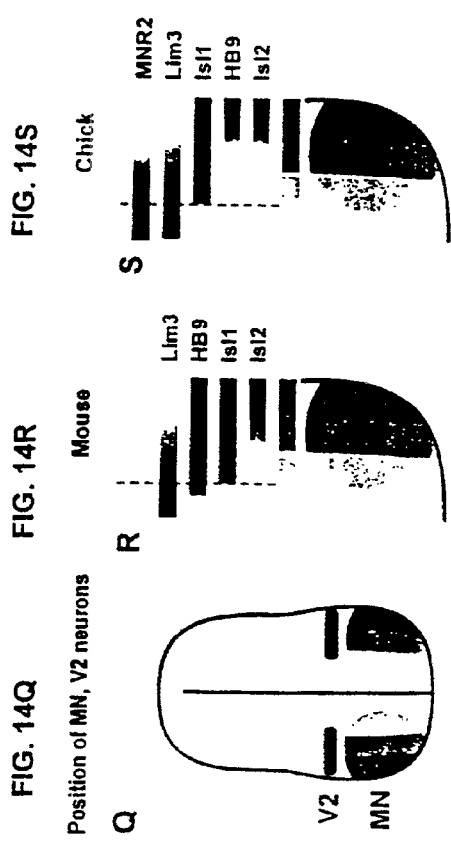

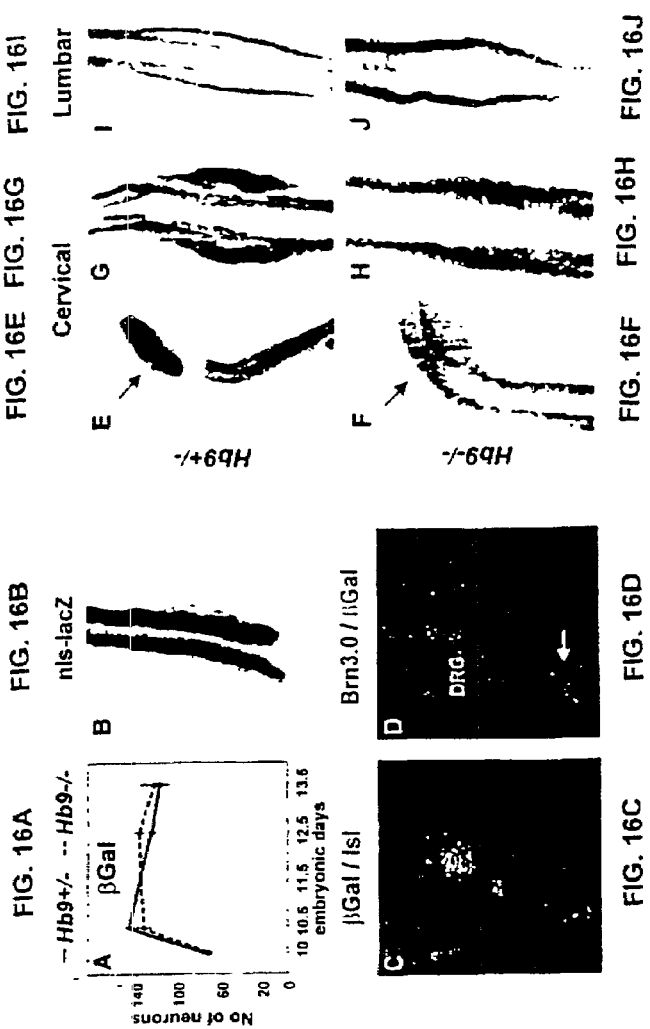

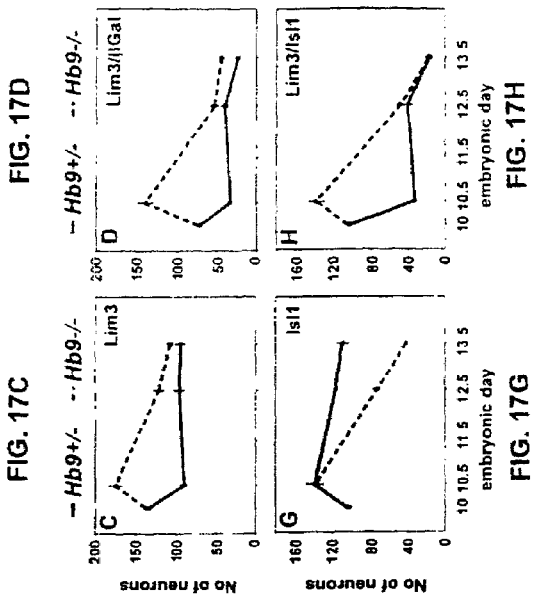
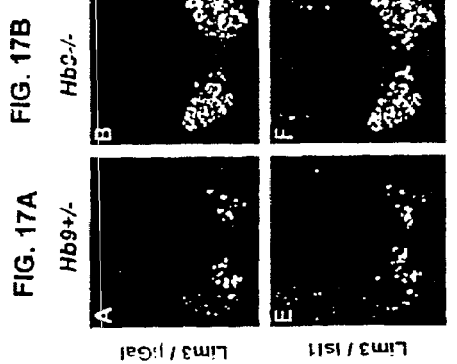

FIG. 18A  FIG. 18B  FIG. 18C
Hb9+/−   − Hb9−/−   — Hb9+/−   ·· Hb9−/−
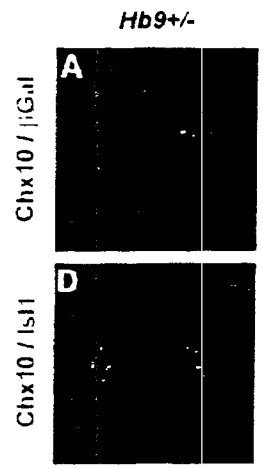
Chx10 / βGal
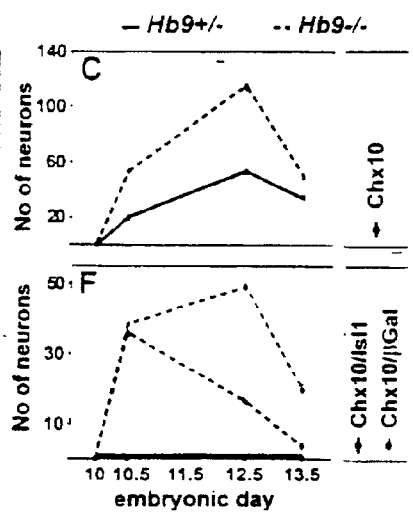
FIG. 18D  FIG. 18E  FIG. 18F
Chx10 / Isl1
FIG. 18G  FIG. 18I  FIG. 18K  FIG. 18M
Chx10 / HRP   Chx10 / Isl   Myc   NF160 / Myc
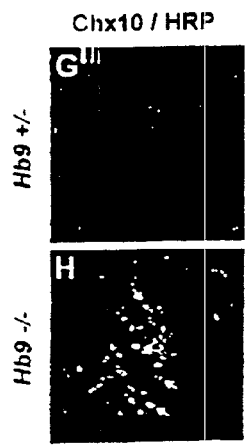
Hb9 +/−
Hb9 −/−
FIG. 18H  FIG. 18J  FIG. 18L  FIG. 18N

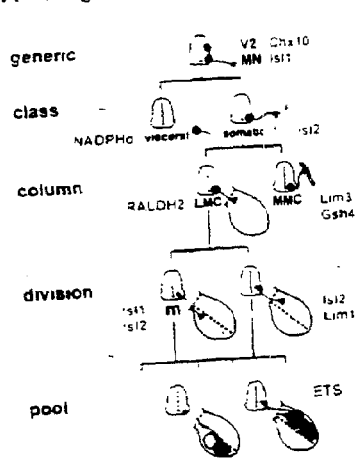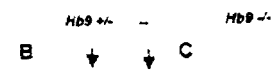

FIG. 20A  FIG. 20B  FIG. 20C  FIG. 20D
Hb9 $^{taulacZ/+}$       Hb9 $^{taulacZ/taulacZ}$
   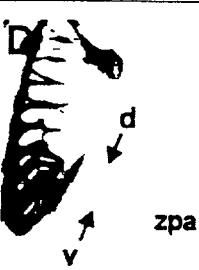
FIG. 20E  FIG. 20F  FIG. 20G  FIG. 20H
Hb9 $^{taumyc/+}$       Hb9 $^{taumyc/taumyc}$
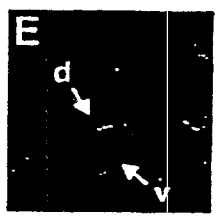 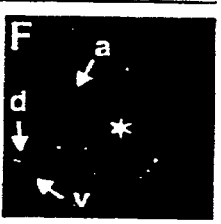 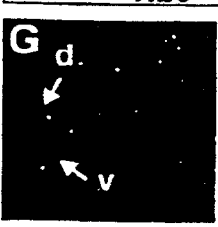 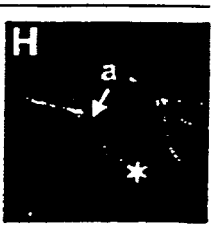
FIG. 20I  FIG. 20J  FIG. 20K  FIG. 20L
Hb9 $^{nlslacZ/+}$  Hb9 $^{nlslacZ/nlslacZ}$  Hb9 $^{nlslacZ/+}$  Hb9 $^{nlslacZ/nlslacZ}$
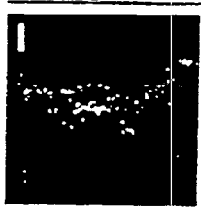   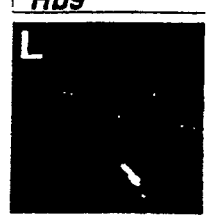
FIG. 21
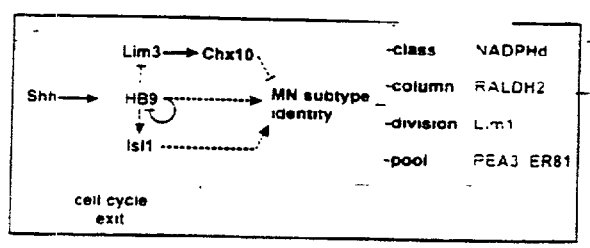

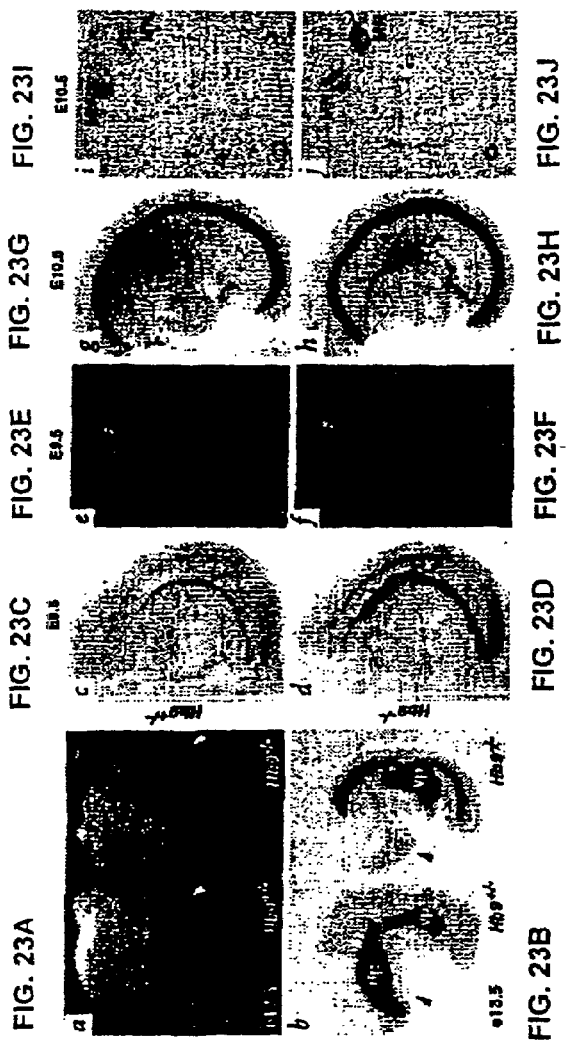

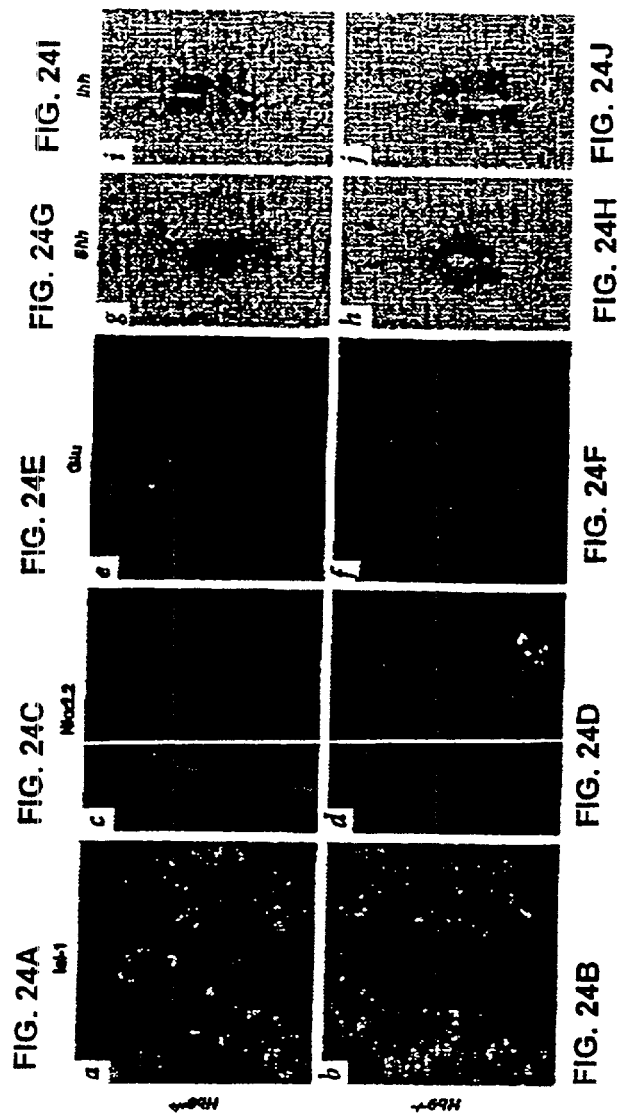

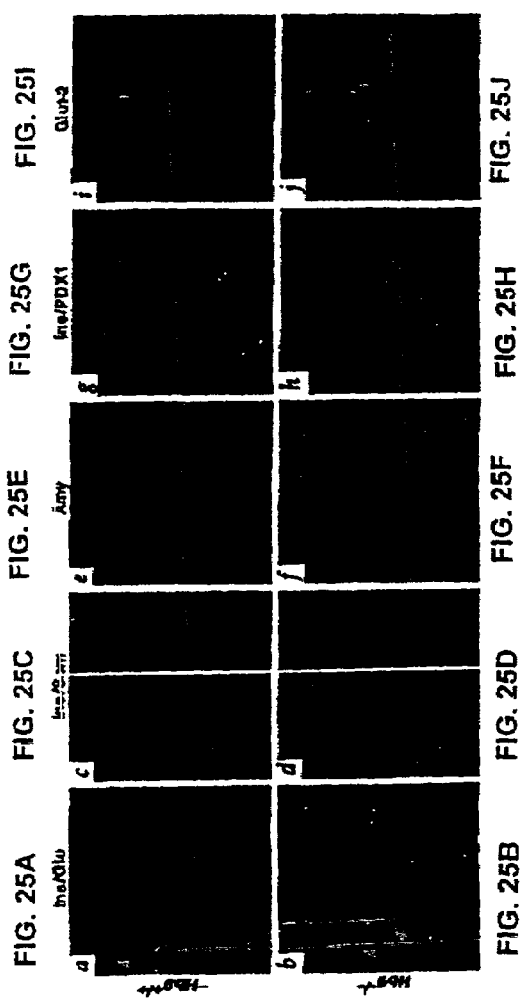

SEQUENCE LISTING

<160> NUMBER OF SEQ ID NOS: 4

<210> SEQ ID NO 1
<211> LENGTH: 300
<212> TYPE: PRT
<213> ORGANISM: chick embryo

<400> SEQUENCE: 1

```
Met His Lys Pro Met Glu Lys Ser Gln Asn Phe Arg Ile Glu Ala Leu
1               5                   10                  15

Leu Ala Glu Lys Pro Pro Arg Ser Ala Ser Pro Pro Gly Leu Ser Pro
            20                  25                  30

Ala Gly Ser Pro Gly Pro Ala Gly Arg Thr Asp Thr Pro Ser Pro Arg
        35                  40                  45

Ala Pro Gln Ala Ala Thr Pro Leu Gly Pro Ala Gly Phe Val Pro Lys
    50                  55                  60

Pro Gly Leu Leu His Leu Pro Gly Pro Gly Leu Gly Thr Leu Pro Ala
65                  70                  75                  80

Leu Tyr Pro Pro Ala Val Tyr Pro Leu Pro Ala Leu Gly Gly Gln His
                85                  90                  95

Ala Ala Phe Ala Tyr Thr Ala Phe Pro Gln Leu Pro Pro Pro Gly Ala
            100                 105                 110

Glu His Leu Lys Ala Ala Val Ala Gly Ser Phe Pro Leu Glu Gln Trp
        115                 120                 125

Ile Arg Ala Gly Met Leu Val Pro Arg Leu Ser Asp Phe His Ala Thr
    130                 135                 140

Pro Gln Ser Ala Leu Met Gly Lys Ser Arg Arg Pro Arg Thr Ala Phe
```

-continued

```
                    145                 150                 155                 160
Thr Ser Gln Gln Leu Leu Glu Leu Glu Asn Gln Phe Lys Leu Asn Lys
                165                 170                 175
Tyr Leu Ser Arg Pro Lys Arg Phe Glu Val Ala Thr Ser Leu Met Leu
            180                 185                 190
Thr Glu Thr Gln Val Lys Ile Trp Phe Gln Asn Arg Arg Met Lys Trp
        195                 200                 205
Lys Arg Ser Arg Lys Ala Lys Glu Gln Gly Met Ala Val Glu Pro Glu
    210                 215                 220
Lys Pro Arg Gly Leu Gly Lys Ala Asp Glu Ser Leu Leu Pro Ser Gln
225                 230                 235                 240
Pro Gln Gly Gln Ala Gly Asp Ser Pro Glu Phe Val Gly Cys Ser Pro
                245                 250                 255
Gly Thr Gly Phe Leu Cys Arg Ser Ala Glu Leu Gly Tyr Asp Pro Asp
            260                 265                 270
Ser Ser Cys Ser Gly Gly Glu Asp Glu Glu Glu Asp Asp Gly
        275                 280                 285
Met Asp Thr Ala Glu Arg Lys Met Gly Ser Val Leu
    290                 295                 300

<210> SEQ ID NO 2
<211> LENGTH: 356
<212> TYPE: DNA
<213> ORGANISM: chick embryo

<400> SEQUENCE: 2
cccgagtttg tggggtgcag ccccggaacg ggcttcctgt gccgcagcgc cgagctgggc     60
tatgacccgg actcctcctg ttcagggggga gaggaggatg aggaagagga ggacgatggg    120
atggacactg cggagaggaa gatgggctct gtgttgtgaa aggttcccg ggtgaggagt      180
tggaccagtc tcggctggca gacacagact gtgcccatgt gcagcgtggg ggctgagggg    240
agcctgcccc ccccctcctt taacttatgt gtgtttggag tctatttaat gtgtaattat    300
tcctgtgtgt atcttggggt ttccccacat ccctccccta taaagctgtt atccgg        356

<210> SEQ ID NO 3
<211> LENGTH: 349
<212> TYPE: PRT
<213> ORGANISM: chick embryo

<400> SEQUENCE: 3

Met Glu Lys Ser Lys Asn Phe Arg Ile Asp Ala Leu Leu Ala Val Asp
1               5                   10                  15
Pro Pro Lys Ala Ala Gln Ser Ala Pro Leu Ala Leu Val Thr Gly
            20                  25                  30
Gly Ser Gly Gly Gly Ser Pro Pro Ser Ser Ser Ser Ser Ser Ser Ser
        35                  40                  45
Ser Ser Ser Ser Ser Glu Leu Pro Ala Asp Cys Pro Arg Thr Asp
    50                  55                  60
Ser Pro Ser Pro Pro Arg Leu Leu Pro Ala His Cys Ala Leu Leu Pro
65                  70                  75                  80
Lys Ala Ala Phe Leu Gly Gly Gly Gly Pro Gly Gly Gly His Pro Gln
                85                  90                  95
His His Ala Leu Gly Leu His Pro Ala Gly Pro Gly Gly Pro Gly Leu
            100                 105                 110
Tyr Gly His Pro Val Tyr Gly Tyr Pro Ala Leu Gly Gly Gln His Pro
```

-continued

```
                115                 120                 125
Ala Leu Ser Tyr Ser Tyr Ser Gln Val Gln Gly Ala His Pro Ala His
    130                 135                 140

Pro Ser Ala Asp Pro Ile Lys Leu Ser Ala Gly Thr Phe Gln Leu Asp
145                 150                 155                 160

Gln Trp Leu Arg Ala Ser Thr Ala Gly Met Ile Leu Pro Lys Met Pro
                165                 170                 175

Asp Phe Gly Ser Gln Ala Gln Ser Asn Leu Leu Gly Lys Cys Arg Arg
                180                 185                 190

Pro Arg Thr Ala Phe Thr Ser Gln Gln Leu Leu Glu Leu Glu His Gln
                195                 200                 205

Phe Lys Leu Asn Lys Tyr Leu Ser Arg Pro Lys Arg Phe Glu Val Ala
    210                 215                 220

Thr Ser Leu Met Leu Thr Glu Thr Gln Val Lys Ile Trp Phe Gln Asn
225                 230                 235                 240

Arg Arg Met Lys Trp Lys Arg Gln Lys Lys Ala Lys Glu Gln Ala Ala
                245                 250                 255

Gln Glu Ala Glu Asn Glu Lys Gly Gly Gly Gly Glu Asp Lys Ser
    260                 265                 270

Gly Pro Arg Glu Leu Leu Leu Pro Gly Pro Glu Lys Gly Gly Gly Arg
                275                 280                 285

Arg Leu Arg Glu Leu Pro Asp Ser Glu Pro Glu Asp Glu Glu Glu
    290                 295                 300

Glu Glu Glu Glu Glu Glu Ala Glu Ala Gly Arg Cys Cys Pro Tyr His
305                 310                 315                 320

Ser Ser Asp Cys Ser Glu Ala Asp Glu Glu Asp Ser Gln Ser Gly Gly
                325                 330                 335

Arg Pro Gly Ala Pro Pro Pro Pro Ala Gln Pro Gln
    340                 345
```

<210> SEQ ID NO 4
<211> LENGTH: 1513
<212> TYPE: DNA
<213> ORGANISM: chick embryo

<400> SEQUENCE: 4

| | |
|---|---|
| ccgggctggc ctctcgccgc ctccgccgct cccatggaaa aatccaaaaa tttccgcatc | 60 |
| gacgcgctgc tggctgtcga tccccccaag gcggcggcgc agagcgctcc gctgccctgg | 120 |
| tcaccggcgg ctccggcggc ggcagccctc cgtcttcgtc gtcctcctcg tcgtcgtcgt | 180 |
| cctcctcttc ttccgagctc cccgccgact gcccgcgcac cgacagcccc tctccgcctc | 240 |
| gcctgctgcc cgcgcactgc gcgctgctgc ccaaagccgc cttcctgggc gggggggac | 300 |
| ccggggggcgg ccacccgcag caccacgccc tgggctgca ccccgcgggg ccgggcgggc | 360 |
| cgggcctcta cgggcacccg gtgtacggc accggcgtt gggcgggcag cacccggcgc | 420 |
| tctcctattc ctattcgcaa gtgcaggag cgcaccccgc gcatccctcc gccgaccca | 480 |
| tcaagctgag cgccggcacc tttcagctgg accagtggct cgggcgagc acggccggca | 540 |
| tgatcctgcc caaaatgccc gacttcggct ctcaggcgca gtccaacctg ctggggaagt | 600 |
| gccggcggcc gcgcaccgcc ttcaccagca gcagctgct ggagctggag caccagttca | 660 |
| aactcaacaa gtacctctcc cggcccaagc gcttcgaggt ggccacgtcg ctgatgctca | 720 |
| ccgagacgca ggtgaagatt tggttccaga accgccgcat gaaatggaag cgccagaaaa | 780 |
| aggcgaagga gcaggcggcg caggaggcag agaacgagaa aggaggagga ggaggagagg | 840 |

```
acaaaagcgg gccgagggaa ctgctgctgc ccggcccgga gaaaggcggc gggaggcggc      900
tgagggagct gcccgacagc gagcccgagg acgaggagga ggaagaagag gaggaagagg      960
aggccgaggc cgggcggtgc tgcccctacc actcctccga ctgctccgag gcggacgagg     1020
aggactcgca gtccggagga cggcccggag ccccccgcc acccccgca cagccgcagt       1080 gagcccacgg ccgccccgtc ggggccgccc ccggcaacgg agcctcctgg ccccgctctc     1140
catcccgctc tcccatccct ccctgctcgg aggggggacgc ggaaagggat ctcccgtctg    1200
ccgagcggga gggaggattc acacagtgtt attattgact gagaagcggc cacgacttga     1260 gccccctcc ccgccccgcc ctatcggaac cgtttccttc ttaccatata tcgggaaaag      1320
tgtttatgtc atgaacgtta aaactgctgc agatctcaat actgtctta ttttgtatat     1380 cctatttata aaaaggcaa aatgaattcc tctacttatg catgctaaat tattacccag      1440
ccccttccgc ctgaggtggg ggggaggaat ataaataaag agcgttttgt actgtgaaaa    1500
aaaaaaaaaa aaa                                                        1513
```

GENE ENCODING MNR2 AND USES THEREOF

This application is a continuation of PCT International Application No. PCT/US99/22517, filed 29 Sep. 1999, designating the United States of America, which is a continuation-in-part and claims priority of U.S. Ser. No. 09/162,524, filed Sep. 29, 1998, now U.S. Pat. No. 6,387,656 B1, issued May 14, 2002, the contents of which are hereby incorporated by reference into the present application.

The invention disclosed herein was made with support under National Institute of Health training grant No. 5T32GM07367, U.S. Department of Health and Human Services. Accordingly, the United States Government has certain rights in this invention.

This application claims priority of and is a continuation-in-part of U.S. Ser. No. 09/162,524, filed Sep. 29, 1998, the content of which is hereby incorporated by reference.

Throughout this application various publications are referred to within parenthesis. Full citations for these publications may be found at the end of the specification immediately preceding the claims. The disclosures of these publications, in their entireties, are hereby incorporated by reference into this application in order to more fully describe the state of the art to which this invention pertains.

BACKGROUND OF THE INVENTION

Sonic hedgehog signaling controls the differentiation of motor neurons in the ventral neural tube but the intervening steps are poorly understood. A differential screen of a cDNA library derived from a single Shh-induced motor neuron has identified a novel homeobox gene, MNR2, expressed by motor neuron progenitors and transiently by post-mitotic motor neurons. The ectopic expression of MNR2 in neural cells initiates a program of somatic motor neuron differentiation characterized by the expression of homeodomain proteins, by neurotransmitter phenotype and by axonal trajectory. Our results suggest that the Shh-mediated induction of a single transcription factor, MNR2, is sufficient to direct somatic motor neuron differentiation.

The assembly of neural circuits in the vertebrate central nervous system (CNS) is initiated by the generation of distinct classes of neurons at characteristic positions. The specification of neuronal identity in the CNS appears to be controlled by inductive signals secreted by embryonic organizing centers (Lumsden and Krumlauf, 1996; Tanabe and Jessell, 1996). These signals appear to define neuronal fates by regulating the expression of cell-intrinsic determinants, many of which are transcription factors (Bang and Goulding, 1996). However, the pathways by which specific inductive signals determine the fate of individual neuronal cell types in the CNS are poorly defined. As a consequence, it is unclear whether there are individual transcription factors assigned, in a dedicated manner, to the specification of particular neuronal subtypes or whether the parallel actions of several factors are required.

Spinal motor neurons constitute one subclass of CNS neuron for which some early differentiation steps have been defined (Pfaff and Kintner, 1998). The differentiation of motor neurons depends on spatial signals provided by Sonic Hedgehog (Shh) secreted from the notochord and floor plate (Marti et al. 1995; Roelink et al., 1995; Tanabe et al., 1995; Chiang et al. 1996; Ericson et al. 1996). Shh acts initially to convert medial neural plate cells into a population of ventral progenitors (Ericson et al., 1996) and later directs the differentiation of ventral progenitors into motor neurons and interneurons at distinct concentration thresholds (Roelink et al. 1995; Ericson et al., 1997). The Shh-induced pathway of motor neuron differentiation appears, however, to operate within the context of an independent program of neurogenesis. Neural progenitors that have been exposed to Shh undergo two or more cell divisions before leaving the cell cycle and acquiring motor neuron properties (Ericson et al., 1996). Over this period, ventral progenitors require continued Shh signaling, achieving Shh-independence and committing to a motor neuron fate only late in their final division cycle (Ericson et al., 1996).

Cells in the ventral neural tube respond to graded Shh signaling with the establishment of distinct ventral progenitor populations defined by the expression of the homeodomain proteins Pax6 and Nkx2.2 (Ericson et al., 1997). These two progenitor populations generate distinct classes of motor neurons. $Pax6^+$ progenitors give rise to somatic motor neurons whereas $Nkx2.2^+$ progenitors generate visceral motor neurons (Ericson et al. 1997). As these two progenitor populations leave the cell cycle they express different homeodomain proteins that characterize distinct motor neuron subtypes (Tsuchida et al., 1994; Varela-Echavarria et al., 1996; Ericson et al., 1997; Pattyn et al. 1997). The activity of Pax6 is necessary for the differentiation of somatic motor neurons within the hindbrain (Ericson et al., 1997; Osumi et al., 1997) but it appears that its function is indirect, being required to repress the expression of Nkx2.2 (Ericson et al., 1997).

The dispensibility of Pax6 for somatic motor neuron generation implies the existence of additional genes that determine somatic motor neuron identity. Moreover, the late commitment: of progenitors to a somatic motor neuron fate suggests that the onset of expression of such genes occurs only during the final division cycle of motor neuron progenitors. To identify such determinants a screen for genes expressed by somatic motor neuron progenitors was performed and described, here is the characterization of a novel homeobox gene, MNR2.

MNR2 is expressed selectively by $Pax6^+$ motor neuron progenitors and persists transiently in post-mitotic somatic motor neurons. The ectopic expression of MNR2 in vivo is sufficient to activate a program of somatic motor neuron differentiation characterized by the expression of several homeodomain proteins and Choline Acetyltransferase (ChAT), by the autoactivation of MNR2 and by the extension of axons into ventral roots. This program of motor neuron differentiation is accompanied by the repression of spinal interneuron fates. Thus, the Shh-triggered differentiation of ventral progenitor cells into somatic motor neurons may be directed by the expression of a single homeodomain protein, MNR2.

Introduction

The ability of neurons to form selective neuronal circuits is a function of the molecular properties that they acquire at early stages of their differentiation. The molecular features that distinguish individual classes of neurons appear to control the pattern of axonal projections, the formation of target connections and the expression of specific chemical transmitters. The emergence of a coherent neuronal phenotype is a protracted process and is thought to involve progressive restrictions in the developmental potential of both neural progenitor cells and post-mitotic neurons (Cepko 1999; Edlund and Jessell, 1999). In the peripheral nervous system, convergent programs of transcription factor expression have been suggested to coordinate pan-neuronal properties with more specific aspects of neuronal subtype identity, notably neurotransmitter synthesis and trophic factor sensitivity (Lo et al., 1998, 1999; Pattyn et al., 1999; Goridis and Brunet, 1999).

When and how neuronal subclasses in the central nervous system acquire their specialized functional properties is less well understood. Studies of the differentiation of spinal motor neurons (MNs) have provided some insight into the steps that confer neuronal subtype identity within the central nervous system. Physiological and anatomical studies have revealed that spinal MNs exhibit several levels of organization and function (Landmesser, 1978 a, b) and these have a molecular correlate in the selective patterns of expression of different families of transcription factors (Tanabe and Jessell, 1996; Goulding, 1998). Members of the LIM homeodomain (LIM-HD) protein family define aspects of the generic and columnar identities of spinal MNs (Ericson et al., 1992; 1996; Tsuchida et al., 1994; Sharma et al., 1998). In addition, many of the MN pools that innervate individual muscles in the limb can be defined by the expression of ETS domain proteins (Lin et al., 1998). The analysis of neuronal fate changes that result from the misexpression or inactivation of certain of these nuclear factors has lent support to the idea that they have critical roles in the specification of MN identity (Tanabe et al., 1998: Sharma et al., 1998; see Appel, 1999).

Some of the earlier events that specify the differentiation of neural progenitors into MNs have also been defined. The differentiation of MNs is initiated when progenitor cells located in the ventral half of the neural tube acquire distinct identities in response to the graded signaling activity of Sonic hedgehog (Shh) (Ericson et al., 1996, 1997a,b; Briscoe et al., 1999). The final division of MN progenitors in chick is marked by the onset of expression of two homeodomain proteins, MNR2 and Lim3 (Lhx3) which appear to have distinct roles in MN differentiation (Ericson et al., 1997a; Tanabe et al., 1998; Sharma et al., 1998). MNR2 expression is restricted to MN progenitors whereas Lim3 is expressed by progenitor cells that give rise to an adjacent population of V2 interneurons (Ericson et al., 1997a; Tanabe et al., 1998). In chick, the ectopic expression of MNR2 is sufficient to direct the differentiation of neural cells into MNs and to suppress V2 interneuron generation (Tanabe et al., 1998). In contrast, ectopic expression of Lim3 alone appears to promote the generation of V2 interneurons (Tanabe et al., 1998). These results suggest that MNR2 has a role in specifying whether ventral progenitors that express Lim3 generate MNs rather than V2 neurons.

The function of many of the other transcription factors whose expression is restricted to MNs has not yet been addressed. Amongst these, the homeobox gene Hb9 (Harrison et al., 1994; Ross et al., 1998) is a selective marker of MNs in the developing spinal cord (Pfaff et al., 1996; Saha et al., 1997; Tanabe et al., 1998). Strikingly, HB9 possesses a homeodomain virtually identical to that of MNR2. Moreover, the ectopic expression of HB9 in chick has been shown to mimic the MN-inducing and V2 interneuron repressive activities of MNR2 (Tanabe et al., 1998; unpublished data). In contrast to MNR2, however, the expression of HB9 in chick is excluded from ventral progenitor cells and is restricted to post-mitotic MNs (Tanabe et al., 1998), suggesting that it has a later role in the differentiation of post-mitotic MNs. Further insight into the developmental roles of MNR2 and HB9, however, requires an analysis of MN differentiation in embryos that lack the function of these homeodomain proteins.

To begin to address this issue we have examined MN development in mice in which the Hb9 gene has been inactivated by targeted mutation. In mice lacking Hb9 function, MNs are generated on schedule and in normal numbers. However, soon after MNs have left the cell cycle, there is a dramatic change in the program of MN differentiation. Most strikingly, MNs transiently express transcription factors normally characteristic of V2 interneurons. In addition, and perhaps as a consequence, the transcription factor codes that define the columnar and pool identities of spinal MNs are markedly disrupted. These defects in the transcription factor profile of MNs are accompanied by abnormal MN migratory patterns, by errors in motor axon projections and by defects in the innervation of certain target muscles. Together, these results provide evidence that HB9 has a critical role in the consolidation of MN identity, in particular in repressing the expression of V2 interneuron character.

The initial stages of pancreatic development occur early during mammalian embryogenesis (Wessells et al. 1981) but the genes governing this process remain largely unknown. The homeodomain protein IPF1/PDX1 is expressed in the developing pancreatic anlagen from the ~10 somite stage (Ohlsson et al. 1993; Ahlgren et al. 1996) and mutations in the IPF1/PDX1 gene prevent the development of the pancreas (Ahlgren et al. 1996; Jonsson et al. 1994; Offield et al. 1996; Harrison et al. 1994). However, the initial stages of pancreatic development still occur in Ipf1/Pdx1 deficient mice (Ahlgren et al. 1993). Hb96 is a homeobox gene that in humans has been linked to dominant inherited sacral agenesis (Ross et al. 1998) and we show here that HB9 is expressed at early stages of mouse pancreatic development and later in differentiated -cells. Hb9 has an essential function in the initial stages of pancreatic development. In absence of Hb9 expression, the dorsal region of the gut epithelium fails to initiate a pancreatic differentiation program. In contrast, the ventral pancreatic endoderm develops but exhibits a later and more subtle perturbation in -cell differentiation and in islet cell organisation. Thus, dorsally Hb9 is required for specifying the gut epithelium to a pancreatic fate and ventrally for ensuring proper -cell differentiation.

SUMMARY OF THE INVENTION

This invention provides an isolated nucleic molecule encoding a motor neuron restricted pattern, MNR2, protein.

This invention provides a vector which comprises the isolated nucleic acid encoding a motor neuron restricted pattern, MNR2, protein.

This invention provides a host cell containing the vector which comprises the isolated nucleic acid encoding a motor neuron restricted pattern, MNR2, protein.

This invention provides a method of producing a polypeptide having the biological activity of a mammalian MNR2 which comprises growing host cells selected from a group consisting of bacterial, plant, insect or mammalian cell, under suitable conditions permitting production of the polypeptide.

This invention provides an isolated nucleic acid molecule of at least 15 contiguous nucleotides capable of specifically hybridizing with a unique sequence included within the sequence of the nucleic acid molecule encoding a motor neuron restricted pattern, MNR2, protein.

This invention provides an antisense oligonucleotide having a nucleic acid sequence capable of specifically hybridizing to an mRNA molecule encoding a MNR2 protein.

This invention provides a monoclonal antibody directed to an epitope of an MNR2 protein.

This invention provides a purified MNR2 protein.

This invention provides a method of inducing differentiation somatic motor neurons which comprises expressing MNR2 protein in neural progenitor cells.

This invention provides a transgenic nonhuman mammal which comprises an isolated nucleic acid encoding a motor neuron restricted pattern, MNR2, protein, is a DNA molecule.

This invention provides a method of determining physiological effects of expressing varying levels of MNR2 protein in a transgenic nonhuman mammal which comprises producing a panel of transgenic nonhuman animals, each a transgenic nonhuman mammal, each nonhuman mammal expressing a different amount of MNR2 protein.

This invention provides a method of producing an isolated purified MNR2 protein which comprises: a) inserting a nucleic acid molecule encoding a MNR2 protein into a suitable vector; b) introducing the resulting vector into a suitable host cell; c) selecting the introduced host cell for the expression of the MNR2 protein; d) culturing the selected cell to produce the MNR2 protein; and e) recovering the MNR2 protein produced.

This invention provides a method of inducing differentiation of somatic motor neurons in a subject comprising administering to the subject the purified MNR2 protein in an amount effective to induce differentiation of somatic motor neurons in the subject.

This invention provides a pharmaceutical composition comprising a purified MNR2 protein and a pharmaceutically acceptable carrier.

This invention provides a method for treating a subject afflicted with an abnormality associated with a lack of one or more normally functioning motor neurons which comprises introducing an amount of a pharmaceutical composition comprising a purified MNR2 protein and a pharmaceutically acceptable carrier effective to generate somatic motor neurons from undifferentiated motor neuron precursor cells in the subject, thereby treating the subject afflicted with the abnormality associated with the lack of one or more normally functioning motor neurons.

This invention provides a method of treating a subject afflicted with a neurodegenerative disease which comprises introducing an amount of a pharmaceutical composition which comprises a purified MNR2 protein and a pharmaceutically acceptable carrier effective to generate somatic motor neurons from undifferentiated precursor motor neuron cells in the subject, thereby treating the subject afflicted with the neurodegenerative disease.

This invention provides for a method of treating a subject afflicted with an acute nervous system injury which comprises introducing an amount of a pharmaceutical composition which comprises a purified MNR2 protein and a pharmaceutically acceptable carrier effective to generate motor neurons from undifferentiated precursor motor neuron cells in a subject, thereby treating the subject afflicted with the acute nervous system injury.

This invention provides for a method of treating a subject afflicted with an acute nervous system injury, wherein the acute nervous system injury is localized to a specific central axon which comprises surgical implantation of a pharmaceutical composition comprising a MNR2 protein and a pharmaceutically acceptable carrier effective to generate motor neurons from undifferentiated precursor motor neuron cells located proximal to the specific central axon, so as to alleviate the acute nervous system injury localized to a specific central axon, thereby treating the subject afflicted with the acute nervous system injury.

This invention provides a method for diagnosing a chronic neurodegenerative disease associated with the expression of a MNR2 protein in a sample from a subject which comprises: (a) obtaining DNA from the sample of the subject suffering from the chronic neurodegenerative disease; (b) performing a restriction digest of the DNA with a panel of restriction enzymes; (c) separating the resulting DNA fragments by size fractionation; (d) contacting the resulting DNA fragments with a nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence and labeled with a detectable marker; (e) detecting labeled bands which have hybridized to the nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence to create a unique band pattern specific to the DNA of subjects suffering from the chronic neurodegenerative disease; (f) preparing DNA obtained from a sample of a subject for diagnosis by steps (a–e); and (g) comparing the detected band pattern specific to the DNA obtained from a sample of subjects suffering from the chronic neurodegenerative disease from step (e) and the DNA obtained from a sample of the subject for diagnosis from step (f) to determine whether the patterns are the same or different and to diagnose thereby predisposition to the chronic neurodegenerative disease if the patterns are the same.

This invention provides a method for diagnosing a chronic neurodegenerative disease associated with the expression of a MNR2 protein in a sample from a subject which comprises: (a) obtaining RNA from the sample of the subject suffering from chronic neurodegenerative disease; (b) separating the RNA sample by size fractionation; (c) contacting the resulting RNA species with a nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence and labeled with a detectable marker; (d) detecting labeled bands which have hybridized to the RNA species to create a unique band pattern specific to the RNA of subjects suffering from the chronic neurodegenerative disease; (e) preparing RNA obtained from a sample of a subject for diagnosis by steps (a–d); and (f) comparing the detected band pattern specific to the RNA obtained from a sample of subjects suffering from the chronic neurodegenerative disease from step (d) and the RNA obtained from a sample of the subject for diagnosis from step (f) to determine whether the patterns are the same or different and to diagnose thereby predisposition to the chronic neurodegenerative disease if the patterns are the same.

This invention provides a functionally equivalent analog of MNR2 that induces MNR2 differentiation of neural progenitor cells.

This invention provides a functionally equivalent analog of MNR2 that prevents MNR2 differentiation of neural progenitor cells.

This invention provides a method of treating a subject afflicted with a neuromuscular disease which comprises introducing an amount of a pharmaceutical composition comprising a purified MNR2 protein and a pharmaceutically acceptable carrier effective to activate acetylcholine to activate muscle cells.

This invention provides an isolated nucleic molecule encoding a homeobox, HB9, protein.

This invention provides a vector which comprises the isolated nucleic acid encoding a homeobox, HB9, protein.

This invention provides a host cell containing the vector which comprises the isolated nucleic acid encoding a homeobox, HB9, protein.

This invention provides a method of producing a polypeptide having the biological activity of a mammalian HB9 which comprises growing host cells selected from a group consisting of bacterial, plant, insect or mammalian cell, under suitable conditions permitting production of the polypeptide.

This invention provides an isolated nucleic acid molecule of at least 15 contiguous nucleotides capable of specifically hybridizing with a unique sequence included within the sequence of the nucleic acid molecule encoding a homeobox, HB9, protein.

This invention provides an antisense oligonucleotide having a nucleic acid sequence capable of specifically hybridizing to an mRNA molecule encoding a HB9 protein.

This invention provides a monoclonal antibody directed to an epitope of an HB9 protein.

This invention provides a purified HB9 protein.

This invention provides a method of inducing differentiation somatic motor neurons which comprises expressing HB9 protein in neural progenitor cells.

This invention provides a transgenic nonhuman mammal which comprises an isolated nucleic acid encoding a homeobox, HB9, protein, is a DNA molecule.

This invention provides a method of determining physiological effects of expressing varying levels of HB9 protein in a transgenic nonhuman mammal which comprises producing a panel of transgenic nonhuman animals, each a transgenic nonhuman mammal, each nonhuman mammal expressing a different amount of HB9 protein.

This invention provides a method of producing an isolated purified HB9 protein which comprises: a) inserting a nucleic acid molecule encoding a HB9 protein into a suitable vector; b) introducing the resulting vector into a suitable host cell; c) selecting the introduced host cell for the expression of the HB9 protein; d) culturing the selected cell to produce the HB9 protein; and e) recovering the HB9 protein produced.

This invention provides a method of inducing differentiation of somatic motor neurons in a subject comprising administering to the subject the purified HB9 protein in an amount effective to induce differentiation of somatic motor neurons in the subject.

This invention provides a pharmaceutical composition comprising a purified HB9 protein and a pharmaceutically acceptable carrier.

This invention provides a method for treating a subject afflicted with an abnormality associated with a lack of one or more normally functioning motor neurons which comprises introducing an amount of a pharmaceutical composition comprising a purified HB9 protein and a pharmaceutically acceptable carrier effective to generate somatic motor neurons from undifferentiated motor neuron precursor cells in the subject, thereby treating the subject afflicted with the abnormality associated with the lack of one or more normally functioning motor neurons.

This invention provides a method of treating a subject afflicted with a neurodegenerative disease which comprises introducing an amount of a pharmaceutical composition which comprises a purified HB9 protein and a pharmaceutically acceptable carrier effective to generate somatic motor neurons from undifferentiated precursor motor neuron cells in the subject, thereby treating the subject afflicted with the neurodegenerative disease.

This invention provides for a method of treating a subject afflicted with an acute nervous system injury which comprises introducing an amount of a pharmaceutical composition which comprises a purified HB9 protein and a pharmaceutically acceptable carrier effective to generate motor neurons from undifferentiated precursor motor neuron cells in a subject, thereby treating the subject afflicted with the acute nervous system injury.

This invention provides for a method of treating a subject afflicted with an acute nervous system injury, wherein the acute nervous system injury is localized to a specific central axon which comprises surgical implantation of a pharmaceutical composition comprising a HB9 protein and a pharmaceutically acceptable carrier effective to generate motor neurons from undifferentiated precursor motor neuron cells located proximal to the specific central axon, so as to alleviate the acute nervous system injury localized to a specific central axon, thereby treating the subject afflicted with the acute nervous system injury.

This invention provides a method for diagnosing a chronic neurodegenerative disease associated with the expression of a HB9 protein in a sample from a subject which comprises: (a) obtaining DNA from the sample of the subject suffering from the chronic neurodegenerative disease; (b) performing a restriction digest of the DNA with a panel of restriction enzymes; (c) separating the resulting DNA fragments by size fractionation; (d) contacting the resulting DNA fragments with a nucleic acid probe capable of specifically hybridizing with a unique sequence included within the sequence of a nucleic acid molecule encoding a HB9 protein, wherein the sequence of a nucleic acid molecule encoding a HB9 protein is linked at a specific break point to a specified nucleic acid sequence and labeled with a detectable marker; (e) detecting labeled bands which have hybridized to the nucleic acid probe capable of specifically hybridizing with a unique sequence included within the sequence of a nucleic acid molecule encoding a HB9 protein, wherein the sequence of a nucleic acid molecule encoding a HB9 protein is linked at a specific break point to a specified nucleic acid sequence to create a unique band pattern specific to the DNA of subjects suffering from the chronic neurodegenerative disease; (f) preparing DNA obtained from a sample of a subject for diagnosis by steps (a–e); and (g) comparing the detected band pattern specific to the DNA obtained from a sample of subjects suffering from the chronic neurodegenerative disease from step (e) and the DNA obtained from a sample of the subject for diagnosis from step (f) to determine whether the patterns are the same or different and to diagnose thereby predisposition to the chronic neurodegenerative disease if the patterns are the same.

This invention provides a method for diagnosing a chronic neurodegenerative disease associated with the expression of a HB9 protein in a sample from a subject which comprises: (a) obtaining RNA from the sample of the subject suffering from chronic neurodegenerative disease; (b) separating the RNA sample by size fractionation; (c) contacting the resulting RNA species with a nucleic acid probe capable of specifically hybridizing with a unique sequence included within the sequence of a nucleic acid molecule encoding a HB9 protein, wherein the sequence of a nucleic acid molecule encoding a HB9 protein is linked at a specific break point to a specified nucleic acid sequence and labeled with a detectable marker; (d) detecting labeled bands which have hybridized to the RNA species to create a unique band pattern specific to the RNA of subjects suffering from the chronic neurodegenerative disease; (e) preparing RNA obtained from a sample of a subject for diagnosis by steps (a–d); and (f) comparing the detected band pattern specific to the RNA obtained from a sample of subjects suffering from the chronic neurodegenerative disease from step (d) and the RNA obtained from a sample of the subject for diagnosis from step (f) to determine whether the patterns are the same or different and to diagnose thereby predisposition to the chronic neurodegenerative disease it the patterns are the same.

This invention provides a functionally equivalent analog of HB9 that induces HB9 differentiation of neural progenitor cells.

This invention provides a functionally equivalent analog of HB9 that prevents HB9 differentiation of neural progenitor cells.

This invention provides a method of treating a subject afflicted with a neuromuscular disease which comprises introducing an amount of a pharmaceutical composition comprising a purified HB9 protein and a pharmaceutically acceptable carrier effective to activate acetylcholine to activate muscle cells.

BRIEF DESCRIPTION OF THE FIGURES

FIGS. 1A–H.
Isolation and Characterization of MNR2.
FIG. 1A.
Hybridization analysis of cells isolated from [i] explants grown alone or with Shh. Left hand panels show cells isolated from explants grown with 2 nM Shh and right hand panels show cells isolated from explants grown without Shh. Top panels: ethidium labeling of PCR-amplified single cell-derived cDNAs. Lower panels: specific PCR-amplified transcripts in individual cells. Red circle indicates a motor neuron defined by Isl1, HB9 and Isl2 expression. Gray circles indicate interneurons, defined by Lim2 expression.

FIG. 1B.
Sequence similarity of the chick and human HB9 proteins (black line) and chick MNR2 and HB9 proteins (red line). Conservation is indicated by higher similarity scores, using the PileUp and PlotSimilarity programs, Wisconsin Package 9.1, Genetics Computer Group. Chick MNR2 is 56% identical to chick H9. Chick HB9 is 77% identical to human HB9. HD: homeodomain.

FIGS. 1C and 1D.
MNR2 expression in sections of cervical spinal cord of stage 12 FIG. 1C. and stage 16 FIG. 1D. embryos.

FIG. 1E.
MNR2 expression in a stage 20 embryo. White circle shows position of the otic vesicle. Arrow indicates expression of MNR2 in abducens motor neurons.

FIGS. 1F–H.
Induction of MNR2 expression by Shh. [i] explants grown alone for 24 h do not give rise to MNR2$^+$ cells FIG. 1F. [i] explants grown with Shh (4 nM) for 24 h contain many MNR2$^+$ cells FIG. 1G not all of which express Isl1/2 FIG. 1H. Images representative of 4 explants.

FIGS. 2A–K.
Expression of MNR2 Precedes that of Other Homeodomain Proteins.

FIG. 2A.
MNR2 expression (red cells) in the ventral neural tube of a stage 18 embryo labeled with a pulse of BrdU (green cells) Many cells coexpress MNR2 and BrdU (yellow cells).

FIG. 2B.
Adjacent section to FIG. 2A. showing that Isl1/2$^+$ cells (red cells) do not coexpress BrdU (green cells).

FIG. 2C.
Coexpression of MNR2 and MPM2 (Westendorf et al., 1994) in a cell (yellow; arrow) in the ventral neural tube. Approximately one MNR2$^+$, MPM2$^+$ cell was detected/10 μm section, analysis of 300 MNR2$^+$ cells in 30 sections.

FIG. 2D
Coexpression of MNR2 (red) and Pax6 (green) by ventral cells in stage 20 spinal cord.

FIG. 2E.
MNR2$^+$ cells (red) located dorsal to Nkx2.2+ cells (green) in stage 20 chick spinal cord.

FIG. 2F.
MNR2 expression (red) in the caudal hindbrain (r7/r8) is restricted to dorsal hypoglossal (somatic) motor neurons. Ventral vagal (visceral) motor neurons express Isl1 (green) but not MNR2. MNR2 is absent from other cranial motor neurons and from thoracic visceral motor neurons. MNR2 expression is excluded from oculomotor and trochlear motor neurons, consistent with their expression of the visceral motor neuron markers Phox2a and Phox2b (Pattyn et al., 1997).

FIGS. 2C–J.
Expression of MNR2 (red) and other homeodomain protein markers (green) of spinal motor neurons in stage 20 embryos. Arrow in FIG. 2G. indicates dorsal Isl1$^+$ (D2) neurons. Lim3$^+$ cells dorsal to MNR2$^+$ cells in FIG. 2J. are V2 neurons (arrow).

FIG. 2K.
Temporal sequence of homeodomain protein expression by somatic motor neuron progenitors and newly-differentiated somatic motor neurons. D2 and V2 neuron domains are shown. Dotted line indicates cell cycle exit.

FIGS. 3A–J.
MNR2 Induces Somatic Motor Neuron Transcription Factors.

FIG. 3A.
Sections of the spinal cord of an MNR2-infected embryo at stage 23. In this embryo, ectopic MNR2 expression is detected predominantly on the right side.

FIGS. 3B–E.
Ectopic expression of Isl1 FIG. 3B. Isl2 FIG. 3C. HB9 FIG. 3D. and Lim3 FIG. 3E. in an MNR2-infected embryo. Ectopic cells exhibit no dorsoventral (DV) restriction. The increase in the number of dorsal Isl1$^+$ cells FIG. 3B. is not caused by the precocious differentiation of D2 neurons (data not shown).

FIG. 3F
Detail of an MNR2-infected spinal cord showing that ectopic Isl1$^+$ cells coexpress MNR2. Similar findings were obtained for Isl2$^+$ and HB9$^+$ cells.

FIG. 3G.
Section through the spinal cord of an MNR2-infected embryo showing Pax7$^+$ dorsal progenitors (green). Ectopic MNR2 (red) does not repress Pax7 (green). Lateral MNR2$^+$, Pax7$^-$ cells are post-mitotic neurons. Arrowhead indicates DV boundary.

FIGS. 3H–J.
Induction of Isl1/2 in ventral progenitors by MNR2. [i] explants isolated from MNR2-infected embryos and grown in vitro for 24 h with 0.5 nM Shh contain many MNR2$^+$ cells FIG. 3H. Many of these cells express Isl1/2 FIG. 3I. [i] explants isolated from uninfected embryos and exposed to 0.5 nM Shh do not contain MNR2$^+$ cells FIG. 3J. and do not give rise to Isl1/2$^+$ neurons (data not shown) Similar results obtained in 4 explants.

FIGS. 4A–J.

Figure 8:
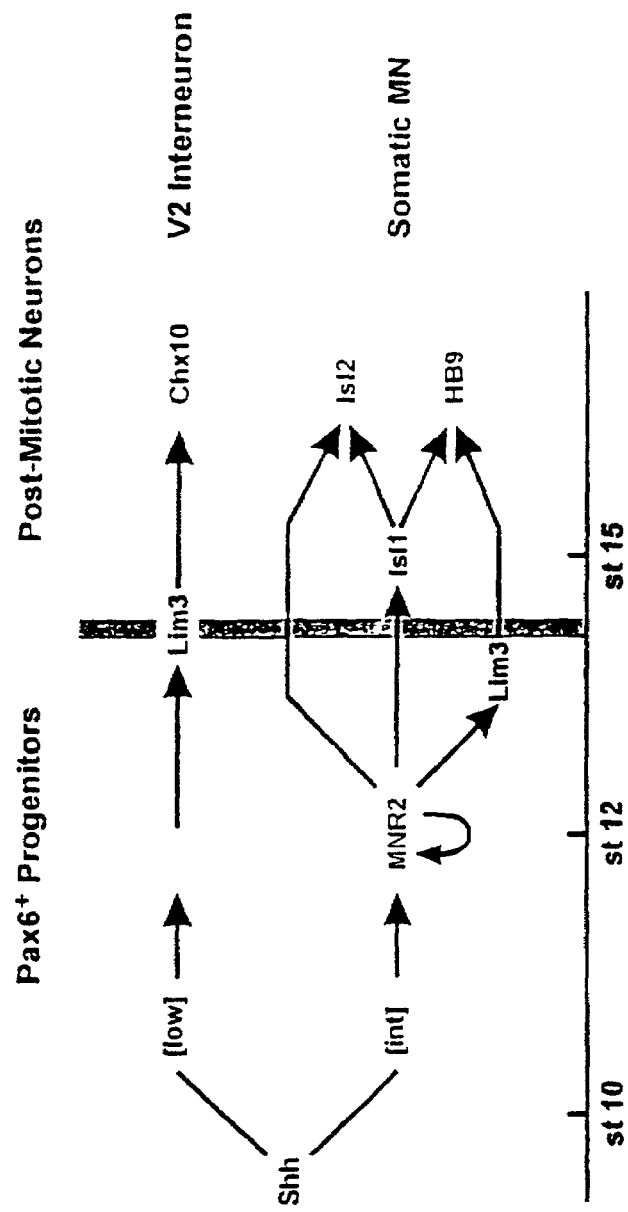

MNR2 Functions Within the Context of a General Neurogenic Program.

FIG. 4A.

Coexpression of MNR2 (red) and Cyn1 (green) in the spinal cord of an MNR2-infected embryo, analyzed at stage 21. Cyn1$^+$, MNR2$^+$ cells are restricted to the lateral margin of the spinal cord. MNR2 expression does not alter the number of Cyn1+ cells.

FIG. 4B.

Quantitative analysis of Cyn1 expression by ectopic MNR2$^+$ cells. Similar values were obtained from stages 20–23. Analysis derived from >300 MNR2$^+$ cells.

FIG. 4C.

Detail of the dorsal spinal cord of an MNR2-infected embryo. All ectopic Isl1/2$^+$ cells coexpress Cyn1 (green).

FIG. 4D.

MNR2-induced ectopic Isl1$^+$ cells coexpress Cyn1. Analysis of >200 ectopic Isl1$^+$ cells.

FIG. 4E.

Proportion of MNR2-induced ectopic Is12$^+$, HB9$^+$ and Lim3$^+$ cells that coexpress Isl1. All Isl2$^+$ and HB9$^+$ cells coexpress Isl1. Only 55% of ectopic Lim3$^+$ cells coexpress Isl1. Analysis of 77 Is12$^+$, 38 HB9$^+$ and 96 Lim3$^+$ cells.

FIG. 4F.

Many ectopic Lim3$^+$ cells (red) in MNR2-infected embryos are labeled (arrows) by a BrdU pulse (green).

FIG. 4G.

Detail showing that many MNR2-induced ectopic Lim3$^+$ cells (green) do not express Isl1 (red).

FIG. 4H.

Expression of homeodomain protein markers in ectopic MNR2$^+$, neurons (MNR2$^+$/Cyn1$^+$ cells). Analysis of 690 Isl1, 70 Isl2$^+$, 111 HB9$^+$ and 540 Lim3$^+$ cells. More than 2000 MNR2$^+$ cells analyzed from more than 40 MNR2-infected embryos.

FIG. 4I.

Misexpression of MNR2 in an embryo infected with a MNR2 3'Δ construct. Section labeled with a 5' coding probe.

FIG. 4J.

Activation of endogenous MNR2 in an MNR2-infected embryo revealed using a 3' non-coding probe. The endogenous MNR2 gene is activated both in neural and surrounding tissues.

FIGS. 5A–J.

MNR2 Induces Later Features of the Somatic Motor Neuron Phenotype.

FIGS. 5A–D.

ChAT expression in the spinal cord of uninfected FIG. 5A. and FIG. 5C. and MNR2-infected embryos FIGS. 5B. and D.

Ectopic clusters of ChAT$^+$ cells are detected in the dorsal spinal cord of MNR2-infected embryos (arrows in FIGS. 5B and D).

FIG. 5E.

Quantitation of ectopic dorsal ChAT$^+$ cell clusters in uninfected and MNR2-infected embryos. Number of ectopic dorsal ChAT$^+$ cell clusters detected in 70, 15 μm sections.

FIGS. 5F–H.

FITC-Dextran$^+$ (FITC-Dx) labeled neurons in the spinal cord of stage 25 embryos after application of FITC-Dx to the ventral roots. In uninfected embryos FIG. 5F., retrogradely labeled cells (green) are restricted to Isl1/2$^+$ motor neurons (red). In MNR2-infected embryos ectopic FITC-Dx$^+$ Isl1/2 are detected in the V1 and V2 neuron domain FIG. 5G. Ectopic FITC-Dx$^+$ neurons are also located in the dorsal spinal cord and coexpress Isl1/2 FIG. 5H and MNR2 FIG. 5I. The axons of these neurons project ventrally (arrows in FIG. 5I). Sensory axons in the dorsal root entry zone have also been labeled in some embryos (see FIG. 5I).

FIG. 5J.

Ectopic FITC-Dx$^+$ neurons in the dorsal spinal cord (DV boundary is shown by dotted line in FIG. 5H., analyzed in 80, 10 μm sections of uninfected and MNR2-infected embryos. Ectopic FITC-Dx neurons in the V1 and V2 neuron domain are not plotted in FIG. 5J.

FIGS. 6A–P.

Cooperation of MNR2 and Isl1 in the Induction of Somatic Motor Neurons.

FIGS. 6A–E.

Sections of the spinal cord of an embryo infected with Isl1 virus and analyzed at stage 20. Despite ectopic expression of Isl1 FIG. 6A., no ectopic MNR2$^+$, FIG. 6B., Lim3$^+$ FIG. 6C., Isl2$^+$ FIG. 6D. or HB9$^+$ FIG. 6E. cells are detected. Images representative of six infected embryos. FIGS. 6F–H. Isl1, Isl2 and HB9 expression in an MNR2-infected embryo analyzed at stage 20. Most Isl1$^+$ neurons are focused on the D2 neuron domain although more ventrally located neurons are also detected FIG. 6F. All Isl2$^+$ cells FIG. 6G. coexpress Isl1 FIG. 6H. (see panel FIG. 6P. for quantitation).

FIGS. 6I, 6J.

HB9 expression in a stage 20 MNR2-infected embryo. All ectopic HB9$^+$ cells FIG. 6I. coexpress Isl1 FIG. 6J. See panel FIG. 6P. for quantitation.

FIGS. 6K–M.

Isl2 and HB9 expression in the spinal cord of an embryo coinfected with MNR2 and Isl1 viruses, analyzed at stage 20.

FIG. 6K.

Many ectopic MNR2$^+$ cells (red) coexpress Isl1 (green) and thus appear as yellow cells.

FIG. 6L.

Ectopic expression of Isl2 in the spinal cord of an embryo coinfected with MNR2 and Isl1 viruses, analyzed at stage 20.

FIG. 6M.

Ectopic expression of HB9 in the spinal cord of an embryo coinfected with MNR2 and Isl1 viruses, analyzed at stage 20.

FIG. 6N.

Expression of Lim3, Isl2 and HB9 in ectopic MNR2$^+$, Isl1$^+$ cells. Analysis of more than 300 cells for each marker, from four infected embryos.

FIGS. 6O, and P.

Distribution of ectopic Isl1$^+$, Isl2$^+$ and HB9$^+$, cells along the DV axis of the spinal cord of uninfected, MNR2-infected, and MNR2/Isl1-coinfected embryos, analyzed at stage 20. Diagram in FIG. 6O. shows the DV divisions (bins A–F) of the spinal cord used to compile histograms shown in FIG. 6P. Bins B and C normally contain Isl1$^+$ D2 neurons and bin F contains V2 neurons. Values indicate number of ectopic cells, mean ±SEM >300 cells in 30 sections for each marker.

FIG. 7.

Cooperation of Lim3 and Isl1 as Mediators of MNR2 Activity and Mimicry by HB9.

FIG. 7A.

Ectopic expression of Lim3 in the spinal cord of a Lim3-infected embryo, analyzed at stage 23.

FIG. 7B.

Absence of ectopic MNR2+ cells in the spinal cord of a Lim3-infected embryo. Analysis of more than 4000 ectopic Lim3+ cells.

FIG. 7C.

Absence of ectopic Isl2+ cells in the spinal cord of a Lim3-infected embryo. Analysis of more than 5000 ectopic Lim3+ cells.

FIG. 7D.

Low incidence of ectopic expression of HB9 (green) in the spinal cord of a Lim3-infected embryo. All ectopic HB9 cells coexpress Isl1 (red). Analysis of more than 5000 ectopic Lim3+ cells.

FIG. 7E.

Quantitation of ectopic Isl1+, Isl2+ and HB9+ cells in the dorsal spinal cord of a Lim3-infected embryo. Analysis of 300–600 Lim3+ cells.

FIG. 7F.

Ectopic expression of Chx10 (green) in the spinal cord of a Lim3-infected embryo. All ectopic Chx10+ cells coexpress Lim3 (red) and thus appear as yellow cells.

FIG. 7G.

Same image as in FIG. 7F, showing that ectopic Chx10+ cells (green) are located both dorsal and ventral (arrowheads) to the position of Isl+ motor neurons.

FIG. 7H.

Coexpression of Isl1 (red) and Lim3 (green) in the spinal cord of a Lim3/Isl1 coinfected embryo.

FIG. 7I.

Isl2 expression is not detected in the spinal cord of a Lim3/Isl1 coinfected embryo.

FIG. 7J.

A high incidence of ectopic HB9 expression is detected in the spinal cord of a Lim3/Isl1 coinfected embryo.

FIG. 7K.

Ectopic Isl2 and HB9 expression in the dorsal spinal cord of Lim3/Isl1 infected embryos. Analysis of 300–600 neurons from six infected embryos.

FIG. 7L.

Expression of HB9 in the spinal cord of an HB9-infected embryo analyzed at stage 23.

FIG. 7M.

Ectopic dorsal expression of Isl2 in the spinal cord of an HB9-infected embryo. Analysis from >10 infected embryos.

FIG. 7N.

Ectopic dorsal expression of Lim3 in the spinal cord of an HB9-infected embryo.

FIG. 8.

Role of MNR2 in the Shh-Induced Pathway of Somatic Motor Neuron and V2 Interneuron Generation.

In this model, homeodomain proteins (MNR2, Isl2, HB9) shown in red are restricted to the somatic motor neuron lineage and those (Lim 3, Chx10, V2 Interneuron) in blue to the V2 interneuron lineage. Vertical gray bar indicates time of exit from the cell cycle. The diagram indicates the subordinate activities of Lim3 and Isl1 in the activation of HB9, the requirement for Isl1 in the induction of HB9 and Isl2, and the autoactivation of MNR2. In the absence of MNR2 activity, Lim3 is sufficient to induce Chx10. For details see the text.

FIG. 9

Suppression of Spinal Interneuron Fates by MNR2.

FIG. 9A.

Schematic diagram of the position of D1 (LH2+), D2 (Isl1+), V1 (En1+) and V2 (Chx10+) interneurons in the spinal cord of a stage 20–22 chick embryo.

FIG. 9B.

Section through the spinal cord of a stage 22 MNR2-infected embryo showing the asymmetric distribution of ectopic MNR2+ cells, which are restricted almost exclusively to the right half of the spinal cord of this embryo.

FIGS. 9C–N.

Sections through the same embryo shown in FIG. 9B. double or triple-labeled to reveal ectopic Isl1+ neurons and the expression of D1, D2, V1 and V2 interneuron markers.

FIGS. 9C–E.

Shows the reduction (approximately 75%) in LH2 expression in the right half of the infected embryo.

FIGS. 9F–H.

Shows the reduction in Brn 3.0 expression (88±4%, n=4 sections) in the right half of the infected spinal cord.

FIGS. 9I–K.

Shows the reduction in En1 expression (46±5%; n=10 sections) in the right half of the infected spinal cord.

FIGS. 9L–N.

Shows the reduction in Chx10 expression (89±3%, n=9 sections) in the right half of the infected spinal cord. A similar repression of interneuron marker expression was detected in six other MNR2-infected embryos.

FIG. 10 cMNR2 Protein and the Predicted Amino Acid Sequence (SEQ ID NO: 1).

FIG. 11 cMNR2 DNA Nucleotides 1-1736. (SEQ ID NO: 2).

FIG. 12 cHB9 Protein and the Predicted Amino Acid Sequence (SEQ ID NO: 3).

FIG. 13 cHB9 DNA Nucleotides 1-1534. (SEQ ID NO: 4).

FIG. 14. Early Expression of HB9 by Developing Motor Neurons (A–D) Comparison of the expression of HB9 (red) and Lim3 (Lhx3) (green) in developing motor neurons at caudal cervical levels of e9.5 to e10.0 mouse embryos. Percentage numbers in each panel indicate the approximate fraction of motor neurons detected at the time of analysis, compared to the total number of motor neurons generated by e11.0 (see FIG. 3A). (A) At e9.5 (10–25% motor neuron generation), HB9 and Lim3 are coexpressed by most labeled cells although occasional Lim3+/HB9− cells are detected. (B, C) At slightly older ages (e9.75: 30–60% motor neuron generation), many medially located Lim3+/HB9− cells are detected and most double-labelled cells are confined to the lateral margins of the ventral spinal cord. (D) A similar profile is observed near the end of the period of motor neuron generation. The notochord is also labelled at these developmental stages.

(E–H) Comparison of expression of HB9 (red) and Isl1 (green) in developing motor neurons located at caudal cervical levels of e9.5 to e10.0 mouse embryos. (E). In e9.5 embryos (10–15% motor neuron generation), HB9 and Isl1 are coexpressed by most cells, although occasional HB9+/Isl1− cells are detected (arrows). (F, G) At slightly older stages (e9.75: 50–60% motor neuron generation) HB9 and Isl1 are coexpressed by virtually all cells in the ventral spinal cord. Note the expression of Isl1 but not of HB9 in sensory neurons in the dorsal root ganglia in (G). A similar profile is observed near the completion (85%) of motor neuron generation (H)

(I–L) Comparison of HB9 and MPM2 expression in developing motor neurons located at caudal cervical levels of e9.5 to e10.0 mouse embryos. (I). In e9.5 embryos (10–15% motor neuron generation), 10% of medially located MPM2+ cells express HB9 (arrow) although many ventral MPM2+ cells within the domain of motor neuron generation lack HB9 expression. (J, K) At slightly older stages (e9.75) (25–60% motor neuron generation) only 3% of MPM2 cells express HB9. Near the completion of motor neuron generation (>60% motor neuron generation) no MPM2+ cells coexpressed HB9, although many MPM2+, Lim3+ cells were detected (not shown). MPM2 analysis was based on at least 6 embryos examined over the period e9.5 to e10.0. (M) BrdU expression in many Lim3+ cells in the ventral domain of motor neuron generation, assayed during the peak period (60%) of motor neuron genesis. (N–P) Sections through e9.75 and e10.0 embryos pulse-labeled with BrdU in vivo for 2 h. At early stages of motor neuron genesis a few BrdU+/HB9+ cells are detected (N) but during the peak (O) and late (P) periods of motor neuron genesis, the number of BrdU+/HB9+ cells drops dramatically. BrdU analysis was performed in at least 6 embryos.

(Q) The position of generation of MNs and V2 interneurons. (R, S) Diagrams indicating the temporal profile of expression of HB9 in the early differentiation of mouse (R) and chick (S) spinal MNs, assessed by expression of homeodomain transcription factors. The sequential stages in the conversion of MN progenitors into post-mitotic MNs in chick are based on the data of Tanabe et al., 1998. Dashed vertical line indicates approximate time of cell cycle exit.

FIG. 15. Inactivation of Hb9 by Homologous Recombination.

(A) Diagrams show strategy for homologous recombination at the Hb9 locus in ES cells to generate a disrupted allele of Hb9 and the transgenic construct used to define a motor neuron regulatory region in the Hb9 locus. A 9 kb NotI fragment comprising the 5' upstream region of the Hb9 gene and sequence from the first exon (blue) of Hb9 was used to generate a transgenic construct. To generate a disrupted Hb9 allele, targeting cassettes were integrated into the NotI site of the first of three exons of the Hb9 gene (data not shown). A 6 kB 5' region (Sse83871-NotI) and a 3 kB 3' region (NotI-XbaI) were used to generate the basic targeting vector into which the targeting cassettes (green) were integrated. The probe to screen ES cells for the detection of homologous recombination was a 1 kB XbaI-XhoI (grey bar) fragment located 3' to the region used for the generation of the targeting construct.

(B) Targeting cassettes used for the generation of transgenic mice (i: IRES-nlslacZ) and generation of Hb9 alleles by homologous recombination in ES cells (ii–iv: ii: IRES-nlslacZ; iii: IRES-taulacZ; iv: IRES-taumyc). For homologous recombination, a PGK-NEO cassette flanked by loxP sites was inserted 3' to a SalI site. Right: Representative Southern blot of $Hb9^{nls-lacZ}$ genomic DNA derived from $Hb9^{nlslacZ/+}$ and embryos (6 kB mutant band, 20 kB wild type band; lines to the left indicate molecular weight standards; SalI/XhoI digest). Similar diagnostic blots were obtained from the other two targeted alleles (available on request).

(C–F) Analysis of wholemount embryos stained for –Galactosidase (-Gal) activity.

(C) e10 transgenic embryo (TgN(Hb9)SAX16), labeled for -Gal expression.

(D) e11.5 $Hb9^{nlslacZ/+}$ embryo. The staining in the developing limbs corresponds to the region of the zone of polarizing activity (zpa).

(E, F) -Gal staining of e11.5 $Hb9^{taulacZ/+}$ (E) and compound mutant $Hb9^{taulacZ/taumyc}$ (F) embryos. In the presence of one allele of tau-lacZ the staining intensity in the compound homozygote is five fold higher than in the heterozygote. Embryos were processed for the same incubation time.

(G–I) Expression of HB9 in the spinal cord of e10.5 wild type embryos (G). Coincidence of expression of HB9 protein (green) and nls-lacZ (-Gal red) in e10.5 $Hb9^{nlslacZ/+}$ spinal cord (H). Absence of HB9 protein in the spinal cord of e10.5 $Hb9^{nlslacZ/nlslacZ}$ embryos (I).

FIG. 16. Cell Migration Defects in Hb9 Mutant Embryos.

(A) Analysis of number of -Gal labeled cells in brachial spinal cord (cervical 7/8) at different developmental stages (e10, e10.5, e12.5 and e13.5) in $Hb9^{nlslacZ/+}$ (solid line), and $Hb9^{nlslacZ/nlslacZ}$ (dashed line) embryos.

(B–D) -Gal labeled neurons in $Hb9^{nlslacZ/nlslacZ}$ embryos are located adjacent to the spinal cord within ventral roots.

(B) Whole mount -Gal staining of e10.5 lumbar spinal cord showing extraspinal -Gal neurons.

(C) Extraspinal -Gal neurons (green) in an e12.5 embryo coexpress Isl1/2 (red).

(D) Extraspinal -Gal cells (red) in an e12.5 embryo (arrow) do not express the sensory neuron marker Brn3.0. The position of the dorsal root ganglion (DRG) is shown.

(E–J) Organization of -Gal labeled cells in the CNS, visualized in whole mount preparations of e17.5 $Hb9^{nlslacZ/+}$ (E, G, I) and $Hb9^{nlslacZ/nlslacZ}$ (F, H, J) embryos.

(E, F) Lateral view of caudal hindbrain and cervical level spinal cord. Arrows point to rostrocaudal level of hypoglossal MNs. Note the clustering of the -Gal labeled cells in the hypoglossal nucleus in heterozygous embryos but the scattered organization of -Gal labeled cells along both the dorsoventral and rostrocaudal axes of homozygous $Hb9^{nlslacZ}$ embryos.

(G, H) Ventral view of forelimb level spinal cord. Note the clear segregation of the MMC (medial strip of -Gal labeled cells) and LMC (lateral group of -Gal labeled cells) in the spinal cord of heterozygous $Hb9^{nlslacz}$ embryos (G) and the extensive intermixing of -Gal labeled cells in homozygous $Hb9^{nlslacZ}$ embryos (H).

(I, J) Ventral view of lumbar level spinal cord. A clear segregation of -Gal labeled cells in MMC (medial strip) and LMC (lateral strip) is observed in the spinal cord of heterozygous $Hb9^{nlslacZ}$ embryos (I) but not in homozygous $Hb9^{nlslacZ}$ embryos (J). Similar observations were made in younger stage embryos (e14.5 to e16.5).

FIG. 17. Transient Deregulation of Lim3 in Motor Neurons in Mice Lacking Hb9.

Analysis of Lim3 and Isl1 expression in -Gal labeled MNs in brachial spinal cord (level C7/8) at different developmental stages in $Hb9^{nlslacZ/+}$ and $Hb9^{nlslacZ/nlslacZ}$ embryos.

(A, B, E, F) Triple label immunocytochemical detection of Lim3 (green), -Gal (A, B: red) and Isl1 (E, F: red) on the same sections (A, E and B, F) of e10.5 $Hb9^{nlslacZ/+}$ and $Hb9^{nlslacZ/nlslacZ}$ embryos. In $Hb9^{nlslacZ/+}$ embryos, MMC MNs maintain Lim3 expression but most MNs rapidly downregulate Lim3. In $Hb9^{nls-lacZ/nls-lacZ}$ embryos examined at this stage, virtually all Isl1/-Gal cells coexpress Lim3.

(C, D, G, H) Developmental time course of Lim3 and Isl1 expression in $Hb9^{nlslacZ/+}$ (solid lines) and $Hb9^{nlslacZ/nlslacZ}$ (dashed lines) embryos. (C) Number of Lim3 cells. (D) Number of Lim3, -Gal cells. (G) Number of Isl1 cells. (H) Number of Lim3, Isl1 cells. Data from at least three independent sets of experiments for each developmental stage (e10, e10.5, e12.5 and e13.5) are shown. For each stage the number of positive cells per ventral quadrant of the spinal cord was counted on at least four consecutive sections.

FIG. 18. V2 Interneuron Marker Expression by Motor Neurons but no Accompanying Change in Axonal Trajectory in Mice Lacking Hb9.

Analysis of Chx10 expression by -Gal labeled cells and Isl1 MNs at different developmental stages in brachial spinal cord (level C7/8) of Hb9$^{nlslacZ/+}$ (A, C, D, F) and Hb9$^{nlslacZ/nlslacZ}$ (B, C, E, F) embryos.

(A, B, D, E) Triple label immunocytochemical analysis of Chx10 (green), -Gal (A, B: red) and Isl1 (D, E: red) expression in sections of e10.5 spinal cord from Hb9$^{nlslacZ/+}$ (A, D) and Hb9$^{nlslacZ/nlslacZ}$ (B, E) embryos. In Hb9$^{nlslacZ/+}$ embryos, there is no coincidence of expression of -Gal or Isl1 with Chx10. In Hb9$^{nlslacZ/nlslacZ}$, many Isl1 and -Gal labeled cells coexpress Chx10.

(C, F) Developmental time course of Chx10 expression in Hb9$^{nlslacZ/+}$ (solid lines) and Hb9$^{nlslacZ/nlslacZ}$ (dashed lines) embryos. The peak number of Chx10, -Gal cells in Hb9$^{nlslacZ/nlslacZ}$ embryos occurred at e10.5 after which their number gradually declined to that observed in Hb9$^{nlslacZ/+}$ embryos. Data from at least three independent sets of experiments are shown for each developmental stage (e10, e10.5, e12.5 and e13.5). For each stage the number of labeled cells per ventral quadrant of the spinal cord was counted on at least four consecutive sections.

(G–N) Retrograde HRP labeling from the base of the forelimb of e11.5 heterozygous Hb9$^{nlslacZ}$ (G, I) and homozygous Hb9$^{nlslacZ}$ (H, J) embryos. Triple label immunocytochemical detection of Chx10 (green), HRP (G, H: red) and Isl1 (I, J: red) on the same section (G, I and H, J). Arrows point to Chx10, HRP colabeled cells, two of which do not express Isl1.

(K–N) Axonal projection of Hb9 neurons in Hb9$^{taumyc/+}$ (K, M) and Hb9$^{taumyc/taumyc}$ (L, N) embryos, detected using anti-Myc epitope antibodies.

(K, L) Transverse sections of e13.5 spinal cord show myc-labeled axons projecting into the ventral roots.

(M, N) Parasagittal sections of e13.5 spinal cord (R: rostral, C: caudal, M: medial; L: lateral) showing MN cell bodies and intersegmental projections in the ventrolateral funiculus (vlf, white bar). Myc-labeled (red) axons are not detected amongst the neurofilament (NF) 160-labeled (green) axons in the vlf in Hb9$^{taumyc/taumyc}$ embryos, indicating the absence of intersegmental projections of ectopic Chox10 neurons. HRP injection into the vlf of the spinal cord of e13.5 wild type embryos labels ipsilateral Chx10 neurons at more caudal segmental levels (data not shown).

FIG. 19. Defects in Motor Neuron Subtype Identity in Hb9 Mutant Mice.

(A) Diagram summarizing sequential steps in motor neuron (MN) differentiation in the developing spinal cord. MNs (red) initially acquire a generic identity that distinguishes them from neighboring interneurons (in this diagram only V2 interneurons are shown). MNs initially express Isl1, whereas V2 neurons (blue) express Chx10. There are two major classes of spinal MNs, visceral and somatic, that project to different target cells. Most visceral MNs can be identified by expression of NADPH-diaphorase (NADPH-d) and somatic MNs by expression of Isl2. The somatic MN class consists of two major columns, the median (MMC) and lateral (LMC) motor columns that project to skeletal muscles in different peripheral locations. LMC MNs can be identified by expression of RALDH2 and MMC neurons by expression of Lim3 and Gsh4. Within the LMC, neurons in the medial (m) division coexpress Isl1 and Isl2 and project to ventrally-derived limb muscles whereas neurons in the lateral (l) division coexpress Isl2 and Lim1 and project to dorsally-derived limb muscles. Within each LMC division, MN pools that project to individual limb muscles can be identified by expression of the ETS domain proteins PEA3 and ER81. For details, see Tsuchida et al., 1994, Ericson et al., 1997a, Sockanathan and Jessell, 1998, Lin et al., 1998 and the text. (B–O) Expression of MN subtype markers in developing spinal MNs. Images show e13.5 thoracic spinal cord (B, C, F, G), e12.5 C7/8 level spinal cord (D, E), and e13.5 C7/8 level spinal cord (H–O) in Hb9$^{nlslacZ/+}$ and Hb9$^{nlslacZ/nlslacZ}$ embryos.

(B, C) Choline Acetyltransferase (ChAT, generic MN marker) expression detected by in situ hybridization. Arrows in (B) point to medial populations of visceral MNs.

(D, E) -Gal cells (red) coexpress Isl2 (green; a somatic MN-specific marker at this stage). The number of Isl2 cells is similar in Hb9$^{nlslacZ/+}$ and Hb9$^{nlslacZ}$ embryos examined at e12.5. By e13.5, the number of Isl2 cells in mutants is, however, reduced by ~40% compared to heterozygote embryos (data not shown).

(F, G) NADPH-diaphorase enzyme activity in visceral MNs. In heterozygous Hb9$^{nlslacZ}$ embryos, both lateral (l) and medial (m) populations of NADPH diaphorase neurons are present (F) In homozygous Hb9$^{nlslacZ}$ embryos, NADPH-diaphorase expression is absent from medial regions of the intermediate zone (G) although many cells in this region still express lacZ (data not shown).

(H, I) Coexpression of Lim3 (green) and -Gal (red) delineates the medial MMC in heterozygous Hb9$^{nlslacZ}$ embryos (H). Lim3, -Gal cells in homozygous Hb9$^{nlslacZ}$ embryos are not restricted to the region of the medial MMC (I).

(J, K) In situ hybridization analysis of RALDH2 expression delineates LMC neurons (J). There is a marked reduction of RALDH2 expression in homozygous Hb9$^{nlslacZ}$ embryos (K).

(L, M) Coexpression of Isl2 (red) and Lim1/2 (green) delineates lateral LMC neurons (L). There is a marked reduction of Isl2, Lim1 cells in homozygous Hb9$^{nlslacZ}$ embryos (M).

(N, O) PEA3 expression (green; motor pool marker) by pectoralis MNs (N) is severely reduced in homozygous Hb9$^{nlslacZ}$ embryos (O). PEA3 expression by DRG neurons (arrows) is not affected in homozygous Hb9$^{nlslacZ}$ embryos.

FIG. 20. Defects in Motor Axon Projections in Hb9 Mutant Mice.

(A–D) Whole mount -Gal staining of Hb9$^{taulacZ}$ embryos.

(A–C) Perturbation in motor axon projections in e11.5 Hb9$^{taulacZ/taulacZ}$ embryos (B, C), when compared with the axonal projection pattern observed in Hb9$^{taulacZ/+}$ embryos (A). Arrows point to the hypoglossal nerve which is absent or misrouted in some mutants (B) but present (C) in others. Asterisk in C indicates expanded plexus region at the base of the forelimb.

(D) Dorsal (d) and ventral (v) motor axon branches in the hindlimb of a e12.5 Hb9$^{taulacZ/taulacZ}$ embryo. Note -Gal labeling in the zone of polarizing activity (zpa) of the developing limb.

(E–H) Analysis of peripheral projections of motor axons in sections of e12.5 Hb9$^{taumyc/+}$ (E, F) and Hb9$^{taumyc/taumyc}$ (G, H) embryos. Double label immunocytochemical detection of myc-labeled (red) axons projecting towards skeletal muscles (-actinin-labeled; green). Axial muscle nerve branches are indicated (arrows, a). Star indicates the expansion of the axial nerve branch point (H) The dorsally (d) and ventrally (v) directed branches of motor axons in the limb are evident in Hb9 heterozygous (E) and homozygous (G) mutant embryos (I–L) Analysis of innervation of diaphragm muscle of post-natal day 0 wild type (I, K) and homozygous Hb9$^{nlslacZ}$ (J, L) mice.

(I,J) Whole-mount -bungarotoxin (-BTX) staining shows the presence of AChR clusters localized in a tight band in the diaphragm of wild type embryos (I) and a scattered distribution of AChR clusters over a larger region of the diaphragm muscle in homozygous Hb9$^{nlslacZ}$ embryos (J).

(K, L) Double label immunocytochemical detection of GAP43-labeled axons and nerve terminals (green) and -bungarotoxin-labeled AChR clusters (red). Transverse section through the diaphragm reveals the coincidence (yellow patches) of GAP43 and -bungarotoxin labeling in wild-type muscle (K) and the lack of coincidence of label in homozygous Hb9$^{nlslacZ}$ embryos (L).

FIG. 21. Functions of HB9 in the Differentiation of Post-Mitotic Motor Neurons.

Proposed functions of HB9 in post-mitotic MNs. Red arrows highlight the steps in MN differentiation that appear to be controlled by HB9. HB9 appears to have two main, and possibly interrelated, functions. First HB9 is normally required for the rapid down-regulation of Lim3 (and Gsh4) S from most post-mitotic MNs, which in turn appears to prevent expression of the V2 interneuron marker Chx10. One exception to this function of HB9 is in the context of medial MMC neurons, where Lim3 and Gsh4 expression persists in MNs for a prolonged period, even in wild-type embryos (Tsuchida et al., 1994; Sharma et al., 1998). Thus, medial MMC neurons appear to be subject to distinct regulatory controls on the timing of Lim3/Gsh4 expression and by inference, on the suppression of V2 interneuron character. Second, HB9 is required for the maintenance of Isl1 expression in post-mitotic MNs. A negative autoregulatory activity of HB9 is also shown and is indicated as a direct interaction, although it may be mediated indirectly. Approximate timing of cell cycle exit with respect to homeodomain protein expression is indicated. HB9 is also required, directly or indirectly, for the efficient establishment of the class, columnar, divisional and pool identities of spinal MNs. Dashed lines indicate that the erosion of MN subtype identity could reflect a direct action of HB9, the loss of expression of proteins such as Isl1 that normally serve a positive function in MN differentiation, or the ectopic expression of interneuron markers such as Chx10, or from a combination of these events. Proteins indicated in grey delineate markers of MN subtype identity that are affected in Hb9 mutants. Shh:Sonic hedgehog, an inductive signal required for motor neuron generation and HB9 expressoin. For further details, see text.

FIG. 22. HB9 is transiently expressed in the early developing pancreatic anlagen but reappears in insulin producing -cells. (a–f) HB9 and IPF1/PDX1 expression in pancreatic rudiments between stage e8–e10.5. (a) HB9 is expressed in both dorsal and ventral pancreatic epithelia in 8–10 somites stage embryos (e8), whereas (b) IPF1/PDX1 expression is only detected in the ventral pancreatic epithelium at this stage. Note that HB9 is also expressed in the notochord at this stage (indicated by the arrow). (c, d) By e9.5, HB9 and IPF1/PDX1 expression can be detected in both pancreatic buds although HB9 expression is expressed at a low level. (e) In e10.5 embryos the ventral HB9 expression is virtually absent and only very low levels of HB9 expression can be detected in the dorsal bud. (f) In contrast, IPF1/PDX1 expression is still expressed in both pancreatic buds. (g–i) Double immunohistochemical analysis of e17.5 pancreas using anti-HB9 and anti-insulin (i), anti-glucagon (h) or anti-somatostatin (i) antibodies. At this stage HB9 expression is restricted to the insulin producing cells. Abbreviations: d, dorsal pancreatic epithelium; v, ventral pancreatic epithelium.

FIG. 23. Hb9 deficient mice lack the dorsal pancreas. (a,b) The pancreatic region of e17.5 (a) and e13.5 (b) Hb9$^{nlslacZ}$ heterozyogous and homozygous littermates demonstrating the loss of dorsal pancreatic epithelium whereas the ventral pancreas, dorsal mesenchyme and spleen develops in homozygous mutant embryos. (c–j) The development of the dorsal pancreas is arrested before the stage of epithelial evagination in Hb9$^{nlslacZ}$ homozygous embryos. (c–j) X-gal staining or IPF1/PDX1 immunohistochemistry of wholemount and transversal cryostat sections of e9.5–10.5 heterozygous and homozygous embryos. (c, d) Whole-mount X-gal staining of e9.5 embryos shows that the protruding, dorsal pancreatic bud can be detected in the heterozygous embryos whereas no equivalent structure is found in the homozygous embryos. (e,f) Immunohistochemical analysis of heterozygous and homozygous e9.5 embryos demonstrates the absence of IPF1/PDX1 expression in the presumptive dorsal pancreatic epithelium of homozygous embryos. (g–j) X-gal staining of e10.5 embryos showing that at this stage the ventral bud has formed in both the heterozygous and homozygous embryos whereas there is no evidence of a dorsal pancreatic bud in homozygous embryos. Note that lacZ activity still can be readily detected in both buds at this stage although, when analysed immunohistochemically using anti-HB9 antibodies, HB9 protein expression is barely detectable at this stage (see FIG. 1e for comparison). This is probably due to a combination of high sensitivity when staining for lacZ activity as compared to using antibodies, together with the persistence of -galactosidase protein. No lacZ activity is detected in the notochord at this stage. Abbreviations: s, stomach; d, duodenum; sp, spleen; dp, dorsal pancreas; vp, ventral pancreas; MN, motor neurons. (Arrowhead indicates dorsal pancreatic bud.)

FIG. 24. Early pancreatic cell differentiation of the dorsal bud is impaired in the Hb9$^{nlslacZ}$ homoygotes. (a–f) Immunohistochemical analyses of e9.5 wild-type (a,c,e) and Hb9$^{nlslacZ}$ homozygous (b,d,f) embryos using anti-Isl-1 (a,b), anti-Nkx2.2 antibodies (c,d) and anti-glucagon (e,f) antibodies. None of these early pancreatic markers is detected in the dorsal pancreatic epithelium. (g–j) Shh (g,h) and Ihh (i,j) expression is unaffected in e9.5 Hb9$^{nlslacZ}$ homozygotes (h,j) as compared to stage-matched wild-type littermates (g,i). The broken line indicates the pancreatic buds FIG. 25. The ventral pancreas of Hb9 deficient mice exhibit a perturbed islet cell organisation with immature -cells. (a–j) Immunohistochemical analysis of pancreatic marker expression in the ventral pancreas derived from a wild-type (a,c,e,g,i) and Hb9$^{nlslacZ}$ homozygous (b,d,f,h,j) neonates. Both endocrine and exocrine cells appear as shown by the presence of (a–d,g,h) insulin$^+$, glucagon$^+$, (c,d) somatostatin$^+$, and amylase$^+$ cells but the endocrine cells fail to organise themselves into the typical structure of maturing islets. (g–j) The insulin-positive cells present in the ventral bud of Hb9$^{nlslacZ}$ homozygous express IPF1/PDX1 but not Glut2 indicating that they are not terminally differentiated.

DETAILED DESCRIPTION OF THE INVENTION

The following standard abbreviations are used throughout the specification to indicate specific nucleotides:
C=cytosine
A=adenosinc
T=thymidine
G=guanosine This invention provides an isolated nucleic molecule encoding a motor neuron restricted pattern, MNR2, protein.

In an embodiment the isolated nucleic molecule encoding a motor neuron restricted pattern, MNR2, protein is a DNA molecule. In another embodiment the isolated nucleic acid molecule encoding a motor neuron restricted pattern, MNR2, protein is a cDNA molecule. In a further embodiment the isolated DNA molecule encoding a motor neuron restricted pattern, MNR2, protein is a RNA molecule. In an embodiment the isolated nucleic acid molecule encoding a motor neuron restricted pattern is operatively linked to a promoter of RNA transcription.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described: and claimed herein are useful for the information which they provide concerning the amino acid sequence of the polypeptide, MNR2, and as products for the large scale synthesis of the polypeptide MNR2, or fragments thereof, by a variety of recombinant techniques. The DNA molecule is useful for generating new cloning and expression vectors, transformed and transfected prokaryotic and eukaryotic host cells, and new and useful methods for cultured growth of such host cells capable of expression of the polypeptide MNR2 or portions thereof and related products.

In another embodiment the isolated nucleic acid molecule which is a cDNA molecule which, encoding a motor neuron restricted pattern MNR2 protein, encodes a chick MNR2 protein. In another embodiment the isolated nucleic acid molecule is a cDNA molecule wherein the nucleic acid molecule encodes a chick MNR2 protein comprising the amino acid sequence set forth in SEQ ID NO: 1. In a further embodiment the isolated nucleic acid molecule is a cDNA molecule wherein the nucleic acid molecule encodes a mammalian MNR2 protein. In an embodiment the isolated nucleic acid molecule is a cDNA molecule wherein the nucleic acid molecule encodes a mammalian MNR2 protein which is a mouse, rat or human protein. In an embodiment the isolated nucleic acid molecule is a cDNA molecule, which comprises the nucleic acid sequence set forth in SEQ ID NO: 2.

This invention provides a vector which comprises the isolated nucleic acid encoding a motor neuron restricted pattern, MNR2, protein operatively linked to a promoter of RNA transcription. In an embodiment a plasmid comprises the vector which comprises the isolated nucleic acid encoding a motor neuron restricted pattern, MNR2, protein. In another embodiment: the plasmid, which comprises the vector which comprises the isolated nucleic acid encoding a chick motor neuron restricted pattern, pMNR2, protein, is designated pMNR2.

In an embodiment, a full-length cDNA nucleic acid molecule encoding a MNR2 protein is inserted into a pcs2$^+$ plasmid and the resulting plasmid is designated as pcs2$^+$ MNR2. The plasmid is with ampicillin resistance and 1.2 kilobase insert is releasable by cleavage with ClaI restriction endonuclease. Plasmid pcs2$^+$MNR2 was deposited on Sep. 28, 1998 with the American Type Culture Collection (ATCC) 10801 University Boulevard, Manassas, Va. 20110-2209, U.S.A. under the provisions of the Budapest Treaty for the International Recognition of the Deposit of Microorganisms for the Purposes of Patent Procedure. Plasmid pcs2$^+$ MNR2 was accorded ATCC Accession Number 203294.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Methods of introducing nucleic acid molecules into cells are well known to those of skill in the art. Such methods include, for example, the use of viral vectors and calcium phosphate co-precipitation.

The "suitable host cell" in which the nucleic acid molecule encoding is MNR2 protein capable of being expressed is any cell capable of taking up the nucleic acid molecule and stably expressing the MNR2 encoded thereby.

This invention provides a host cell containing the vector which comprises the isolated nucleic acid encoding a motor neuron restricted pattern, MNR2, protein. In an embodiment the host cell is selected from a group consisting of a bacterial cell, a plant cell, an insect cell and a mammalian cell.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk⁻ cells and COS cells. Mammalian cells may be transfected by methods well known in the art such as calcium phosphate precipitation, electroporation and microinjection.

This invention provides a method of producing a polypeptide having the biological activity of a mammalian MNR2 which comprises growing host cells selected from a group consisting of bacterial, plant, insect or mammalian cell, under suitable conditions permitting production of the polypeptide. In another embodiment of the method of producing a polypeptide having the biological activity of a mammalian MNR2 the method further comprises of the recovering the produced polypeptide.

This invention provides an isolated nucleic acid molecule of at least 15 contiguous nucleotides capable of specifically hybridizing with a unique sequence included within the sequence of the nucleic acid molecule encoding a motor neuron restricted pattern, MNR2, protein. In an embodiment the isolated nucleic acid molecule of at least 15 contiguous nucleotides capable of specifically hybridizing with a unique sequence included within the sequence of the nucleic acid molecule encoding a motor neuron restricted pattern, MNR2, protein is a DNA molecule. In another embodiment the isolated nucleic acid molecule of at least 15 contiguous nucleotides capable of specifically hybridizing with a unique sequence included within the sequence of the nucleic acid molecule encoding a motor neuron restricted pattern, MNR2, protein, is a RNA molecule.

This invention provides an isolated nucleic acid molecule capable of specifically hybridizing with a unique sequence included within the sequence of a nucleic acid molecule which is complementary to the nucleic acid molecule encoding a motor neuron restricted pattern, MNR2, protein. In an embodiment the isolated nucleic acid molecule capable of specifically hybridizing with a unique sequence included within the sequence of a nucleic acid molecule which is complementary to the nucleic acid molecule encoding a motor neuron restricted pattern, MNR2, protein, is a DNA molecule. In another embodiment the isolated nucleic acid molecule capable of specifically hybridizing with a unique sequence included within the sequence of a nucleic acid molecule which is complementary to the nucleic acid molecule encoding a motor neuron restricted pattern, MNR2, protein is a RNA molecule.

One of ordinary skill in the art will easily obtain unique sequences from the cDNA cloned in the pMNR2 plasmid. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in the pMNR2 plasmid may further be used to screen other human tissue cDNA libraries to obtain isoforms of the nucleic acid sequences encoding MNR2 protein as well as to screen human genomic DNA to obtain the analogous nucleic acid sequences. The homologous nucleic acid sequences and isoforms may be used to produce the proteins encoded thereby.

As used herein, "capable of specifically hybridizing" means capable of: binding to an mRNA molecule encoding a MNR2 but not capable of binding to an mRNA molecule encoding a MNR2 receptor protein.

This invention provides an antisense oligonucleotide having a nucleic acid sequence capable of specifically hybridizing to an mRNA molecule encoding a MNR2 protein. In an embodiment the antisense oligonucleotide has a nucleic acid sequence capable of specifically hybridizing to the isolated cDNA molecule encoding a motor neuron restricted pattern, MNR2, protein. In an embodiment the antisense oligonucleotide has a nucleic acid sequence capable of specifically hybridizing to an isolated RNA molecule encoding a motor neuron restricted pattern, MNR2 protein.

This invention provides a purified MNR2 protein. In an embodiment the purified MNR2 protein is encoded by an isolated nucleic acid encoding a motor neuron restricted pattern, MNR2, protein. In another embodiment the MNR2 protein unique polypeptide fragment of the purified MNR2 protein. In an embodiment the purified MNR2 protein has substantially the same amino acid sequence as set forth in SEQ ID NO: 1. In a further embodiment the purified MNR2 protein having an amino acid sequence as set forth in SEQ ID NO: 1. In another embodiment the purified MNR2 protein has an amino acid sequence as set forth in SEQ ID NO: 1. In a further embodiment, the MNR2 protein is a vertebrate MNR2 protein. In an embodiment the purified vertebrate MNR2 protein having an amino acid sequence as set forth in SEQ ID NO: 12 is a chick, mouse or rat MNR2 protein.

As used herein, an MNR2 protein having "substantially the same" amino acid sequences as set forth in SEQ ID NO: 1 is encoded by a nucleic acid encoding MNR2, said nucleic acid having 100% identity in the homeodomain regions, that is those regions coding the protein, and said nucleic acid may vary in the nucleotides in the non-coding regions.

This invention provides a monoclonal antibody directed to an epitope of an MNR2 protein. In an embodiment the monoclonal antibody is directed to a chick, mouse or rat MNR2 protein.

This invention provides a polyclonal antibody directed to an epitope of the purified MNR2 protein having the amino sequence as set forth in SEQ ID No: 1. In a further embodiment the monoclonal or polyclonal antibodies are directed to the MNR2 protein, having the amino sequence as set forth in SEQ ID NO: 1.

Polyclonal antibodies may be produced by injecting a host animal such as rabbit, rat, goat, mouse or other animal with the immunogen of this invention, e.g. a purified mammalian MNR2 protein or a purified human MNR2 protein. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual*, (Cold Spring Harbor Laboratories, Cold Spring Harbor, N.Y.: 1988) the contents of which are hereby incorporated by reference.

The monoclonal antibodies may be produced by immunizing for example, mice with an immunogen. The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495–497. Available murine myeloma lines, such as those from the American Type Culture Collection (ATCC) 12301 Parklawn Drive, Rockville, Md. 20852 USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. As used in the subject invention, the term "antibody" includes, but is not limited to, both naturally occurring and non-naturally occurring antibodies. Specifically, the term "antibody" includes polyclonal and monoclonal antibodies, and binding fragments thereof. Furthermore, the term "antibody" includes chimeric antibodies and wholly synthetic antibodies, and fragments thereof.

Furthermore, the term "antibody" includes chimeric antibodies; and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

Determining whether the antibody forms such a complex may be accomplished according to methods well known to those skilled in the art. In the preferred embodiment, the determining is accomplished according to flow cytometry methods.

The antibody may be bound to an insoluble matrix such as that used in affinity chromatography. As used in the subject invention, isolating the cells which form a complex with the immobilized monoclonal antibody may be achieved by standard methods well known to those skilled in the art. For example, isolating may comprise affinity chromatography using immobilized antibody.

Alternatively, the antibody may be a free antibody. In this case, isolating may comprise cell sorting using free, labeled primary or secondary antibodies. Such cell sorting methods are standard and are well known to those skilled in the art.

The labeled antibody may be a polyclonal or monoclonal antibody. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. The detectable marker may be, for example, radioactive or fluorescent. Methods of labeling antibodies are well known in the art.

This invention provides a method of inducing differentiation of somatic motor neurons which comprises expressing MNR2 protein in any neural progenitor cells. In an embodiment of the method, expression of MNR2 protein induces expression of transcription factors Isl2, Lim 3 and HB9. In a further embodiment of the method of inducing differentiation of somatic motor neurons the neural progenitor cells are spinal cord or hindbrain motor neuron progenitor cells.

This invention provides a transgenic nonhuman mammal which comprises an isolated nucleic acid, including a motor neuron restriction pattern, MNR2 protein, which is a DNA molecule. In an embodiment of the transgenic nonhuman mammal the DNA encoding a MNR2 protein is operatively linked to tissue specific regulatory elements.

This invention provides a method of determining physiological effects of expressing varying levels of MNR2 protein in a transgenic nonhuman mammal which comprises producing a panel of transgenic nonhuman animals, each nonhuman mammal expressing a different amount of MNR2 protein.

This invention provides a method of producing isolated purified MNR2 protein which comprises: a) inserting a nucleic acid molecule encoding an MNR2 protein into a suitable vector; b) introducing the resulting vector into a suitable host cell; c) selecting the introduced host cell for the expression of the MNR2 protein; d) culturing the selected cell to produce the MNR2 protein; and e) recovering the MNR2 protein produced.

This invention provides a method of inducing differentiation of somatic motor neurons in a subject comprising administering to the subject the purified MNR2 protein in an amount effective to induce differentiation of somatic motor neurons in the subject. In an embodiment, a functionally equivalent analog of MNR2 is administered to the subject. In an embodiment of the method of inducing differentiation of somatic motor neurons in a subject comprising administering to the subject the purified MNR2 protein in an amount effective to induce differentiation of somatic motor neurons in the subject, the subject is a mammal. In another embodiment of the above-described method of inducing differentiation of somatic motor neurons in a subject, the subject is a chick, mouse, rat or human.

As used herein, "subject" means any animal or artificially modified animal. Artificially modified animals include, but are not limited to, SCID mice with human immune systems. In the preferred embodiment, the subject is a human.

This invention provides a pharmaceutical composition comprising a purified MNR2 protein and a pharmaceutically acceptable carrier.

The invention also provides a pharmaceutical composition comprising a effective amount of the MNR2 proteins described above and a pharmaceutically acceptable carrier. In the subject invention an "effective amount" is any amount of above-described MNR2 proteins which, when administered to a subject suffering from a disease or abnormality against which the proteins are determined to be potentially therapeutic, are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The above described pharmaceutical composition comprising MNR2 protein can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The above described pharmaceutical composition comprising MNR2 protein can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular above described pharmaceutical composition comprising MNR2 protein in use, the strength of the preparation, the mode of administration, and the advancement of the disease condition or abnormality. Additional factors depending on the particular subject being treated will result in a need to adjust dosages, including subject age, weight, gender, diet, and time of administration.

The subject invention further provides a composition which comprises an effective amount of a nucleic acid molecule encoding MNR2 capable of being expressed in a suitable host cell, and a pharmaceutically acceptable carrier.

This invention provides a method for treating a subject afflicted with an abnormality associated with a lack of one or more normally functioning motor neurons which comprises introducing an amount of the pharmaceutical composition comprising of a purified MNR2 protein and a pharmaceutically acceptable carrier effective to generate somatic motor neurons from undifferentiated motor neuron precursor cells in the subject, thereby treating the subject afflicted with the abnormality associated with the lack of one or more normally functioning motor neurons.

As used herein a "normally functioning motor neuron" is a motor neuron that can control muscle contraction and respond to sensory input.

As used herein, administering may be effected or performed using any of the various methods known to those skilled in the art. The administration may be intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

This invention provides a method of treating a subject afflicted with a neurodegenerative disease which comprises introducing an amount of the pharmaceutical composition which comprises a purified MNR2 protein and a pharmaceutically acceptable carrier effective to generate somatic motor neurons from undifferentiated precursor motor neuron cells in the subject, thereby treating the subject afflicted with the neurodegenerative disease. In an embodiment of the method of treating a subject with a neurodegenerative disease which comprises introducing an amount of pharmaceutical composition which comprises a purified MNR2 protein and a pharmaceutically acceptable carrier effective to generate somatic motor neurons from undifferentiated precursor motor neuron cells in the subject, the generation of motor neurons from undifferentiated precursor motor neuron cells alleviates a chronic neurodegenerative disease. In an embodiment of the above-described method of treating a subject afflicted with a chronic neurodegenerative disease where the disease is a spinal muscular atrophy. In a further embodiment the of method of treating a subject afflicted with a chronic neurodegenerative disease the disease is amyotrophic lateral sclerosis (Lou Gehrig's Disease).

This invention provides for a method of treating a subject afflicted with an acute nervous system injury which comprises introducing an amount of a pharmaceutical composition which comprises a purified MNR2 protein and a pharmaceutically acceptable carrier effective to generate motor neurons from undifferentiated precursor motor neuron cells in a subject, thereby treating the subject afflicted with the acute nervous system injury.

This invention provides for a method of treating a subject afflicted with an acute nervous system injury which comprises introducing an amount of pharmaceutical composition which comprises a purified MNR2 protein and a pharmaceutically acceptable carrier effective to generate motor neurons from undifferentiated precursor motor neuron cells in a subject, wherein the acute nervous system injury is localized to a specific central axon which comprises surgical implantation of the pharmaceutical compound comprising a MNR2 protein and a pharmaceutically acceptable carrier effective to generate motor neurons from undifferentiated precursor motor neuron cells located proximal to the specific central axon, so as to alleviate the acute nervous system injury localized to a specific central axon, thereby treating the subject afflicted with the acute nervous system injury.

This invention provides a method for diagnosing a chronic neurodegnerative disease associated with the expression of a MNR2 protein in a sample from a subject which comprises: a. obtaining DNA from the sample of the subject suffering from the chronic neurodegenerative disease; b. performing a restriction digest of the DNA with a panel of restriction enzymes; c. separating the resulting DNA fragments by size fractionation; d. contacting the resulting DNA fragments with a nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence and labeled with a detectable marker; e. detecting labeled bands which have hybridized to the nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence to create a unique band pattern specific to the DNA of subjects suffering from the chronic neurodegenerative disease; f. preparing DNA obtained from a sample of a subject for diagnosis by steps (a–e); and g. comparing the detected band pattern specific to the DNA obtained from a sample of subjects suffering from the chronic neurodegenerative disease from step (e) and the DNA obtained from a sample of the subject for diagnosis from step (f) to determine whether the patterns are the same or different and to diagnose thereby predisposition to the chronic neurodegenerative disease if the patterns are the same.

This invention provides a method for diagnosing a chronic neurodegenerative disease associated with the expression of a MNR2 protein in a sample from a subject which comprises: a. obtaining RNA from the sample of the subject suffering from chronic neurodegenerative disease; b. separating the RNA sample by size fractionation; c. contacting the resulting RNA species with a nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence and labeled is with a detectable marker; d. detecting labeled bands which have hybridized to the RNA species to create a unique band pattern specific to the RNA of subjects suffering from the chronic neurodegenerative disease; f. preparing RNA obtained from a sample of a subject for diagnosis by steps (a–d); and g. comparing the detected band pattern specific to the RNA obtained from a sample of subjects suffering from the chronic neurodegenerative disease from step (d) and the RNA obtained from a sample of the subject for diagnosis from step (f) to determine whether the patterns are the same or different and to diagnose thereby predisposition to the chronic neurodegenerative disease if the patterns are the same.

This invention provides a functionally equivalent analog of MNR2 that induces MNR2 differentiation of neural progenitor cells.

This invention provides a functionally equivalent analog of MNR2 that prevents MNR2 differentiation of neural progenitor cells.

This invention provides a method of treating a subject afflicted with a neuromuscular disease which comprises introducing an amount of a pharmaceutical composition comprising a purified MNR2 protein and a pharmaceutically acceptable carrier effective to activate acetylcholine to activate muscle cells.

In order to facilitate an understanding of the Experimental Details section which follows, certain frequently occurring methods and/or terms are best described in Sambrook, et al. (1989).

This invention will be better understood from the Experimental Details which follow. However, one skilled in the art will readily appreciate that the specific methods and results discussed are merely illustrative of the invention as described more fully in the claims which follow thereafter.

This invention provides an isolated nucleic molecule encoding a homeobox, HB9, protein. In an embodiment the isolated nucleic molecule encoding a homeobox HB9, protein is a DNA molecule. In another embodiment the isolated nucleic acid molecule encoding a homeobox, HB9, protein is a cDNA molecule. In a further embodiment the isolated DNA molecule encoding a homeobox, HB9, protein is a RNA molecule. In an embodiment the isolated nucleic acid molecule encoding a motor neuron restricted pattern is operatively linked to a promoter of RNA transcription.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide, HB9, and as products for the large scale synthesis of the polypeptide HB9, or fragments thereof, by a variety of recombinant techniques. The DNA molecule is useful for generating new cloning and expression vectors, transformed and transfected prokaryotic and eukaryotic host cells, and new and useful methods for cultured growth of such host cells capable of expression of the polypeptide HB9 or portions thereof and related products.

In another embodiment the isolated nucleic acid molecule which is a cDNA molecule which, encoding a homebox HB9 protein, encodes a chick HB9 protein. In another embodiment the isolated nucleic acid molecule is a cDNA molecule wherein the nucleic acid molecule encodes a chick HB9 protein comprising the amino acid sequence set forth in SEQ ID NO: 3. In a further embodiment the isolated nucleic acid molecule is a cDNA molecule wherein the nucleic acid molecule encodes a mammalian HB9 protein. In an embodiment the isolated nucleic acid molecule is a cDNA molecule wherein the nucleic acid molecule encodes a mammalian HB9 protein which is a mouse, rat or human protein. In an embodiment the isolated nucleic acid molecule is a cDNA molecule, which comprises the nucleic acid sequence set forth in SEQ ID NO: 4.

This invention provides a vector which comprises the isolated nucleic acid encoding a motor neuron restricted pattern, HB9, protein operatively linked to a promoter of RNA transcription. In an embodiment a plasmid comprises the vector which comprises the isolated nucleic acid encoding a homeobox HB9, protein. In another embodiment the plasmid, which comprises the vector which comprises the isolated nucleic acid encoding a chick HB9 pattern, pHB9. (SEQ ID NO.:3)

In an embodiment, a full-length cDNA nucleic acid molecule encoding a HB9 protein is inserted into a plasmid and the resulting plasmid is designated as pHB9. The plasmid is with ampicillin resistance and 1.2 kilobase insert is releasable by cleavage with ClaI restriction endonuclease.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Methods of introducing nucleic acid molecules into cells are well known to those of skill in the art. Such methods include, for example, the use of viral vectors and calcium phosphate co-precipitation.

The "suitable host cell" in which the nucleic acid molecule encoding is HB9 protein capable of being expressed is any cell capable of taking up the nucleic acid molecule and stably expressing the HB9 encoded thereby.

This invention provides a host cell containing the vector which comprises the isolated nucleic acid encoding a homeobox, HB9, protein. In an embodiment the host cell is selected from a group consisting of a bacterial cell, a plant cell, an insect cell and a mammalian cell.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk$^-$ cells and COS cells. Mammalian cells may be transfected by methods well known in the art such as calcium phosphate precipitation, electroporation and microinjection.

This invention provides a method of producing a polypeptide having the biological activity of a mammalian HB9 which comprises growing host cells selected from a group consisting of bacterial, plant, insect or mammalian cell, under suitable conditions permitting production of the polypeptide. In another embodiment of the method of producing a polypeptide having the biological activity of a mammalian HB9 the method further comprises of the recovering the produced polypeptide.

This invention provides an isolated nucleic acid molecule of at least 15 contiguous nucleotides capable of specifically hybridizing with a unique sequence included within the sequence of the nucleic acid molecule encoding a homeobox, HB9, protein. In an embodiment the isolated nucleic acid molecule of at least 15 contiguous nucleotides capable of specifically hybridizing with a unique sequence included within the sequence of the nucleic acid molecule encoding a homeobox, HB9, protein is a DNA molecule. In another embodiment the isolated nucleic acid molecule of at least 15 contiguous nucleotides capable of specifically hybridizing with a unique sequence included within the sequence of the nucleic acid molecule encoding a homebox, HB9, protein, is a RNA molecule.

This invention provides an isolated nucleic acid molecule capable of specifically hybridizing with a unique sequence included within the sequence of a nucleic acid molecule which is complementary to the nucleic acid molecule encoding a homebox, HB9, protein. In an embodiment the isolated nucleic acid molecule capable of specifically hybridizing with a unique sequence included within the sequence of a nucleic acid molecule which is complementary to the nucleic acid molecule encoding a homeobox, HB9, protein, is a DNA molecule. In another embodiment the isolated nucleic acid molecule capable of specifically hybridizing with a unique sequence included within the sequence of a nucleic acid molecule which is complementary to the nucleic acid molecule encoding a homeobox, HB9, protein is a RNA molecule.

One of ordinary skill in the art will easily obtain unique sequences from the cDNA cloned in the plasmid. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in the pHB9 plasmid may further be used to screen other human tissue cDNA libraries to obtain isoforms of the nucleic acid sequences encoding HB9 protein as well as to screen human genomic DNA to obtain the analogous nucleic acid sequences. The homologous nucleic acid sequences and isoforms may be used to produce the proteins encoded thereby.

As used herein, "capable of specifically hybridizing" means capable of binding to an mRNA molecule encoding a HB9 but not capable of binding to an mRNA molecule encoding a HB9 receptor protein.

This invention provides an antisense oligonucleotide having a nucleic acid sequence capable of specifically hybridizing to an mRNA molecule encoding a HB9 protein. In an embodiment the antisense oligonucleotide has a nucleic acid sequence capable of specifically hybridizing to the isolated cDNA molecule encoding a homeobox, HB9, protein. In an embodiment the antisense oligonucleotide has a nucleic acid sequence capable of specifically hybridizing to an isolated RNA molecule encoding a homeobox, HB9, protein.

This invention provides a purified HB9 protein. In an embodiment the purified HB9 protein is encoded by an isolated nucleic acid encoding a homeobox, HB9, protein. In another embodiment the HB9 protein unique polypeptide fragment of the purified HB9 protein. In an embodiment the purified HB9 protein has substantially the same amino acid sequence as set forth in SEQ ID NO: 3. In a further embodiment the purified HB9 protein having a nucleic acid sequence as set forth in SEQ ID NO: 4. In another embodiment the purified HB9 protein has an amino acid sequence as set forth in SEQ ID NO: 3. In a further embodiment, the MNR2 protein is a vertebrate HB9 protein. In an embodiment the purified vertebrate HB9 protein having an amino acid sequence as set forth in SEQ ID NO: 3 is a chick, mouse or rat HB9 protein.

As used herein, an HB9 protein having "substantially the same" amino acid sequences as set forth in SEQ ID NO: 3 is encoded by a nucleic acid encoding HB9, said nucleic acid having 100% identity in the homeodomain regions, that is those regions coding the protein, and said nucleic acid may vary in the nucleotides in the non-coding regions.

This invention provides a monoclonal antibody directed to an epitope of an HB9 protein. In an embodiment the monoclonal antibody is directed to a chick, mouse or rat HB9 protein.

This invention provides a polyclonal antibody directed to an epitope of the purified HB9 protein having the amino sequence as set forth in SEQ ID No: 3. In a further embodiment the monoclonal or polyclonal antibodies are directed to the HB9 protein, having the amino acid sequence as set forth in SEQ ID NO: 3.

Polyclonal antibodies may be produced by injecting a host animal such as rabbit, rat, goat, mouse or other animal with the immunogen of this invention, e.g. a purified mammalian HB9 protein or a purified human HB9 protein. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual*, (Cold Spring Harbor Laboratories, Cold Spring Harbor, N.Y.: 1988) the contents of which are hereby incorporated by reference.

The monoclonal antibodies may be produced by immunizing for example, mice with an immunogen. The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495–497. Available murine myeloma lines, such as those from the American Type Culture Collection (ATCC) 12301 Parklawn Drive, Rockville, Md. 20852 USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. As used in the subject invention, the term "antibody" includes, but is not limited to, both naturally occurring and non-naturally occurring antibodies. Specifically, the term "antibody" includes polyclonal and monoclonal antibodies, and binding fragments thereof. Furthermore, the term "antibody" includes chimeric antibodies and wholly synthetic antibodies, and fragments thereof.

Furthermore, the term "antibody" includes chimeric antibodies and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

Determining whether the antibody forms such a complex may be accomplished according to methods well known to those skilled in the art. In the preferred embodiment, the determining is accomplished according to flow cytometry methods.

The antibody may be bound to an insoluble matrix such as that used in affinity chromatography. As used in the subject invention, isolating the cells which form a complex with the immobilized monoclonal antibody may be achieved by standard methods well known to those skilled in the art. For example, isolating may comprise affinity chromatography using immobilized antibody.

Alternatively, the antibody may be a free antibody. In this case, isolating may comprise cell sorting using free, labeled primary or secondary antibodies. Such cell sorting methods are standard and are well known to those skilled in the art.

The labeled antibody may be a polyclonal or monoclonal antibody. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. The detectable marker may be, for example, radioactive or fluorescent. Methods of labeling antibodies are well known in the art.

This invention provides a method of inducing differentiation of somatic motor neurons which comprises expressing MNR2 protein in any neural progenitor cells. In an embodiment of the method, expression of HB9 protein induces expression of transcription factors Isl2, Lim 3 and HB9. In a further embodiment of the method of inducing differentiation of somatic motor neurons the neural progenitor cells are spinal cord or hindbrain motor neuron progenitor cells.

This invention provides a transgenic nonhuman mammal which comprises an isolated nucleic acid, including a motor neuron restriction pattern, HB9 protein, which is a DNA molecule.

In an embodiment of the transgenic nonhuman mammal the DNA encoding a HB9 protein is operatively linked to tissue specific regulatory elements.

This invention provides a method of determining physiological effects of expressing varying levels of HB9 protein in a transgenic nonhuman mammal which comprises producing a panel of transgenic nonhuman animals, each nonhuman mammal expressing a different amount of HB9 protein.

This invention provides a method of producing isolated purified HB9 protein which comprises: a) inserting a nucleic acid molecule encoding an HB9 protein into a suitable vector; b) introducing the resulting vector into a suitable host cell; c) selecting the introduced host cell for the expression of the HB9 protein; d) culturing the selected cell to produce the HB9 protein; and e) recovering the HB9 protein produced.

This invention provides a method of inducing differentiation of somatic motor neurons in a subject comprising administering to the subject the purified HB9 protein in an amount effective to induce differentiation of somatic motor neurons in the subject. In an embodiment, a functionally equivalent analog of HB9 is administered to the subject. In an embodiment of the method of inducing differentiation of somatic motor neurons in a subject comprising administering to the subject the purified HB9 protein in an amount effective to induce differentiation of somatic motor neurons in the subject, the subject is a mammal. In another embodiment of the above-described method of inducing differentiation of somatic motor neurons in a subject, the subject is a chick, mouse, rat or human.

As used herein, "subject" means any animal or artificially modified animal. Artificially modified animals include, but are not limited to, SCID mice with human immune systems. In the preferred embodiment, the subject is a human.

This invention provides a pharmaceutical composition comprising a purified HB9 protein and a pharmaceutically acceptable carrier.

The invention also provides a pharmaceutical composition comprising a effective amount of the HB9 proteins described above and a pharmaceutically acceptable carrier. In the subject invention an "effective amount" is any amount of above-described HB9 proteins which, when administered to a subject suffering from a disease or abnormality against which the proteins are determined to be potentially therapeutic, are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The above described pharmaceutical composition comprising HB9 protein can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitan and its anhydrides copolymerized with ethylene oxide) and the like.

The above described pharmaceutical composition comprising HB9 protein can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular above described pharmaceutical composition comprising HB9 protein in use, the strength of the preparation, the mode of administration, and the advancement of the disease condition or abnormality. Additional factors depending on the particular subject being treated will result in a need to adjust dosages, including subject age, weight, gender, diet, and time of administration.

The subject invention further provides a composition which comprises an effective amount of a nucleic acid molecule encoding HB9 capable of being expressed in a suitable host cell, and a pharmaceutically acceptable carrier.

This invention provides a method for treating a subject afflicted with an abnormality associated with a lack of one or more normally functioning motor neurons which comprises introducing an amount of the pharmaceutical composition comprising of a purified HB9 protein and a pharmaceutically acceptable carrier effective to generate somatic motor neurons from undifferentiated motor neuron precursor cells in the subject, thereby treating the subject afflicted with the abnormality associated with the lack of one or more normally functioning motor neurons.

As used herein a "normally functioning motor neuron" is a motor neuron that can control muscle contraction and respond to sensory input.

As used herein, administering may be effected or performed using any of the various methods known to those skilled in the art. The administration may be intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

This invention provides a method of treating a subject afflicted with a neurodegenerative disease which comprises introducing an amount of the pharmaceutical composition which comprises a purified HB9 protein and a pharmaceutically acceptable carrier effective to generate somatic motor neurons from undifferentiated precursor motor neuron cells in the subject, thereby treating the subject afflicted with the neurodegenerative disease. In an embodiment of the method of treating a subject with a neurodegenerative disease which comprises introducing an amount of pharmaceutical composition which comprises a purified HB9 protein and a pharmaceutically acceptable carrier effective to generate somatic motor neurons from undifferentiated precursor motor neuron cells in the subject, the generation of motor neurons from undifferentiated precursor motor neuron cells alleviates a chronic neurodegenerative disease. In an embodiment of the above-described method of treating a subject afflicted with a chronic neurodegenerative disease where the disease is a spinal muscular atrophy. In a further embodiment the of method of treating a subject afflicted with a chronic neurodegenerative disease the disease is amyotrophic lateral sclerosis (Lou Gehrig's Disease).

This invention provides for a method of treating a subject afflicted with an acute nervous system injury which comprises introducing an amount of a pharmaceutical composition which comprises a purified HB9 protein and a pharmaceutically acceptable carrier effective to generate motor neurons from undifferentiated precursor motor neuron cells in a subject, thereby treating the subject afflicted with the acute nervous system injury.

This invention provides for a method of treating a subject afflicted with an acute nervous system injury which comprises introducing an amount of pharmaceutical composition which comprises a purified HB9 protein and a pharmaceutically acceptable carrier effective to generate motor neurons from undifferentiated precursor motor neuron cells in a subject, wherein the acute nervous system injury is localized to a specific central axon which comprises surgical implantation of the pharmaceutical compound comprising a HB9 protein and a pharmaceutically acceptable carrier effective to generate motor neurons from undifferentiated precursor motor neuron cells located proximal to the specific central axon, so as to alleviate the acute nervous system injury localized to a specific central axon, thereby treating the subject afflicted with the acute nervous system injury.

This invention provides a method for diagnosing a chronic neurodegenerative disease associated with the expression of a HB9 protein in a sample from a subject which comprises: a. obtaining DNA from the sample of the subject suffering from the chronic neurodegenerative disease; b. performing a restriction digest of the DNA with a panel of restriction enzymes; c. separating the resulting DNA fragments by size fractionation; d. contacting the resulting DNA fragments with a nucleic acid probe capable of specifically hybridizing with a unique sequence included within the sequence of a nucleic acid molecule encoding a HB9 protein, wherein the sequence of a nucleic acid molecule encoding a HB9 protein is linked at a specific break point to a specified nucleic acid sequence and labeled with a detectable marker; e. detecting labeled bands which have hybridized to the nucleic acid probe capable of specifically hybridizing with a unique sequence included within the sequence of a nucleic acid molecule encoding a HB9 protein, wherein the sequence of a nucleic acid molecule encoding a HB9 protein is linked at a specific break point to a specified nucleic acid sequence to create a unique band pattern specific to the DNA of subjects suffering from the chronic neurodegenerative disease; f. preparing DNA obtained from a sample of a subject for diagnosis by steps (a–e); and g. comparing the detected band pattern specific to the DNA obtained from a sample of subjects suffering from the chronic neurodegenerative disease from step (e) and the DNA obtained from a sample of the subject for diagnosis from step (f) to determine whether the patterns are the same or different and to diagnose thereby predisposition to the chronic neurodegenerative disease if the patterns are the same.

This invention provides a method for diagnosing a chronic neurodegenerative disease associated with the expression of a HB9 protein in a sample from a subject which comprises: a. obtaining RNA from the sample of the subject suffering from chronic neurodegenerative disease; b. separating the RNA sample by size fractionation; c. contacting the resulting RNA species with a nucleic acid probe capable of specifically hybridizing with a unique sequence included within the sequence of a nucleic acid molecule encoding a HB9 protein, wherein the sequence of a nucleic acid molecule encoding a HB9 protein is linked at a specific break point to a specified nucleic acid sequence and labeled with a detectable marker; d. detecting labeled bands which have hybridized to the RNA species to create a unique band pattern specific to the RNA of subjects suffering from the chronic neurodegenerative disease; f. preparing RNA obtained from a sample of a subject for diagnosis by steps (a–d); and g. comparing the detected band pattern specific to the RNA obtained from a sample of subjects suffering from the chronic neurodegenerative disease from step (d) and the RNA obtained from a sample of the subject for diagnosis from step (f) to determine whether the patterns are the same or different and to diagnose thereby predisposition to the chronic neurodegenerative disease if the patterns are the same.

This invention provides a functionally equivalent analog of HB9 that induces HB9 differentiation of neural progenitor cells.

This invention provides a functionally equivalent analog of HB9 that prevents HB9 differentiation of neural progenitor cells.

This invention provides a method of treating a subject afflicted with a neuromuscular disease which comprises introducing an amount of a pharmaceutical composition comprising a purified HB9 protein and a pharmaceutically acceptable carrier effective to activate acetylcholine to activate muscle cells.

This invention provides a method of treating an embryo afflicted with sacral agenesis which comprises introducing an isolated nucleic molecule encoding a homeobox, HB9, protein.

This invention provides a method of treating an embryo afflicted with sacral agenesis which comprises introducing an amount of a pharmaceutical composition comprising a purified HB9 protein and a pharmaceutically acceptable carrier effective to activate acetylcholine to activate muscle cells.

A method of treating an embryo lacking HB9 expression which comprises introducing an isolated nucleic molecule encoding a homeobox, HB9, protein.

A method of treating an embryo lacking HB9 expression which comprises introducing an amount of a pharmaceutical composition comprising a purified HB9 protein and a pharmaceutically acceptable carrier effective to activate acetylcholine to activate muscle cells.

In order to facilitate an understanding of the Experimental Details section which follows, certain frequently occurring methods and/or terms are best described in Sambrook, et al. (1989).

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

First Set of Experiments

Single-Cell Library Screen

Culture of stage 10 chick (Hamburger and Hamilton, 1951) [i] explants was performed as described (Yamada et al.,1993). After 24 hr, explants were enzymatically dissociated and single cells isolated. The synthesis and amplification of cDNAs isolated from single cells was performed essentially as in Dulac and Axel (1995). Single cell-derived cDNAs were analyzed using Isl1, Isl2, HB9 and Lim2 probes. The efficiency of cDNA amplification was assessed using S17. A single cell cDNA sample that revealed Isl1, Isl2 and HB9 hybridization was used to prepare a cDNA library in λZapII (Stratagene). Approximately 2000 plaques were screened with cDNAs from a motor neuron and Lim2$^+$ neuron. Plaques hybridizing selectively with the motor neuron probe were isolated, cloned and analyzed by in situ hybridization. This screen generated 2 clones that encoded MNR2.

As used herein, "[i] explants" are intermediate neural plate explants.

Isolation of MNR2 and HB9

A single motor neuron-derived MNR2 cDNA clone was used to isolate a longer MNR2 cDNA. A genomic MNR2 clone containing the 5' coding region of MNR2 was ligated to the MNR2 cDNA to generate full-length chick MNR2. A chick HB9 cDNA was isolated from a spinal cord cDNA library using a PCR probe derived from the HB9 homeobox. A full length chick HB9 clone was constructed by ligating genomic HB9 coding sequence to the HB9 cDNA. Genbank accession numbers; chick MNR2 AF066860, chick HB9 AF066861.

Recombinant Retroviral Vectors

As used herein, a recombinant nucleic acid molecule is a nucleic acid molecule which does not occur as an individual molecule in nature and which is obtained through the use of recombinant technology.

Retroviral vectors were generated by subcloning chick cDNAs into either RCASBP(A) or RCASBP(B) vectors (Hughes et al., 1987; Morgan and Fekete, 1996). The RCAS(B) MNR2 3'Δ construct contained the coding region of MNR2 but lacked the 3' non-coding region. Viral supernatants (Morgan and Fekete, 1996) were applied to stage 5–6 chick embryos in ovo. In double infections, viral stocks derived from vectors encoding A or B envelope glycoproteins were mixed prior to in ovo application. Embryos were analyzed at stages 17–27.

Immunocytochemistry and In Situ Hybridization Histochemistry

Rabbit antisera were generated against a GST-chick MNR2 NH$_2$ fusion protein and against a KLH-conjugated chick HB9 NH$_2$ peptide (MEKSKNFRIDALLA). Mouse antisera and monoclonal antibodies were also generated against MNR2 protein and HB9 protein. Rabbit anti-Brn3.0 (Fedtsova and Turner, 1997); guinea pig anti Isl1/2 (Morton and T. M. Jessell unpublished data). For other antibody reagents see Ericson et al., (1997) and Liem et al., (1997). Immunohistochemistry was performed as described (Yamada et al., 1993). Double and triple-label analyses were performed with a Bio-Rad 1024 Confocal Microscope using Cy3, Cy5 and FITC-conjugated secondary antibodies (Jackson, Inc.). In situ hybridization was performed as described (Schaeren-Wiemers and Gerfin-Moser, 199:3; Tsuchida et al., 1994) using MNR2 and ChAT (Yamada, et al., 1993) probes. The 3' non-coding MNR2 probe was the 300 bp SmaI-EcoRI fragment.

BrdU Incorporation into Neural Neurons

BrdU incorporation was analyzed after application of 100 uM BrdU to stage 18 embryos in ovo and subsequent incubation at 37° C. for 30 or 45 minutes.

Retrograde Labeling of Spinal Cord Cells

RCAS(B)MNR2-infected stage 24–26 embryos were dissected, ventral roots exposed and labeled by application of FITC-Dextran (Molecular Probes) (Varela-Echavarria et al., 1996). Embryos were incubated for 1 hour before analysis.

Materials and Methods

Isolation of MNR2

To identify genes expressed by somatic motor neuron progenitors, we performed a PCR-based differential screen (Dulac and Axel, 1995) of individual newly-differentiated motor neurons on the premise that genes expressed by motor neuron progenitors might persist transiently in post-mitotic motor neurons. Chick neural plate ([i]) explants (Yamada et al, 1993) were grown in vitro for 24 h, alone or with a concentration of Shh that induces somatic motor neurons (Ericson et. al. 1997). cDNAs isolated from single cells derived from [i] explants exposed to Shh were hybridized with probes for three homeobox genes Isl1, Isl2 and HB9, that define post-mitotic somatic motor neurons (FIG. 1A). Single cell cDNA samples derived from [i] explants grown alone were hybridized with Lim2, a homeobox gene marker of spinal interneurons (FIG. 1A). A cDNA population amplified from a single Isl1$^+$, Isl2$^+$, HB9$^+$ motor neuron (FIG. 1A) was used to prepare a cDNA library that was screened with probes derived from a single in vitro generated motor neuron or Lim2$^+$ neuron. cDNAs isolated from plaques that hybridized selectively with the motor neuron-derived probe were cloned and sequenced. As used herein, "[i] explants" are intermediate neural plate explants.

Several genes identified in this manner were expressed in a motor neuron restricted pattern and we describe here the function of one of these, MNR2. MNR2 is a homeobox gene that encodes a homeodomain almost identical to that encoded by HB9 (FIG. 1B; Harrison et al., 1994), a gene whose neural expression is restricted to motor neurons (see below, Pfaff et al. 1996, Saha et al., 1997). The MNR2 sequence diverges from HB9 outside the homeodomain (FIG. 1B; data not shown).

MNR2 is Expressed by Somatic Motor Neuron Progenitors

The pattern of neural expression of MNR2 was examined in chick embryos from stages 10 to 25. MNR2 expression was first detected at stage 12 in cells near the floor plate (FIG. 1C). At this stage, no motor neurons have been generated (Langman et al., 1966) and Isl1 is not yet expressed (Ericson et al., 1992). The onset of MNR2 expression coincides with the time that motor neuron progenitors acquire independence from Shh signaling (Ericson et al., 1996). Between stages 15–20, MNR2 expression was restricted to cells in the ventral spinal cord and caudal hindbrain, some of which were located medially and others laterally in a domain that overlaps with post-mitotic Isl1$^+$ motor neurons (FIGS. 1D, 1E; data not shown).

We next examined whether, as predicted by the design of the differential screen, MNR2 is induced by Shh. To test this, [i] explants were exposed to Shh and the expression of MNR2 and Isl1/2 determined. Induction of MNR2 was detected 16 h after exposure to Shh (data not shown) and by 24 h, 70±12 (mean±SEM; n=4) MNR2$^+$ cells were detected (FIGS. 1F, 1G). In addition, 32% of the induced MNR2$^+$ cells did not express Isl1/2 (FIGS. 1G, 1H), consistent with the earlier onset of MNR2 expression in vivo. These results show that Shh induces MNR2.

To provide direct evidence that MNR2 is expressed by mitotic cells, we exposed stage 18 embryos to BrdU for 30 min and monitored the expression of MNR2 and Isl1 by BrdU$^+$ cells. Many MNR2$^+$, BrdU$^+$ cells (FIG. 2A) but no Isl1$^+$, BrdU$^+$ cells (FIG. 2B) were detected. In addition, a subset of MNR2$^+$ progenitors coexpressed the M-phase marker MPM2 (FIG. 2C; Westendorf et al., 1994). MNR2$^+$, progenitors coexpressed Pax6 (FIG. 2D; data not shown) but were located dorsal to the Nkx2.2$^+$ progenitor domain (FIG. 2E), supporting the idea that MNR2 expression is restricted to the progenitors of somatic motor neurons. MNR2 was also detected in post-mitotic somatic motor neurons in the spinal cord and hindbrain but not in visceral motor neurons (FIG. 1E, FIG. 2F and data not shown). Thus, MNR2 expression is restricted to domains of somatic motor neuron generation.

The temporal profile of MNR2 expression was compared with that of other homeodomain proteins that define somatic motor neurons. At spinal cord levels, the initial migration of newly-generated motor neurons occurs in a mediolateral plane (Leber and Sanes, 1995) and thus the more lateral the position of a motor neuron, the more advanced is its state of differentiation. Between stages 15 and 20, MNR2 was detected medially in progenitor cells as well as laterally in post-mitotic motor neurons (FIGS. 2G–K, data not shown). The expression of Isl1 was restricted to post-mitotic motor neurons (FIGS. 2G, 2K; Ericson et al., 1992) but appeared prior to HE9 and Isl2 (FIGS. 2H, 2I, 2K; data not shown). In these laterally positioned motor neurons MNR2 expression was markedly decreased or absent (FIGS. 2H, 2I, 2K) indicating that MNR2 expression is transient. Lim3 is expressed by post-mitotic somatic motor neurons (FIGS. 2J, 2K; Tsuchida et al., 1994) but is also detected in Pax6$^+$ ventral progenitors; and in these cells appears soon after MNR2 (FIGS. 2J, 2K; data not shown). Thus, somatic motor neuron progenitors coexpress Pax6, MNR2 and Lim3.

MNR2 Induces the Expression of Somatic Motor Neuron Transcription Factors

If MNR2 has a critical role in the Shh-induced pathway of motor neuron generation, we reasoned that its misexpression might be sufficient to promote motor neuron differentiation in neural cells that have not been exposed to adequate levels of Shh and perhaps even in dorsal progenitor cells that are exposed to antagonistic BMP signals. To test this idea we misexpressed MNR2 in the neural tube using a replication competent retroviral vector (Morgan and Fekete, 1996). Embryos were infected with MNR2 virus at stages 5–6, permitted to develop until stages 20–27 and the resulting pattern of motor neuron differentiation monitored by expression of Isl1, Isl2, HB9, and Lim3. The expression of Isl2 and HB9 is restricted to somatic motor neurons (Tsuchida et al. 1994; Pfaff et al. 1996; data not shown) whereas Lim3 is also expressed by ventral (V2) interneurons that are generated immediately dorsal to motor neurons (FIGS. 2J, 2K; Ericson et al. 1997). Isl1 is also expressed by dorsal (D2) interneurons (FIGS. 2G, 2K; Liem et al. 1997).

In MNR2-infected embryos examined at stage 23, ectopic MNR2$^+$ cells were detected in a mosaic pattern throughout the spinal cord (FIG. 3A; data not shown). In dorsal regions that contained a high density of MNR2$^+$ cells, many ectopic Isl1$^+$, Isl2$^+$, HB9$^+$ and Lim3 $^+$ cells were detected (FIGS. 3B–E). All ectopic Isl1$^+$, Lim3$^+$, Isl2$^+$ and HB9$^+$ cells coexpressed MNR2 (FIG. 3F; data not shown) indicating that MNR2 acts cell-autonomously to activate the expression of these homeodomain proteins. To control for the specificity of MNR2 activity, we misexpressed Lmx1b and Hoxc6, two other homeobox genes present in the spinal cord (Burke and Tabin 1996; Riddle et al. 1995). Neither Lmx1b nor Hoxc6 induced MNR2, Lim3, Isl1, Isl2 or HB9 (data not shown). Thus, the activity of MNR2 is not mimicked by divergent homeodomain proteins.

We next examined whether the ability of MNR2 to induce motor neuron markers in the dorsal spinal cord is associated with a change in the early dorsal character of neural progenitor cells. The ectopic dorsal expression of MNR2 did not repress Pax7 (FIG. 3G), a marker of dorsal progenitor cells (Ericson et al., 1996). The detection of Isl2$^+$, HB9$^+$ and Lim3$^+$ cells in the extreme dorsal region of the spinal cord (FIGS. 3C–E) also provides evidence that MNR2 can impose a somatic motor neuron character on neural cells that have been exposed to BMP signals (Liem et al., 1997). Consistent with this, there was no dorsoventral restriction in the positions at which cells expressing these ectopic homeodomain protein markers were found (FIGS. 3B–E; data not shown). Ectopic expression of Lim3 and HB9 was also detected in dorsal root ganglion neurons (data not shown), indicating that MNR2 can also activate somatic motor neuron markers in peripheral neurons.

The ability of MNR2 to induce motor neuron transcription factors in the dorsal spinal cord leaves open the issue of whether ventral progenitor cells respond to MNR2 with the expression of motor neuron markers. The detection of a high incidence of MNR2-induced Isl1$^+$, Isl2$^+$ and HB9$^+$ cells below the Pax7 boundary (FIGS. 3B–D, 3G) suggested that this is the case. Nevertheless, it remained possible that the ectopic location of these neurons arose through their dorsal migration from the normal domain of somatic motor neuron generation. We therefore examined whether MNR2 can induce motor neuron transcription factors in ventral progenitor cells generated in neural plate explants. Embryos were infected with MNR2 virus at stages 4–5 and permitted to develop until stage 10, at which time [i] explants were isolated and grown in vitro for 24 h with 0.5 nM Shh. This concentration of Shh is sufficient to repress Pax7 and generate a ventral progenitor cell state (Ericson et al., 1996), but is below the threshold for motor neuron induction (Ericson et: al., 1997). [i] explants isolated from MNR2-infected embryos contained many MNR2$^+$ cells and ~25% of these expressed Isl1/2 (FIGS. 3H, 3I). In contrast, [i] explants derived from uninfected embryos and exposed to 0.5 nM Shh did not generate MNR2$^+$ cells (FIG. 3J) or Isl1/2$^+$ neurons (data not shown; Ericson et al., 1997). These results indicate that MNR2 can also direct motor neuron differentiation in ventral progenitor cells.

MNR2 Acts in the Context of a General Program of Neurogenesis

The expression of motor neuron transcription factors was detected in only a minority of ectopic MNR2$^+$ cells (FIGS. 3A–3F). In considering what might account for this restriction we noted that the ectopic expression of Isl1, Isl2 and HB9 coincided with the location of post-mitotic neurons (FIG. 3 B–E). This observation, taken together with the normal restriction of Isl1, Isl2 and HB9 to post-mitotic motor neurons (FIG. 2K) raised the possibility that the induction of these homeodomain proteins by MNR2 might require cell cycle exit and the acquisition of a generic neuronal character.

To examine this possibility we first determined the proportion of ectopic MNR2$^+$ cells that expressed Cyn1, a marker expressed by all spinal neurons soon after cell cycle exit (Ericson et al., 1997). At stages 20–23, only ~10% of ectopic MNR2$^+$ cells expressed Cyn1 (FIGS. 4A, 4B), indicating that most ectopic MNR2$^+$, are progenitors. In contrast, >98% of MNR2-induced ectopic Isl1$^+$, Isl2$^+$ and $^+$HB9 cells coexpressed Cyn1 (FIGS. 4C–4E; data not shown). These findings suggest that the ectopic induction of Isl1, Isl2 and HB9 by MNR2 requires the acquisition of a post-mitotic neuronal character, thus conforming to the normal profile of expression of these three proteins in somatic motor neurons. Lim3, in contrast, is normally expressed by ventral progenitors as well as by post-mitotic motor neurons. Many MNR2-induced Lim3$^+$ cells could be labeled after a brief BrdU pulse (FIG. 4F), ~70% of MNR2-induced ectopic Lim3$^+$ cells coexpressed Cyn1 (data not shown) and only 55% of MNR2-induced Lim3$^+$ cells coexpressed Isl1 (FIGS. 4E, 4G). Thus MNR2 induces ectopic Lim3 expression in neural progenitors and post-mitotic neurons. These findings show that the normal temporal relationship between cell cycle exit and transcription factor expression is preserved in ectopic MNR2-induced neurons. In a neuronal context then, MNR2 is an efficient inducer of somatic motor neuron transcription factors: 91% of MNR2$^+$, neurons expressed Isl1, 79% expressed Lim3 and ~40% expressed Isl2 and HB9 (FIG. 4H).

MNR2 Expression is Autoregulated

The onset of MNR2 expression occurs at the time that motor neuron progenitors attain independence from Shh signaling (Ericson et al., 1996). This finding raises the possibility that the progression of motor neuron progenitors to a Shh-independent state involves the expression of MNR2. One mechanism by which MNR2 might establish Shh-independence is through the activation of its own expression.

To test this, we infected embryos with a MNR2 3'Δ construct lacking 3' non-coding sequence and monitored the expression of endogenous MNR2 using a 3' non-coding probe. Retrovirally-introduced MNR2 3'Δ induced endogenous MNR2 in dorsal spinal cord cells (FIGS. 4I, 4J). Moreover, the ectopic expression of MNR2 was not restricted to neural cells (FIG. 4J), in contrast to the neural restriction in the MNR2-induced ectopic expression of Lim3, Isl1, Isl2 and HB9 (FIG. 3; data not shown). These results support the idea that MNR2 expression and autoactivation underlies the progression of motor neuron progenitors to a Shh-independent state.

MNR2 Induces Later Features of Motor Neuron Differentiation

The sufficiency of MNR2 as an inducer of somatic motor neuron transcription factors prompted us to examine whether these neurons exhibit other aspects of the motor neuron phenotype. We first examined if MNR2 can induce the expression of ChAT, the gene encoding the rate limiting enzyme in the synthesis of acetylcholine, the motor neuron neurotransmitter. In control embryos, ChAT expression was restricted to the region occupied by motor neuron cell bodies and their dendrites (FIGS. 5A, 5C, 5E). In contrast, in MNR2-infected embryos, ChAT was expressed ectopically by cells in the dorsal spinal cord (FIGS. 5B, 5D, 5E). Thus, MNR2 induces the gene that defines the transmitter phenotype of motor neurons.

We next examined whether neurons in the dorsal spinal cord that express MNR2 acquire the motor neuron-specific feature of an axonal projection into the ventral root. To assess this we labeled spinal neurons retrogradely by application of FITC-Dextran to the ventral roots of stage 25 embryos. In control embryos, labeled neurons were restricted to the ventral spinal cord (FIGS. 5F, 5J). In MNR2-infected embryos, many ectopic dorsal MNR2$^+$, Isl1/2$^+$ neurons were labeled with FITC-Dextran and these neurons projected axons towards the ventral root exit point (FIGS. 5G–J). In addition, ectopic expression of SC1, a surface marker of motor neurons (Tanaka and Obata, 1984) was detected in MNR2-infected but not in control embryos (data not shown). These findings show that MNR2 induces later phenotypic features of somatic motor neurons.

Ectopic Expression of MNR2 Represses Interneuron Fates

The detection of ectopic motor neuron differentiation in dorsally-located neurons raised the question of whether the interneuronal character of spinal cord neurons is suppressed by MNR2. To address this issue we analyzed the expression of homeodomain proteins that define four classes of interneurons generated in domains dorsal to motor neurons. Dorsally, D1 neurons express LH2 (Liem et al., 1997) and many D2 neurons express Brn3.0 (Fedtsova and Turner, 1997). Ventrally, V1 neurons express En1 (Ericson et al., 1997) and Lim3$^+$ V2 neurons express Chx10 (Ericson et al. 1997).

In MNR2-infected embryos D1, D2, V1 or V2 interneuron markers were not detected in ectopic Isl2$^+$ and HB9$^+$ neurons (data not shown). In regions of the spinal cord in which a high proportion of cells in these interneuron domains ectopically expressed MNR2 there was a ~50–90% decrease in the number of cells that expressed D1, D2, V1 and V2 neuron markers (Table 1).

TABLE 1

Suppression of Spinal Interneuron Fates by MNR2

| Interneuron Population | Homeodomain Protein Marker | Reduction in Marker Expression |
|---|---|---|
| D1 | LH2 | 75% (1) |
| D2 | Brn3.0 | 88 ± 4% (4) |
| V1 | En1 | 46 ± 5% (10) |
| V2 | Chx10 | 89 ± 3% (9) |

Analysis derived from spinal cord of a stage 22 MNR2-infected embryo in which ectopic MNR2$^+$ cells were restricted almost exclusively to the right half of the spinal cord. Values (%) indicate number of labeled cells on heavily infected vs uninfected sides. Mean ±SEM, n = number of sections. A similar repression of interneuron markers was detected in six other MNR2-infected embryos.

The differing degrees of extinction of these interneuron markers appear to reflect local variation in the density of ectopic MNR2$^+$ cells rather than any difference in the efficiency with which MNR2 suppresses individual interneuron fates. The induction of somatic motor neuron differentiation by MNR2 is therefore accompanied by the suppression of interneuron fates.

Cooperation of Isl1 and MNR2 in the Specification of Somatic Motor Neuron Identity We next addressed the contributions of the transcription factors induced by MNR2 to the differentiation of somatic motor neurons. To examine the role of Isl1 in the program of somatic motor neuron differentiation we assayed motor neuron markers in embryos infected with Isl1 virus. No ectopic expression of MNR2, Lim3, Isl2 or HB9 was detected (FIGS. 6A–6E). Thus, Isl1 is not sufficient to direct somatic motor neuron differentiation. Nevertheless, all MNR2-induced ectopic dorsal Isl2$^+$ and HB9$^+$ coexpressed Isl1 (FIG. 4E). This observation, together with the requirement for Isl1 in the generation of somatic motor neurons (Pfaff et al., 1996) suggested that the ectopic expression of Isl2 and HB9 induced by MNR2 involves Isl1.

To test this we analyzed the activity of MNR2 at an earlier stage of development (stage 20). We reasoned that if Isl1 cooperates with MNR2 in the induction of Isl2 and HB9, then the early onset of Isl1 expression by prospective D2 neurons (Liem et al., 1997) might relieve the delay inherent in the induction of Isl1 by MNR2 and thus accelerate MNR2-induced motor neuron differentiation. MNR2 induced ectopic dorsal expression of Isl2 and HB9 at stage 20 (FIGS. 6F–6J). However there was a restriction in the position of ectopic Isl2$^+$ and HB9$^+$ cells, focused on the normal domain of D2 neuron generation (FIGS. 6F–6J, 6P). If this restriction is conferred by the early expression of Isl1 by prospective D2 neurons then coinfection with MNR2 and Isl1 viruses would be expected to abolish the dorsoventral restriction in Isl2 and HB9 expression. In the spinal cord of embryos coinfected with MNR2 and Isl1 viruses and analyzed at stage 20, a high proportion of cells now coexpressed MNR2 and Isl1 at ectopic locations (FIG. 6K). Over 70% of these cells coexpressed Isl2 and/or HB9 (FIG. 6N). Moreover, the dorsoventral restriction in the position of ectopic Isl2$^+$ and HB9$^+$ neurons evident after MNR2 infection was abolished (FIGS. 6L, 6M, 6P). These findings support the idea that the induction of Isl2 and HB9 by MNR2 involves the cooperation of Isl1.

MNR2 Acts Upstream of Lim3 in the Specification of Somatic Motor Neurons

During normal somatic motor neuron differentiation, Lim3 and MNR2 are expressed by ventral progenitors at a similar developmental stage (FIGS. 2J, 2K). To determine the hierarchy of MNR2 and Lim3 activity, we misexpressed Lim3 and assayed the resulting pattern of homeodomain protein expression Lim3 did not induce MNR2 or Isl2 (FIGS. 7A–7E) nor did it increase the number of dorsal Isl1$^+$ neurons (FIGS. 7D, 7E). However, there was a very low incidence of ectopic HB9$^+$ neurons in the dorsal spinal cord of Lim3-infected embryos (FIG. 7D, 7E) confined exclusively to cells that coexpressed Isl1 (FIG. 7D; data not shown).

The restriction of ectopic HB9 expression to dorsal Isl1$^+$ neurons in Lim3-infected embryos raised the possibility that the coordinate activities of Lim3 and Isl1 are sufficient to induce HB9 expression. To test this we coinfected embryos with Lim3 and Isl1 viruses (FIG. 7H). The incidence of is ectopic expression of HB9 was markedly increased in the spinal cord of such coinfected embryos, compared to embryos infected solely with Lim3 (FIGS. 7J, 7K). Moreover, >30% of cells that coexpressed Lim3 and Isl1 expressed HB9 (FIG. 7K) and these HB9$^+$ neurons were not restricted to any dorsoventral position (FIG. 7J; data not shown). In contrast, ectopic expression of Isl2 was rarely detected after Lim3 and Isl1 coinfection (FIGS. 7I, 7K; data not shown). These results provide evidence that Lim3 and Isl1 cooperate as intermediaries in the MNR2-induced activation of HB9 expression.

HB9 Activity and the Maintenance of Transcription Factor Expression by Somatic Motor Neurons The expression of MNR2 is transient, raising the issue of how the expression of Lim3, Isl1 and Isl2 is maintained in post-mitotic motor neurons. The HB9 gene encodes a homeodomain protein closely related to MNR2, suggesting that HB9 has an activity similar to that of MNR2. To test this we infected embryos with an HB9 virus and monitored the ectopic expression of Isl1, Isl2 and Lim3. HB9 induced the expression of Isl1, Isl2 and Lim3 at an efficiency similar to that of MNR2 (FIGS. 7L–N; data not shown). Misexpression of HB9 also induced the ectopic expression of MNR2 (data not shown), a result that we interpret to reflect mimicry of the autoregulatory activity of MNR2. These results suggest a role for HB9 in maintaining of the differentiated properties of somatic motor neurons at times after MNR2 expression has been extinguished.

Lim3 Expression in the Absence of MNR2 is Sufficient to Induce the V2 Interneuron Fate Lim3 is also expressed by V2 neurons and appears prior to the V2 marker Chx10 (Ericson et al., 1997). We therefore examined whether Lim3 has a role in the differentiation of this interneuron subtype. To test this, we examined the pattern of Chx10 expression in the spinal cord of Lim3-infected embryos. Misexpression of Lim3 induced Chx10 in Cyn1$^+$ neurons located at both dorsal and extreme ventral regions of the spinal cord, adjacent to the floor plate (FIGS. 7F, G; data not shown) but not in somatic motor neurons (FIG. 7G). These results suggest that the expression of Lim3 in cells devoid of MNR2 activity is sufficient to direct the differentiation of V2 interneurons.

Discussion

Graded Shh signaling appears to control the identity of neuronal subtypes in the ventral neural tube. The present studies show that Shh induces the expression of a homeodomain protein, MNR2, in motor neuron progenitors and that the expression of MNR2 is sufficient to direct somatic motor neuron differentiation. Thus, MNR2 expression appears to be a critical output of Shh signaling in the pathway of somatic motor neuron generation. We discuss these findings in the context of the Shh signaling pathways involved in neuronal fate determination and the control of progenitor cell identity and commitment in the vertebrate CNS.

MNR2 Expression Specifies Somatic Motor Neuron Progenitors

Shh signaling is required for the generation of somatic motor neurons, but the downstream steps in this developmental program have not been resolved. Somatic motor neurons derive from PaxG$^+$ progenitor cells, yet Pax6 itself appears to be required only indirectly for somatic motor neuron generation (Ericson et al., 1997). Our results suggest that the expression of MNR2 by Pax6$^+$ progenitors is a key step in somatic motor neuron development, specifying ventral cells as motor neuron progenitors.

At what step in the pathway of somatic motor neuron differentiation does MNR2 act? MNR2 is expressed by ventral progenitor cells ~4–5 h prior to the generation of the first post-mitotic motor neurons and the cell cycle time of ventral progenitor cells is ~8 h (Langman et al., 1966). Thus, it appears that MNR2 expression is initiated during the final division cycle of motor neuron progenitors. The onset of MNR2 expression by motor neuron progenitors coincides with the time that they attain independence of Shh signaling (Ericson et al., 1996). This observation and the ability of MNR2 to activate its own expression provide a potential molecular basis for the transition of Shh-dependent ventral progenitor cells into Shh-independent, committed somatic motor neuron progenitors.

MNR2 is induced rapidly by Shh, prior to the expression of other somatic motor neuron transcription factors. It is unclear, however, if MNR2 is a direct target for the conserved Hedgehog (Hh) signal transduction pathway mediated by the Ci/Gli class of transcription factors (Ingham, 1995). Gli proteins have been implicated in floor plate differentiation (Lee et al., 1997; Hynes et al., 1997; Ding et al., 1998; Matise et al., 1998) but it is uncertain whether they are also involved directly in the generation of motor neurons.

MNR2 and the Transcriptional Hierarchy of Motor Neuron Differentiation

The expression of MNR2 in neural progenitor cells appears sufficient to induce somatic motor neurons. Moreover, the ability of MNR2 to direct motor neuron differentiation appears to be independent of the position of progenitor cells within the neural tube. Most strikingly, MNR2 promotes somatic motor neuron differentiation both in ventral progenitors that have been exposed to inadequate levels of Shh and in dorsal progenitor cells that have been exposed to BMP signals (Liem et al., 1997). Since exposure of progenitors to BMPs inhibits motor neuron generation (Basler, et: al., 1993), these findings implicate MNR2 as a determinant of somatic motor neuron identity.

MNR2 appears to function upstream of a set of LIM homeodomain transcription factors that cooperate to specify somatic motor neuron identity (FIG. 8). Lim3 is expressed soon after MNR2 in motor neuron progenitors. Ectopic expression of MNR2 induces Lim3 expression but Lim3 does not induce MNR2, suggesting that MNR2 functions upstream of Lim3 in motor neuron progenitors. However, Lim3 is also expressed by V2 neurons that appear to derive from MNR2$^-$ progenitors, implying the existence of an MNR2-independent pathway for the activation of Lim3 expression. This parallel pathway could also operate in somatic motor neuron progenitors.

MNR2 efficiently induces the expression of Isl1 in spinal neurons. The induction of Isl1 may be a key step in somatic motor neuron differentiation, since the later appearance of transcription factors specific to somatic motor neurons, Isl2 and HB9, appears to require the expression of Isl1. The role of Isl1 inferred from these gain-of-function studies is consistent with the loss of somatic motor neuron differentiation in mice lacking Isl1 function (Pfaff et al., 1996). Isl1 is also required for the generation of visceral motor neurons (Pfaff et al., 1996). Since MNR2 is not expressed by Nkx2.2$^+$ visceral motor neuron progenitors, the expression of Isl1 in visceral motor neurons appears to be regulated by a factor other than MNR2. A dorsal expansion in the domain of Nkx2.2 expression results in a switch from somatic to visceral motor neuron generation (Ericson et al., 1997) suggesting that Nkx2.2 or related Nkx genes (Pabst et al., 1998) promote visceral motor neuron identity.

Lim3 and Isl1 appear to cooperate in certain of the downstream steps of somatic motor neuron differentiation, their actions being sufficient to induce HB9 but not Isl2. Indeed, biochemical evidence indicates that Isl1 and Lim3 can interact directly (Jurata et al., 1998). Different intermediary pathways may therefore control the expression of distinct components of the somatic motor neuron phenotype (FIG. 8). Although the coexpression of MNR2 and Isl1 can induce Isl2 expression, Lim3 is induced by MNR2 and thus may also participate in the induction of Isl2 expression. HB9 possesses an activity similar to that of MNR2 but appears only in post-mitotic neurons and thus may function to maintain somatic motor neuron properties after the expression of MNR2 has been extinguished.

The expression of Lim3 in a cellular context devoid of MNR2 results in the activation of Chx10, a definitive marker of V2 neurons. Lim3 many therefore function in the normal program of generation of both somatic motor neurons and V2 neurons. Misexpression of MNR2 in the V2 interneuron domain represses the expression of Chx10 while promoting somatic motor neuron differentiation. Thus the restriction in the domain of MNR2 expression imposed by graded Shh signaling may underlie the decision of ventral progenitors to differentiate into somatic motor neurons or V2 neurons.

MNR2 Functions in Conjunction with an Independent Neurogenic Program

The activity of MNR2 in inducing somatic motor neuron differentiation appears to operate within the context of a broader program of neurogenesis. Ectopic MNR2 induces the expression of Lim3 in progenitor cells but induces Isl1, Isl2 and HB9 only in post-mitotic neurons, consistent with the normal temporal appearance of these proteins in somatic motor neurons. Thus, neural progenitors appear unable to express post-mitotic somatic motor neuron markers even though MNR2 is expressed precociously in these cells.

The timing of differentiation of vertebrate neurons appears to be controlled by the sequential activation of basic HLH proteins with neurogenic properties (Anderson and Jan, 1997; Lo et al., 1998). The expression of certain of these bHLH genes is initiated at the time that progenitor cells exit the cell cycle and acquire overt neuronal character (Begley et al., 1992; Roztocil et al., 1997). An independently-regulated program of expression of neurogenic bHLH proteins might therefore limit the ability of MNR2 to induce the expression of Isl1, Isl2 and HB9 to post-mitotic neurons.

A Single Transcription Factor Specifies an Individual Neuronal Subtype

Our results provide some insight into the question of whether neuronal subtype identities in the developing vertebrate CNS are controlled by the actions of dedicated neuronal subtype-specific determinants. Studies of cell fate determination during vertebrate myogenesis and *Drosophila* eye development have revealed the existence of transcriptional cascades that can be activated by the expression of a single transcription factor (Weintraub, 1993; Halder et al., 1995; Chen et al., 1997; Pignoni et al., 1997). Our results indicate that one neuronal subtype generated in the vertebrate CNS, somatic motor neurons, can similarly be specified by the actions of a single homeodomain transcription factor, MNR2. Moreover, in a neuronal context devoid of MNR2 activity, Lim3 appears sufficient to specify V2 interneuron fates. The differentiation of floor plate cells can also be specified by a single transcription factor, the winged helix protein HNF3β (Ruiz i Altaba et al., 1993; 1995; Sasaki and Hogan 1994).

The identification of transcription factors that direct the generation of two distinct classes of neurons in the ventral spinal cord raises the possibility that the identity of neurons in other regions of the CNS are similarly determined by the activity of individual subtype-dedicated transcription factors. The identification of such factors might permit the direction of progenitor cells along specific pathways of neuronal differentiation in the absence of constraints imposed by their prior developmental history.

References of the Experiments

Anderson, D. J. and Jan, Y. N. (1997). The determination of the neuronal phenotype. In Molecular and Cellular Approaches to Neural Development, Eds. Cowan, W. M., Jessell, T. M., and Zipursky, S. L. Oxford University Press, New York, Oxford pp 26–63.

Bang, A. G., and Goulding, M. D. (1996). Regulation of vertebrate neural cell fate by transcription factors. Curr. Opin. Neurobiol. 6, 25–32.

Basler, K., Edlund, T., Jessell, T. M., and Yamada, T. (1993). Control of cell pattern in the neural tube: regulation of cell differentiation by dorsalin-1, a novel TGF beta family member. Cell 73, 687–702.

Begley, C. G., Lipkowitz, S., Gobel, V., Mahon, K. A., Bertness, V., Green, A. R., Gough, N. M., and Kirsch, I. R. (1992). Molecular characterization of NSCL, a gene encoding a helix-loop-helix protein expressed in the developing nervous system. Proc. Natl. Acad. Sci. USA 89, 38–42.

Burke, A. C., and Tabin, C. J. (1996). Virally mediated misexpression of Hoxc-6 in the cervical mesoderm results in spinal nerve truncations. Dev. Biol. 178, 192–197.

Chen, R., Amoui, M., Zhang, Z, and Mardon, G. (1997). Dachshund and eyes absent proteins form a complex and function synergistically to induce ectopic eye development in *Drosophila*. Cell 91, 893–903.

Chiang, C., Litingtung, Y., Lee, E., Young, K. E., Corden, J. L., Westphal, H., and Beachy, P. A. (1996). Cyclopia and defective axial patterning in mice lacking Sonic Hedgehog gene function. Nature 383, 407–413.

Ding, Q, Motoyama, J., Gasca, S., Mo, R., Sasaki, H. Rossant, J., and Hui, C. C. (1998). Diminished sonic hedgehog signaling and lack of floor plate differentiation in Gli2 mutant mice. Development 125, 2533–2543.

Dulac, C., and Axel, R. (1995). A novel family of genes encoding putative pheromone receptors in mammals. Cell 83, 195–206.

Ericson, J., Thor, S., Edlund, T., Jessell, T. M., and Yamada, T. (1992). Early stages of motor neuron differentiation revealed by expression of homeobox gene Islet-1. Science 256, 1555–60.

Ericson, J., Morton, S., Kawakami, A., Roelink, H., and Jessell, T. M. (1996). Two critical periods of sonic hedgehog signaling required for the specification of motor neuron identity. Cell 87, 661–673.

Ericson, J., Rashbass, P., Schedl, A., Brenner-Morton, S., Kawakami, A., van Heyningen, V., Jessell, T. M., and Briscoe, J. (1997). Pax6 controls progenitor cell identity and neuronal fate in response to graded Shh signaling. Cell 90, 169–180.

Fedtsova, N., and Turner, E. E. (1997). Inhibitory effects of ventral signals on the development of Brn-3.0-expressing neurons in the dorsal spinal cord. Dev. Biol. 190, 18–31.

Halder, G., Callaerts, P. and Gehring, W. J. (1995). Induction of ectopic eyes by targeted expression of the eyeless gene in *Drosophila*. Science 267, 1788–1792.

Hamburger, H., and Hamilton, H. (1951). A series of normal stages in the development of the chick embryo. J. Morphol. 88, 49–92.

Harrison, K. A., Druey, K. M., Deguchi, Y., Tuscano, J. M., and Kehrl, J. H. (1994). A novel human homeobox gene distantly related to proboscipedia is expressed in lymphoid and pancreatic tissues. 269, 19968–19975.

Hynes, M., Stone, D. M., Dowd M., Pitts-Meek, S., Goddard, A., Gurney, A., and Rosenthal, A. (1997). Control of cell pattern in the neural tube by the zinc finger transcription factor and oncogene Gli-1. Neuron 19, 15–26.

Hughes, S. H., Greenhouse, J. J., Petropoulos C. J., and Sutrave, P. (1987). Adaptor plasmids simplify the insertion of foreign DNA into helper-independent retroviral vectors. J. Virol. 61, 3004–3012.

Ingham, P. W. (1995). Signaling by hedgehog family proteins in *Drosophila* and vertebrate development. Curr. Opin. Genet Dev. 5, 492–498.

Jurata, L. W., Pfaff, S. L., Gill G. N. (1998). The nuclear LIM domain interactor NLI mediates homo-and heterodimerization of Lim domain transcription factors. J. Biol. Chem. 273, 3152–3157.

Langman, J., Guerrant, R. L., and Freeman, B. G. (1966). Behavior of neuroepithelial cells during closure of the neural tube. J. Comp. Neurol. 127, 399–411.

Leber, S. M., and Sanes, J. R. (1995). Migratory paths of neurons and glia in the embryonic chick spinal cord. J. Neurosci. 15, 1236–1248.

Lee, J., Platt, K. A., Censullo, P., and Ruiz i Altaba, A. (1997). Gli1 is a target of Sonic hedgehog that induces ventral neural tube development. Development 124, 2537–2552.

Liem, K. F. Jr, Tremml, G., and Jessell, T. M. (1997). A role for the roof plate and its resident TGFbeta-related proteins in neuronal patterning in the dorsal spinal cord. Cell 91, 127–138.

Lo L, Tinveron M. C., and Anderson D. J. (1998). MASH1 activates expression of the paired homeodomain transcription factor Phox2a, and couples pan-neuronal and subtype-specific components of autonomic neuronal identity. Development 125 609–620.

Lumsden, A., and Krumlauf, R. (1996). Patterning the vertebrate neuraxis. Science 274, 1109–1115.

Marti, E., Bumcrot, D. A., Takada, R., and McMahon, A. P. (1995). Requirement of 19K form of sonic hedgehog for induction of distinct ventral cell types. Nature 375, 322–325.

Matise M. P., Epstein D. J., Park H. L., Platt K. A. and Joyner A. L. (1998). Gli2 is required for induction of floor plate and adjacent cells, but not most ventral neurons in the mouse central nervous system. Development 125 2759–2770.

Morgan, B. A. and Fekete, D. M. (1996). Manipulating gene expression with replication-competent retroviruses. Methods Cell Biol. 51, 185–218.

Osumi, N., Hirota, A., Ohuchi, H., Nakafuku, M., Imura, T., Kuratani, MS., Fujiwara, M., Noji, S., and Eto, K. (1997). Pax-6 is involved in specification of the hindbrain motor neuron subtype. Development 124, 2961–2972.

Pabst, O., Herbrand, H., and Arnold, H. H. (1998). Nkx2-9 is a novel homeobox transcription factor which demarcates ventral domains in the developing mouse CNS. Mech. Dev. 73, 85–93.

Pattyn, A., Morin, X., Cremer, H., Goridis, C., and Brunet, J. F. (1997). Expression and interactions of the two closely related homeobox genes Phox2a and Phox2b during neurogenesis. Development 124, 4065–4075.

Pfaff, S. L., Mendelsohn, M., Stewart, C. L., Edlund, T., and Jessell, T. M. (1996). Requirement for LIM homeobox gene Isl1 in motor neuron generation reveals a motor neuron-dependent step in interneuron differentiation. Cell 84, 309–320.

Pfaff, S., and Kintner, C. (1998). Neuronal diversification: development of motor neuron subtypes. Curr. Opin. Neurobiol. 8, 27–36.

Pignoni, F., Hu, B., Zavitz, K. H., Xiao, J., Garrity, P. A., and Zipursky, S. L. (1997). The eye-specification proteins So and Eya form a complex and regulate multiple steps in *Drosophila* eye development. Cell 91, 881–891.

Riddle, R. D., Ensini, M., Nelson, C., Tsuchida, T., Jessell, T. M., and Tabin, C. (1995). Induction of the LIM homeobox gene Lmx1 by WNT7 a establishes dorsoventral pattern in the vertebrate limb. Cell 83, 631–640.

Roelink, H., Porter, J. A., Chiang, C., Tanabe, Y., Chang, D. T., Beachy, P. A., and Jessell, T. M. (1995). Floor plate and motor neuron induction by different concentrations of the amino-terminal cleavage product of sonic hedgehog autoproteolysis. Cell 81, 445–455.

Roztocil, T., Matter-Sadzinski, L., Alliod, C., Ballivet, M., and Matter, J. M. (1997). NeuroM, a neural helix-loop-helix transcription factor, defines a new transition stage in neurogenesis. Development 124, 3263–3272.

Ruiz i Altaba, A., Cox, C., Jessell, T. M., and Klar, A. (1993). Ectopic neural expression of a floor plate marker in frog embryos injected with the midline transcription factor Pintallavis. Proc. Natl. Acad. Sci. USA 90, 8268–8272.

Ruiz i Altaba, A., Jessell, T. M., and Roelink, H. (1995). Restrictions to floor plate induction by hedgehog and winged-helix genes in the neural tube of frog embryos. Mol. Cell Neurosci. 6, 106–121.

Saha, M. S., Miles, R. R., and Grainger, R. M. (1997). Dorsal-ventral patterning during neural induction in Xenopus: assessment of spinal cord regionalization with xHB9, a marker for the motor neuron region. Dev. Biol. 187, 209–223.

Sasaki, H., and Hogan, B. L. (1994). HNF-3 beta as a regulator of floor plate development. Cell 76, 103–115.

Schaeren-Wiemers, N. and Gerfin-Moser, A. (1993). A single protocol to detect transcripts of various types and expression levels in neural tissue and cultured cells: in situ hybridization using digoxigenin-labelled cRNA probes. Histochemistry 100, 431–440.

Tanabe, Y., Roelink, H., and Jessell, T. M. (1995). Induction of motor neurons by sonic hedgehog is independent of floor plate differentiation. Curr. Biol. 5, 651–658.

Tanabe, Y., and Jessell, T. M. (1996). Diversity and pattern in the developing spinal cord. Science 274, 1115–1123.

Tanaka, H., and Obata, K. (1984). Developmental changes in unique cell surface antigens of chick embryo spinal motor neurons and ganglion cells. Dev. Biol. 106, 26–37.

Tsuchida, T., Ensini, M., Morton, S. B., Baldassare, M., Edlund, T., Jessell, T. M., and Pfaff, S. L. (1994). Topographic organization of embryonic motor neurons defined by expression of LIM homeobox genes. Cell 79, 957–70.

Varela-Echavarria, A., Pfaff, S. L., and Guthrie, S. (1996). Differential Expression of LIM homeobox genes among motor neuron subpopulations in the developing chick brain stem. Mol. Cell. Neurosci. 8, 242–257.

Weintraub, H. (1993). The MyoD family and myogenesis: redundancy, networks, and thresholds. Cell 75, 1241–1244.

Westendorf, J. M., Rao, P. N., and Gerace, L. (1994). Cloning of cDNAs for M-phase phosphoproteins recognized by the MPM2 monoclonal antibody and determination of the phosphorylated epitope. Proc. Natl. Acad. Sci. USA 91, 714–718.

Yamada, T., Pfaff, S. L., Edlund, T., and Jessell, T. M. (1993). Control of cell pattern in the neural tube: motor neuron induction of diffusible factors from notochord and floor plate. Cell 73, 673–86.

Second Set of Experiments

Results

HB9 Expression in Developing Motor Neurons

Figures 14A, 14B, 14C, 14D:
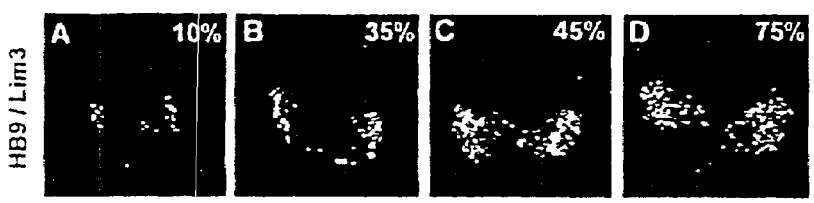
Figures 14E, 14F, 14G, 14H:
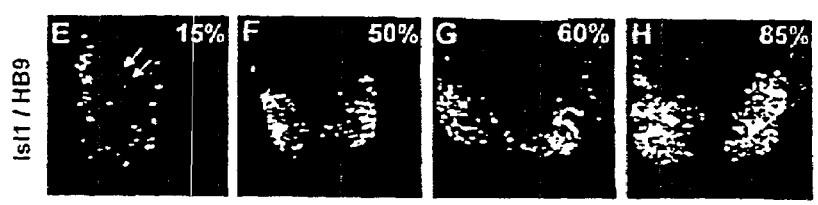

To begin to define the role of HB9 in the early development of MNs, we compared the pattern of HB9 expression with that of three other early MN markers, the LIM-HD proteins Lim3 (Lhx3), Isl1 and Isl2. In the mouse spinal cord and caudal hindbrain, the first post-mitotic MNs are detected at e9.0 to e9.5 and MN genesis is complete by e10.5–e11.0 (Nornes and Carry, 1978; FIG. 16A; our unpublished data). Expression of HB9 was first detected in the spinal cord at e9.25 to e9.5 (FIG. 14; data not shown). During the early phase of MN generation (when 10–25% of the total number of MNs destined to form at a specific axial level have been generated), the expression of HB9 was largely coincident with that of Lim3 (FIG. 14A; data not shown), and HB9+/Lim3+ cells that lacked Isl1 expression could also be detected (FIG. 14E). However, during the peak period of MN generation (25–60% of total MN number), many medially located Lim3 cells lacked HB9 expression (FIGS.

14B–D) and the expression of HB9 and Isl1 coincided in virtually all cells (FIGS. 14F–H). At e10.0, near to the completion of the period of MN generation (60–85% motor neuron genesis), HB9 and Isl1 expression also coincided, but by this stage many of the more lateral and thus more mature HB9 cells had lost Lim3 expression (see FIGS. 17A, E). Within the developing spinal cord, HB9 expression was detected in all MNs, regardless of their eventual somatic or visceral subclass identity (data not shown). However, a more selective profile of HB9 expression was detected at caudal hindbrain levels. Here, HB9 expression was restricted to somatic MNs of the hypoglossal nucleus and no expression was detected in cranial level MNs of visceral identity (data not shown, but see Briscoe et al., 1999). Notochord cells also transiently expressed HB9, from e8.5 to e9.5 (FIGS. 14A–D; data not shown).

Figures 14I, 14J, 14K, 14L:
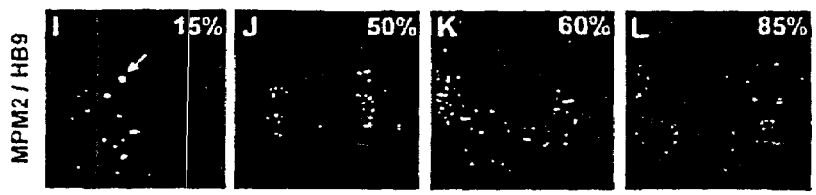
Figures 14M, 14N, 14O, 14P:
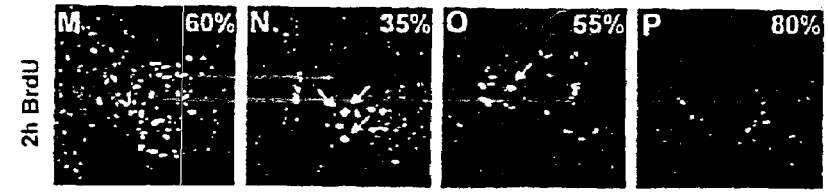

Comparison of the patterns of expression of Lim3, HB9 and Isl1 raised the issue of the relationship between the time of onset of HB9 expression and the exit of MNs from the cell cycle. To assess this issue we determined over the period e9.5 to e10.0 the incidence of overlap in expression of HB9 with MPM2, a marker of M phase cells (Westendorf et al., 1994), and with cells labeled by a brief BrdU pulse. The incidence of coexpression of MPM2 and HB9 by individual cells varied markedly according to the fraction of total number of MNs generated at particular axial levels of the spinal cord. We focused our quantitative analysis of HB9 and MPM2 expression at caudal cervical levels of the spinal cord. The incidence of MPM2/HB9 coexpression was greatest in younger (e9.5) embryos in which only 10–25% of the total number of MNs had been generated (FIG. 14I; data not shown). In slightly older (e9.75) embryos, when MN generation was approaching its peak (25–60% of motor neurons generated), very few MPM2/HB9 colabelled cells were detected (FIGS. 14J–L). During the later phase (e10.0) of motor neuron generation (>60% motor neurons generated), few if any HB9 cells coexpressed MPM2 (data not shown). BrdU labeling analysis of e9.5 to e10.0 embryos revealed that at early stages of motor neuron genesis, BrdU$^+$/HB9$^+$ cells could be detected (FIG. 14N), but during the peak and late periods of motor neuron genesis, the number of BrdU$^+$/HB9$^+$ cells decreased markedly (FIGS. 14O, P). In contrast, many BrdU$^+$/Lim3$^+$ cells were detected in the ventral domain of motor neuron generation throughout the entire period of motor neuron genesis (FIG. 14M; data not shown). These data indicate that HB9 is expressed by some Lim3$^+$ MN progenitors during the early phase of MN genesis, but also suggest that during the peak period of MN genesis, many cells initiate HB9 expression after the onset of Lim3 expression and coincident with the onset of Isl1 expression$_1$ apparently as they acquire a post-mitotic state.

Generation of Hb9 Mutant Mice

To examine the role of Hb9 in early MN development, we generated targeted alleles of Hb9 by homologous recombination in mouse ES cells. Three Hb9 alleles were generated, each containing a pgk-Neo gene and cDNAs encoding different marker proteins under the control of an IRES sequence (Ghattas et al., 1991; Mombaerts et al., 1996) (FIG. 15A, Bii–iv): i/ an SV40 nuclear localization signal (nls) fusion with lacZ (Hb9$^{nlslacZ}$) (FIG. 15D), ii/ a tau fusion with lacZ (Hb9$^{taulacZ}$) (FIGS. 15E, F) and iii/ a tau fusion with a multimerized myc epitope (Hb9$^{taumyc}$) (data not shown; see FIG. 18K). Mice homozygous for each of the targeted alleles were born at normal Mendelian frequencies (Table 1) but died at or soon after birth (data not shown). The cause of death has not been defined but may involve respiratory failure, since the lungs of Hb9 mutant neonates were not inflated (data not shown).

TABLE 1

Generation of Mutant Embryos

| | Number of Litters | Number of Embryos | Genotype | | |
|---|---|---|---|---|---|
| | | | +/+ | +/− | −/− |
| Hb9 nclazZ | 14 | 88 | 27 | 40 | 21 |
| Hb9 taumyc | 6 | 44 | 12 | 22 | 10 |
| Hb9$^{taulacZ}$ | 6 | 41 | 9 | 22 | 10 |
| Total | 26 | 173 | 48 | 84 | 41 |

Figure 15A:
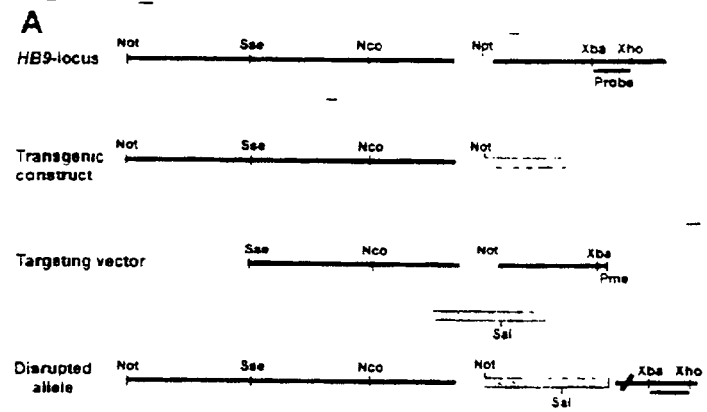
Figure 15B:
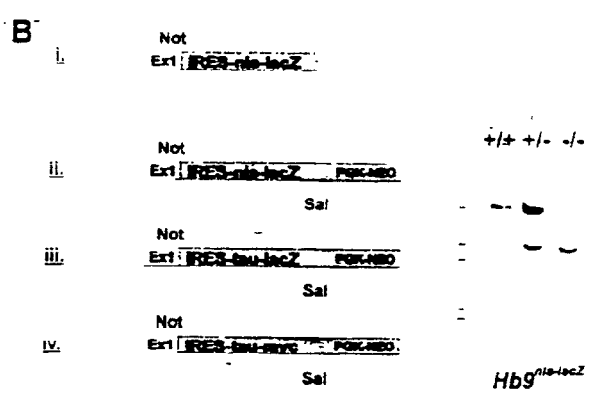
Figures 15C, 15D, 15E, 15F:
Figures 15G, 15H, 15I:
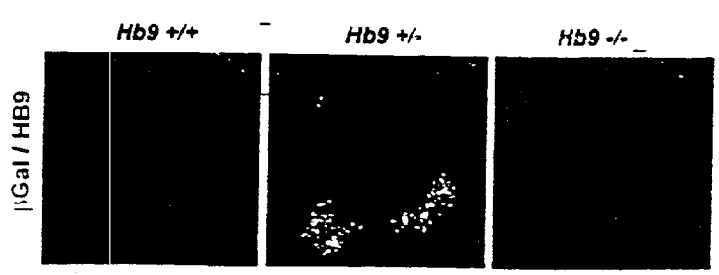

To determine whether the targeted Hb9 alleles represented null mutations, we examined the expression of HB9 in heterozygous and homozygous mutant embryos at e10.5. In the spinal cord of heterozygous Hb9$^{nlslacZ}$ embryos, the expression of lacZ and HB9 coincided (FIGS. 15F, G). In mice homozygous for the Hb9$^{nlslacZ}$ allele, the number and position of lacZ cells was similar to that in heterozygotes, but no expression of endogenous HB9 was detected with either N- or C-terminally directed antisera (FIGS. 15G, H; data not shown). Similar results were found in homozygous Hb9$^{taulacZ}$ and Hb9$^{taumyc}$ mutants (data not shown). These results indicate that the targeted Hb9 alleles represent null mutations and also that the integration of lacZ into the Hb9 locus does not perturb the pattern of gene expression. The spatial pattern of endogenous HB9 expression was also mimicked in transgenic mouse embryos that expressed -galactosidase (lacZ) under the control of a ~9 kb 5' fragment of the mouse Hb9 gene (FIG. 15A, Bi, C; data not shown; see Experimental Procedures).

The persistence of lacZ expression in Hb9$^{nlslacZ}$ mutants indicates that the maintained expression of Hb9 does not require positive autoregulation. We noted, however, that the level of lacZ expression was much greater in homozygous than in heterozygous Hb9$^{nlslacZ}$ embryos (data not shown). To test whether this increase results from a function of HB9 in the repression of its own expression we compared the level of lacZ expression in Hb9$^{taulacZ}$/Hb9$^{taumyc}$ mutant embryos with that in Hb9$^{taulacZ}$ heterozygous embryos. The level of lacZ expression was >5 fold greater in the compound mutants than in Hb9$^{taulacZ}$ heterozygotes (FIGS. 15E,F), even though both sets of embryos expressed only a single Hb9$^{lacZ}$ allele. This result indicates that HB9 represses, directly or indirectly, its own transcription.

Motor Neurons are Generated in Normal Numbers in Hb9 Mutant Mice

The transient expression of HB9 by the notochord led us to examine whether the loss of Hb9 function affects the establishment of progenitor cell domains within the ventral neural tube. At e10.5, the expression of Shh, Pax6 and Nkx2.2 in the ventral spinal cord and hindbrain of homozygous Hb9$^{nlslacZ}$ embryos was indistinguishable from that in heterozygous or wild type littermates (data not shown). Thus, Shh signaling and the establishment of appropriate ventral progenitor cell domains appear to be unaffected in Hb9 mutants.

We next examined whether the initial generation of postmitotic MNs is affected by the loss of Hb9 function. LacZ expression was detected in the nuclei of cells in the ventral spinal cord in homozygous Hb9$^{nlslacZ}$ embryos at a position and number identical to that in heterozygotes (FIGS. 15G, H, 16A). The expression of lacZ persisted in MNs throughout embryonic development in both heterozygous and homozygous Hb9$^{nlslacZ}$ mutant embryos (FIGS. 16E, F; data not shown). Thus, cells in Hb9 mutant embryos retain a MN identity, as assessed by the transcription of Hb9 itself. In addition, the total number of Isl1 MNs generated between e9.5 and e10.5 was similar in heterozygous and homozygous Hb9$^{nlslacZ}$ embryos (FIGS. 17E, F, G; data not shown). Moreover, the expression of Choline Acetyltransferase (ChAT) by MNs persisted in homozygous Hb9$^{nlslacZ}$ embryos (see FIG. 19B, C; data not shown). Together, these results indicate that H29 is not required for the initial specification of MN identity.

Defects in Motor Neuron Migration in Hb9 Mutant Embryos

To determine whether aspects of the differentiation of post-mitotic MNs are affected by the loss of Hb9 function we first examined whether the overall spatial organization of MNs within the spinal cord and caudal hindbrain was affected. A marked defect in the pattern of MN migration was detected in Hb9 mutants. In wild type and heterozygous Hb9$^{nlslacZ}$ embryos examined at e10–e11, all MN cell bodies are confined to the spinal cord (FIGS. 15D, F, G; data not shown). In contrast, in homozygous Hb9$^{nlslacZ}$ embryos, ~5% of lacZ neurons were detected outside the spinal cord, within the ventral roots (FIG. 16B). These extraspinal lacZ neurons, like their counterparts within the spinal cord, coexpressed Isl1 and Isl2 (FIG. 16C; data not shown). HB9 is one of the few transcription factors that distinguishes MNs from dorsal root ganglion (DRG) neurons, raising the possibility that the detection of extraspinal lacZ neurons in Hb9 mutants was a result of their conversion to a DRG neuron identity. However, ectopic lacZ neurons did not express the sensory neuron-specific POU domain protein Brn3.0 (FIG. 16D), arguing against their sensory neuron character. These findings reveal a role for HB9 in confining the cell bodies of MNs to the spinal cord.

The settling pattern of the MNs that remained within the spinal cord and caudal hindbrain was also disrupted in Hb9$^{nlslacZ}$ mutants. At caudal hindbrain levels in heterozygous Hb9 embryos, somatic hypoglossal MNs form a well-delineated nucleus (FIG. 16E). Similarly, at cervical and lumbar levels of the spinal cord a clear separation of median motor column (MMC) MNs and lateral motor column (LMC) MNs is normally evident (FIGS. 16G, I). In contrast, in homozygous Hb9$^{nlslacZ}$ mutants there was a marked dispersion of MNs in the region of the hypoglossal motor nucleus (FIG. 16F) and no clear separation of MMC and LMC neurons was evident at cervical and lumbar levels (FIGS. 16H, J). These results suggest that the migratory and settling patterns of MNs that underlie the formation of discrete somatic motor nuclei at cranial levels, and of the major somatic motor columns at spinal levels are disrupted in Hb9 mutants.

Persistent Expression of Lim3 and Gsh4 by MNs in Hb9 Mutants

In wild type embryos, the expression of the LIM-HD proteins Lim3 and Gsh4 is rapidly lost from most post-mitotic MNs (Tsuchida et al, 1994; Ericson et al., 1997; Sharma et al., 1998). To begin to address whether there are changes in the identity of MNs in Hb9 mutant mice, we examined the profile of expression of Lim3 and Gsh4.

At e10.5 the total number of Lim3 cells was increased ~2 fold in homozygous Hb9$^{nlslacZ}$ embryos compared to heterozygous embryos (FIGS. 17A–F). Over 98% of lacZ cells in homozygous Hb9$^{nlslacZ}$ embryos coexpressed Lim3, compared to 23% in heterozygous embryos (FIGS. 17A, B, D), indicating that the increase in Lim3 neurons results from persistent expression in MNs. The persistence of Lim3 expression was widespead, occurring in post-mitotic MNs at all spinal levels and in the hypoglossal motor nucleus at caudal hindbrain levels (data not shown). In contrast, the number and position of Lim3 progenitor cells (defined as medial Lim3$^+$, lacZ$^-$, Isl1$^-$ cells) was unaffected (FIGS. 17A, B; data not shown). The expression of Gsh4 by MNs was maintained in a manner similar to that of Lim3 (data not shown). These results reveal that HB9 is required for the rapid extinction of Lim3 and Gsh4 expression from most somatic MNs, soon after their exit from the cell cycle. However, the deregulated expression of Lim3 and Gsh4 by MNs in Hb9 mutant-embryos was not sustained. By e12.5 to e13.5, the number of Lim3 cells in homozygous Hb9$^{nlslacZ}$ embryos was only 10–15% greater than in heterozygous embryos (FIGS. 17C, H), and there was a corresponding decrease in the number of cells that coexpressed Lim3 and lacZ (FIG. 17D). Thus, factors other than HB9 are eventually sufficient to extinguish Lim3 and Gsh4 expression from most somatic MNs.

Motor Neurons Transiently Acquire V2 Interneuron Character in the Absence of Hb9 Function What is the consequence of the persistent expression of Lim3 and Gsh4 by MNs? In wild type embryos, Lim3 progenitors give rise to both MNs and V2 interneurons (Ericson et al., 1997a), but V2 neurons can be distinguished by expression of the homeodomain protein Chx10 (Liu et al., 1994; Ericson et al., 1997a). Since Lim3 is sufficient to induce ectopic Chx10 expression in spinal interneurons (Tanabe et al., 1998), we reasoned that the persistence of Lim3 expression in homozygous Hb9$^{nlslacZ}$ embryos might lead MNs to acquire properties characteristic of V2 interneurons. To test this, we examined the expression of Chx10 in homozygous Hb9$^{nlslacZ}$ embryos.

The total number of Chx10 neurons was increased 2–3 fold in homozygous Hb9$^{nlslacZ}$ embryos examined over the period e10.5 to e12.5 (FIGS. 18A–F). To determine whether the increase in Chx10 neurons reflects expression in MNs, we examined the incidence of coexpression of Chx10 and lacZ. No coexpression of Chx10 and lacZ was detected in heterozygous Hb9$^{nlslacZ}$ embryos, whereas in homozygous Hb9$^{nlslacZ}$ embryos 50% of lacZ cells coexpressed Chx10 (FIGS. 18B, C) and many of these cells also expressed Isl1 (FIGS. 18E, F). In homozygous Hb9$^{nlslacZ}$ embryos, MNs did not express En1, a marker of V1 neurons that derive from progenitors that do not express Lim3 (data not shown; Ericson et al., 1997a). Thus, the acquisition of interneuron properties by MNs appears specific to markers of V2 neuron identity. Since Lim3 and Gsh4 expression are eventually extinguished from somatic MNs in Hb9$^{nlslacZ}$ mutants, we examined whether the ectopic expression of Chx10 was also transient. Ectopic Chx10 expression was lost from MNs over the period e10.5 to e13.5, whereas expression in V2 neurons persisted (FIG. 18C, F; data not shown). Thus in the absence of Hb9 function, MNs maintain expression of Lim3 and Gsh4, albeit transiently, and apparently as a consequence, acquire expression of the V2 neuron marker Chx10.

The expression of Chx10 by MNs in Hb9 mutants raised the issue of whether these neurons still project axons in a MN-like trajectory or acquire the projection pattern of V2 neurons, a class of ipsilateral spinal projection interneurons (Sharma, Jessell and Pfaff, unpublished data). We therefore examined whether Chx10$^+$, lacZ$^+$, Isl1$^+$ neurons projected axons into the periphery in Hb9$^{nlslacZ}$ mutants. After injection of HRP into the proximal region of the developing limb in e11.5 homozygous Hb9$^{nlslacZ}$ embryos, many Chx+10, Isl1/2+ neurons were labeled (FIGS. 18H, J). In contrast, in heterozygous Hb9$^{nlslacZ}$ mutants, labeled Isl1/2+, lacZ+ MNs did not express Chx10 (FIGS. 18G, I). These results show that in Hb9 mutants, many neurons that express the V2 neuron marker Chx10 continue to project axons out of the ventral root and thus retain an axonal projection characteristic of MNs.

These findings do not exclude, however, that a fraction of the Chx10 MNs in homozygous Hb9$^{nlslacZ}$ embryos acquired an axonal trajectory characteristic of V2 neurons. To test this we analyzed parasagittal sections through the ventrolateral funiculus of the spinal cord of e12.5 heterozygous and homozygous Hb9$^{nlslacZ}$ embryos. We used the Hb9$^{nlslacZ}$ allele for this analysis since the intensity of labeling and discrimination of intraspinal axons was greater than with the Hb9$^{nlslacZ}$ allele (data not shown). In both heterozygous and homozygous Hb9$^{nlslacZ}$ embryos, myc-labeled axons were detected in the ventral roots (FIGS. 18K, L), but myc-labeled intersegmental axons in the ventral funiculus were not detected (FIGS. 18M, N; data not shown). Thus, the ectopic expression of Chx10 by MNs appears not to be sufficient to reroute axons along an intraspinal trajectory.

The Emergence of MN Subtype Identity is Disrupted in Hb9 Mutants

The early alteration in migratory behavior and in the profile of transcription factor expression by MNs in Hb9 mutants prompted us to examine whether the later molecular programs that define aspects of MN identity are affected. We first examined whether the profile of expression of Isl1, a LIM-HD protein that is initially expressed by all postmitotic MNs, is altered at later stages in Hb9 mutants.

Although the initial number of Isl1 MNs was not altered by the loss of HB9 function (FIG. 17G), from e10.5 onwards there was a progressive decline in the number of Isl1 neurons. By e13.5 the number of Isl1 neurons detected in homozygous Hb9$^{nlslacZ}$ embryos was only ~30% that in heterozygous or wild type embryos (FIG. 17G). The loss of Isl1 expression was not the consequence of the death of MNs since no increase in TUNEL-labeled cells was detected in the ventral spinal cord over this period (data not shown), and the total number of lacZ cells was not reduced. Thus, despite the initial generation of MNs in normal numbers in homozygous Hb9$^{nlslacZ}$ embryos, a marked disruption in the dynamic profile of expression of several LIM-HD proteins soon becomes evident.

By e12.5–e13.5, MNs have acquired distinct class, columnar and pool identities that can be defined by the expression of specific molecular markers (FIG. 19A). We therefore examined whether the expression of MN subtype markers is affected by the loss of HB9 function.

MN Class Identity: The segregation of spinal MNs into somatic and visceral classes was maintained in Hb9 mutant embryos. Somatic MNs can be identified at e12.5 by expression of Isl2 (Tsuchida et al., 1994) and at this stage the number of Isl2 neurons was similar in homozygous and heterozygous Hb9$^{nlslacZ}$ mutants (FIGS. 19D, E; data not shown). Thus, somatic MN differentiation occurs in the absence of HB9 function.

In the spinal cord, visceral MNs are generated predominantly at thoracic levels and can be defined by their location within the intermediate region (Barber et al., 1991; Markham and Vaughn, 1991), and molecularly, by their expression of -nicotinamide adenine dinucleotide phosphate diaphorase (NADPH-d) activity (Wetts et al., 1995). The number of neurons in the intermediate spinal cord that expressed NADPH-d neurons was markedly reduced in Hb9$^{nlslacZ}$ mutants examined at e14 to e17 (FIGS. 19F, G; data not shown). The loss of NADPH-d expression, however, was much more marked in medially located neurons and many laterally located NADPH-d MNs were still detected (FIGS. 19F, G; data not shown). The extent of ChAT expression by MNs in medial regions of the intermediate spinal cord was also significantly reduced in Hb9$^{nlslacZ}$ mutants (FIGS. 19B, C; data not shown). LacZ neurons were, however, detected at approximately normal numbers within both the medial and lateral regions of the intermediate spinal cord in homozygous Hb9$^{nlslacZ}$ embryos (data not shown), suggesting that the differentiation rather than the generation of visceral MNs is affected by the loss of Hb9 function. The generation and differentiation of visceral MNs at caudal hindbrain and cervical spinal cord levels was not affected in Hb9 mutant embryos, consistent with the finding that cranial visceral MNs do not express HB9 (Briscoe et al., 1999).

MN Columnar Identity: We next examined the expression of molecular markers that define the columnar subtype identity of MNs. By e12.5–13.5, Lim3 MNs are normally restricted to the medial MMC (FIG. 19H) but in homozygous Hb9$^{nlslacZ}$ embryos, Lim3 MNs were more widely dispersed throughout the LMC domain (FIG. 19I). Although this result could simply reflect the persistence of expression of Lim3 by many MNs, it provides evidence that neurons with a molecular profile characteristic of the medial MMC are displaced in Hb9 mutants.

The differentiation of MNs within the LMC was also disturbed in Hb9 mutants. At limb levels of the spinal cord, the expression of Retinaldehyde dehydrogenase 2 (RALDH2), a generic marker of LMC neurons (Zhao et al., 1996; Sockanathan and Jessell, 1998), was markedly reduced in homozygous Hb9$^{nlslacZ}$ embryos (FIGS. 19J, K). Moreover, the differentiation of MNs within the lateral subdivision of the LMC, characterized by coexpression of Isl2 and Lim1 was also greatly reduced (FIGS. 19L, M). Nevertheless, some lateral LMC MNs were detected, suggesting that the columnar subdivision of the LMC is not completely abolished in Hb9 mutants.

MN Pool Identity: Within the LMC, distinct motor pools can be distinguished by expression of the ETS proteins PEA3 and ER81 (Lin et al., 1998; Arber, Lin, Shneider and Jessell, unpublished data). A marked reduction in the expression of PEA3 and ER81 was detected in LMC MNs, both at forelimb and hindlimb levels. At forelimb levels, for example, a medial LMC-derived motor pool that innervates the pectoralis muscle expresses PEA3 (FIG. 19N). In homozygous Hb9$^{nlslacZ}$ embryos, PEA3 expression was almost completely absent from MNs at this axial level (FIG. 19O). The disruption in expression of ETS protein expression was generally more severe than the loss of columnar markers (data not shown). ER81 and PEA3 expression by subsets of dorsal root ganglion neurons was, however, not affected in homozygous Hb9$^{nlslacZ}$ embryos (FIG. 19N, O, data not shown). Taken together, these results reveal that the elimination of HB9 function results, directly or indirectly, in a disruption in the establishment of the class, columnar and pool identities of MNs Defects in Motor Axon Trajectories in Hb9 Mutant Mice What are the consequences of the marked disruption in the molecular program of MN differentiation for the connectivity of MNs? To begin to address this issue, we examined whether the projection of motor axons towards their peripheral targets is altered in Hb9 mutant embryos.

In heterozygous Hb9$^{taulacZ}$ embryos examined at e11.5, the pattern of axonally transported lacZ expression coincided with the trajectories of somatic MNs (FIG. 20A; data not shown; see Ericson et al., 1997a). For example at hindbrain levels, the hypoglossal nerve, and at cervical spinal cord levels the segmentally-arrayed projections of somatic motor axons in the ventral roots, were delineated by lacZ expression (FIG. 20A). LacZ-labelled peripheral motor axons were also detected in homozygous Hb9$^{taulacZ}$ embryos (FIGS. 20B–D; data not shown), indicating that HB9 is not required for the initial projection of motor axons into the periphery. However, there were marked, albeit variable, defects in the more distal projections of motor axons in homozygous Hb9$^{taulacZ}$ embryos (FIGS. 20B–D; data not shown). One of the most dramatic instances of the variability of the defects in motor axon trajectory was detected at caudal hindbrain levels. The hypoglossal motor nerve was either absent completely or severely misrouted in some Hb9 mutant embryos (FIG. 20B; data not shown), but present with an apparently normal trajectory in others (FIG. 20C).

The disruption in motor axon trajectories in Hb9 mutants led us to examine whether the major branches of somatic motor axons to axial and limb regions were formed. Analysis of the pattern of motor nerve branching both in embryos stained in whole-mount and in transverse sections revealed a marked defect in the organization of motor nerves at the axial muscle branch point and at the plexus region at the base of the fore- and hind-limbs. In heterozygous Hb9$^{taulacZ}$ and Hb9$^{taumyc}$ embryos, motor axons at these plexus regions formed a tight fascicle (FIGS. 20A, E, F), whereas in homozygous embryos motor axons were dispersed and defasciculated (FIGS. 20B, C, G, H; data not shown). Nevertheless, motor axon projections to axial muscles were detectable in homozygous Hb9$^{taulacZ}$ and Hb9$^{taumyc}$ embryos (FIGS. 20E–H; data not shown). Similarly, distinct motor axon branches projected into the dorsal and ventral halves of the limb mesenchyme in Hb9 mutant embryos (FIGS. 20D, G). Thus, there are marked defects in the peripheral organization of motor nerves at sites of critical motor axon pathfinding decisions, although the major peripheral axon branches of somatic MNs are present.

Defects in Muscle Innervation by Motor Axons in Hb9 Mutants

The defect in the peripheral organization of motor nerve branches in Hb9 mutants led us to examine whether there are also defects in the innervation of target muscles. We first analysed the innervation of limb muscles in late embryonic stage (e17.5) embryos, using GAP-43 expression to visualize peripheral axons and -bungarotoxin labeling to delineate clusters of acetylcholine receptors (AChR) on the muscle surface. We detected no obvious defect in the pattern of motor innervation or in AChR expression in fore- and hind-limb muscles in Hb9 mutant embryos (data not shown).

Hb9 mutant mice die soon after birth with uninflated lungs, and we therefore considered the possibility that the innervation of the diaphragm muscle by phrenic MNs might be affected. In the diaphragm of wild type and heterozygous Hb9$^{nlslacZ}$ neonates, AChR clusters were restricted to a central domain of the muscle that coincided with the position of muscle innervation (FIG. 20I). In contrast, in homozygous Hb9$^{nlslacZ}$ mice, AChR clusters were present but distributed over a much wider region of the muscle surface (FIG. 20J). Many of these scattered AChR clusters were abnormally small (FIG. 20J; data not shown), and the thickness of the diaphragm muscle was markedly reduced in homozygous Hb9$^{nlslacZ}$ embryos (FIGS. 20K, L). In addition, in the diaphragm of wild type and heterozygous Hb9$^{nlslacZ}$ mice, AChR clusters were invariably associated with GAP43-labeled nerve terminals (FIG. 20K). In contrast, in homozygous Hb9$^{nlslacZ}$ mice, many AChR clusters were not associated with GAP43-labeled nerve branches (FIG. 20L). Extensive axonal sprouting was also detected in regions of the diaphragm close to the point of entry of the phrenic nerve (data not shown). These observations reveal a marked defect in the innervation of certain skeletal muscles in Hb9 mutant embryos. They also raise the possibility that the perinatal lethality of Hb9 mutant animals results, at least in part, from the diaphragm denervation phenotype.

Discussion

This paper provides evidence that many aspects of the differentiation of post-mitotic MNs in the mammalian spinal cord depend on functions provided by the homeobox gene Hb9. Our findings add to an understanding of the molecular steps of MN differentiation in two main ways. They provide genetic evidence that the signals involved in the generation of MNs can be dissociated from the later steps that consolidate MN identity. In addition, they provide evidence that a transcription factor expressed at an early stage in the differentiation of all spinal MNs has an essential function in the acquisition of MN subtype identities. Thus, they provide an initial insight into the hierarchical relationship of the transcription factors that define distinct functional subsets of MNs in the developing spinal cord. We discuss the possible roles of HB9 in the progressive specification of MN identity that are suggested by this analysis of the Hb9 mutant phenotype.

A Requirement for HB9 Function in Early Motor Neuron Development

At the earliest stages of MN genesis, late-stage Lim3$^+$ MN progenitors express HB9. However, during the peak period of MN generation the onset of HB9 expression by most cells appears to occur after that of Lim3 and coincident with Isl1, apparently in newly generated post-mitotic MNs. Consistent with this, the loss of Hb9 function has no discernable effect on the number of spinal MNs initially generated. Thus, the phenotype of Hb9 mutant mice supports the idea that the relevant period of expression and function of HB9 is in post-mitotic MNs. Previous studies have analyzed MN differentiation in mice lacking Isl1, a LIM homeodomain protein expressed almost exclusively by post-mitotic MNs. However, in Isl1 mutant mice, MNs undergo rapid apoptotic death, (Pfaff et al., 1996; Ericson, Kania and Jessell, unpublished data), hindering an analysis of later steps in MN differentiation. Isl1 is initially expressed by MNs in Hb9 mutant mice but many neurons rapidly lose Isl1 expression. Despite this, MNs survive. This result, taken together with the more drastic MN phenotype of Isl1 mutant mice, suggests that MNs may require Isl1 for their survival only during a brief critical period, soon after cell cycle exit.

A Role for HB9 in the Consolidation of the Motor Neuron-V2 Interneuron Identity Decision The progenitors of both MNs and V2 interneurons are marked by expression of Lim3 (and the functionally redundant protein Gsh4), implying that additional factors are required to select between these two neuronal fates. The analysis of changes in transcription factor expression by post-mitotic MNs in Hb9 mutant embryos provides support for the idea that emerged from studies in chick (Tanabe et al., 1998) that the MNR2/HB9 class of homeodomain proteins has a role in selecting MN rather than V2 interneuron identity within the ventral spinal cord. In the chick, ectopic expression of MNR2 and HB9 suppresses the generation of V2 interneurons and promotes MN differentiation, providing gain-of-function evidence that MNR2 and HB9 have such a neuronal subtype selector function. The present studies provide complementary loss-of-function evidence that HB9 serves such a function in MNs, acting to repress the expression of V2 interneuron character and thus to consolidate MN fate (FIG. 21). These results have the additional implication that the stabilization of MN rather than V2 interneuron identity may not be achieved until after MNs have left the cell cycle.

At a molecular level, the HB9-dependent consolidation of MN phenotype is likely to be mediated through the regulation of Lim3 (and Gsh4) (FIG. 21). In Hb9 mutant embryos, the expression of Lim3 and Gsh4 persists in post-mitotic MNs for an abnormally long period, implying that HB9 normally functions, directly or indirectly, to repress the expression of Lim3 and Gsh4. In the chick, ectopic expression of Lim3 is sufficient to induce V2 interneuron markers in a cellular context in which MNR2 and other MN homeodomain proteins are not expressed (Tanabe et al., 1998). It is likely, therefore, that the persistence of Lim3 and Gsh4 expression in Hb9 mutants is responsible for the ectopic expression of Chx10 by MNs (FIG. 21). Nevertheless, MNs do not undergo a complete switch to a V2 interneuron identity in Hb9 mutants. The incomplete and transient nature of the switch to a V2 interneuron identity may reflect the prior action of progenitor cell factors that initiate the process of MN specification.

An important issue raised by our findings is that of the respective roles of HB9 in the development of mouse and chick MNs. In the chick, HB9 expression is restricted to post-mitotic MNs whereas MNR2 expression is detected at a much earlier stage, in MN progenitors (Tanabe et al., 1998). In contrast, in mouse, HB9 expression is detected in some MN progenitors at early stages of MN genesis. But over the peak period of MN generation, our data provide evidence that the expression of HB9 is delayed with respect to that of Lim3 and appears coincident with that of Isl1. Thus, HB9 appears to be expressed at a slightly earlier stage in the progression of MN differentiation in mouse than is its counterpart in chick. Nevertheless, the profile of expression of mouse HB9 does not include an early and prominent phase of expression in MN progenitors, a profile characteristic of chick MNR2. A mouse MNR2 homolog has not been isolated to date, however (C. William and Y. Tanabe; personal communication). Thus, we cannot exclude that in mouse, HB9 has subsumed the functions performed in chick by MNR2. If this is the case, the finding that MNs are generated in normal numbers in Hb9 mutants would argue for the existence of a MNR2/HB9-independent pathway of MN generation. As discussed previously (Tanabe et al., 1998), such a pathway must operate at least in the hindbrain since neither mouse nor chick cranial visceral MNs, nor their progenitors, express MNR2 or HB9 (Tanabe et al., 1998; Briscoe et al., 1999). The ability of MNR2 and HB9 to induce a coordinate program of MN differentiation in chick spinal cord, together with the MN phenotype detected in Hb9 mutant mice does, however, support the idea that this homeodomain protein subfamily has an important, if as yet incompletely defined, role in early MN differentiation.

The Acquisition of Motor Neuron Subtype Identities is Impaired in Hb9 Mutant Mice The early post-mitotic period of MN development is accompanied by the differentiation of functional subsets of MNs that can be defined both in terms of their anatomical organization and by expression of specific molecular markers (see FIG. 19A). Many aspects of the differentiation of distinct MN subtypes, including columnar divisional and pool identities, are markedly affected by the loss of Hb9 function (FIG. 21).

These defects in MN subtype identity could simply be an indirect consequence of the persistence of expression of Lim3 and Gsh4 and/or the ectopic expression of Chx10. Nevertheless, defects in the columnar and pool identities of MNs are evident well after the phase of deregulation of Lim3, Gsh4 and Chx10 expression has subsided. Thus, it remains possible that HB9 has a more direct role in the specification of MN subtype identity. HB9 could, for example, function as a cofactor in a series of independent molecular programs that regulate the emergence of columnar, divisional and pool subtype identities. Alternatively, HB9 could act at an early point in an obligate sequential program of somatic MN differentiation that progresses from columnar to divisional to pool identity. One line of evidence that argues against a strict requirement for sequential programs of MN subtype differentiation derives from the observation that retinoids appear able to impose a lateral LMC character on thoracic level MNs that have not acquired a generic LMC character, (Sockanathan and Jessell, 1998). Thus, MN divisional character, at least, may be acquired independently of columnar character.

The proposed roles of the MNR2/HB9 proteins in regulating of MN subtype identity may have some parallels with the functions of the Phox2a/b homeodomain proteins in the specification of sympathetic neuronal fate (Goridis and Brunet, 1999; Lo et al., 1999; Pattyn et al., 1999). Phox2 proteins are necessary for the induction of transmitter synthetic enzymes and other features of sympathetic neuronal differentiation. In addition, at hindbrain levels, the Phox2 proteins are expressed selectively by visceral MNs, in a pattern complementary to that of MNR2 and HB9 (Goridis and Brunet, 1999; Briscoe et al., 1999). It is possible, therefore, that the segregated expression of these two families of homeodomain proteins contributes to distinctions in somatic and visceral subtype identity of cranial MNS.

Perturbed Motor Neuron Migration and Axonal Projections in Hb9 Mutants

The loss of Hb9 function results in marked defects in the migratory and settling patterns of spinal MNs. The most striking migratory defect in Hb9 mutants is the failure of many MN cell bodies to be retained within the spinal cord. These defects in MN migration are accompanied by marked errors in the pattern of axonal projections of somatic MNs. There is, however, variability in the precise nature of the errors in motor axon projection between mutant embryos. One consistent axoral projection phenotype in the spinal cord of Hb9 mutant mice is a pronounced defasciculation of axons, evident at the branch point of axial and limb-directed motor axons, and also at the plexus region at the base of the limbs. This finding raises the possibility that adhesive interactions between motor axons and/or the ability of motor axons to respond to extrinsic guidance cues are impaired in Hb9 mutants.

Despite these defects, each of the major axonal branches of spinal somatic MNs, to axial muscles and to dorsal and ventral limb muscles, is present in Hb9 mutant embryos. The detection of overtly normal projections to axial muscles is not surprising since these axons originate from medial MMC neurons that normally retain expression of Lim3 and Gsh4 (Tsuchida et al., 1994; Ericson et al., 1997; Sharma et al., 1998). The detection in Hb9 mutant embryos of both dorsally and ventrally directed motor axon branches in the limb may reflect, in part, the residual differentiation of some lateral LMC neurons. Nevertheless, the axons of many MNs that have lost their LMC identities also appear able to make either dorsal or ventral projections into the limb bud. This finding is consistent with previous studies showing that thoracic level MNs that are committed to a MMC identity form dorsal and ventral axonal projections in the limb when transplanted to limb levels (O'Brien et al., 1990; O'Brien and Oppenheim, 1990; Ensini et al., 1998). It seems possible, therefore, that the acquisition of LMC divisional identity provides MNs with the ability to select appropriately a dorsal or ventral trajectory, rather than embarking along one or other trajectory at random. The necessity for motor axons to project along either a dorsal or ventral path in the limb may reflect the presence of a non-permissive environment for axons in the central core of the developing limb mesenchyme (see Tosney and Landmesser, 1985).

Taken together, our studies provide evidence that HB9 has an essential role in consolidating the identity of spinal MNs and in particular in suppressing the expression of V2 interneuron character. Since HB9 expression persists in adult MNs it is possible that its activities help to maintain the differentiated properties of MNs into post-natal and adult life. Defining the direct downstream targets of HB9 may help to clarify further how the molecular and functional properties of MN subtypes are established.

Experimental Procedures

Generation of Hb9 Mutant and Transgenic Mice

Mouse genomic clones used in the generation of Hb9 mutant mice and transgenic lines were derived from a 129/Sv genomic library (Stratagene). The transgenic TgN (Hb9)SAX16 line was derived from a construct that used a 9kb NotI fragment comprising the 5' upstream region of the Hb9 gene inserted 5' to an IRES-nls-lacZ cassette (see below). The targeting vector for the production of Hb9 mutant mice was constructed from genomic fragments derived from a 9 kB NotI fragment 5' to the first exon of Hb9 and a HindIII clone overlapping with the 5' clone, but extending into the 3' region of Hb9. A 6 kB 5' Sse8387:1-NotI fragment spanning into the first exon of Hb9 and an adjacent 3 kB 3' NotI-XbaI fragment were cloned into a vector containing a PmeI site for linearization of the targeting constructs. NotI or PacI flanked targeting cassettes were generated independently (and comprised IRES-nls-lacZ, IRES-tau-lacZ, IRES-tau-myc, a SV40 polyadenylation signal and a lox flanked PGK-NEO cassette). These cassettes were integrated into the basic targeting construct. For the generation of expression cassettes, marker genes were inserted downstream of an internal ribosome entry site (IRES) from encephalomyocarditis virus (Ghattas et al., 1991), in frame with the ATG of a NcoI site at the 3' end of the IRES (Mombaerts et al., 1996). Linearized targeting constructs were electroporated into W95 ES-cells, selected with G418 and screened for potential recombinants by Southern blot analysis. A 1 kB 3' XbaI-XhoI fragment was used as a probe to screen for ES-cell recombinants (SalI/XhoI digest). This probe generates a 20 kB wild-type band and a 6 kB mutant band. The average frequency of recombination for the four constructs described in this study was ~1:20. Recombinant clones were injected into C57BL/6J blastocysts to generate chimeric founders that transmitted the mutant allele. All experiments presented in this study involved analysis of embryos derived from heterozygous 129Sv×C57BL/6J intercrosses.

A 5' Fragment of the Hb9 Gene Confers Motor Neuron-Specific Transgene Expression.

A ~9kb NotI fragment of Hb9 (FIGS. 15A, Bi) was sufficient to direct et SV40-nlslacZ fusion protein to developing MNs in transgenic mouse embryos, examined at e10 (FIG. 15C; data not shown). The pattern of lacZ corresponded closely to the expression of endogenous HB9 (FIGS. 14; 15C and data not shown). The restriction of transgene expression to somatic MNs was apparent at this stage at caudal hindbrain levels where lacZ, like HB9 was expressed by somatic hypoglossal MNs but was excluded from visceral vagal MNs (Briscoe et al., 1999; data not shown). At sacral levels of e9.5–e10.5 embryos both endogenous HB9 expression and lacZ expression in transgenic mice was detected throughout the neural tube, in the notochord and also in the primitive gut tube (data not shown).

In Situ Hybridization, Histochemistry and Immunocytochemistry

For in situ hybridization analysis, sections were hybridized with mouse RALDH2 and ChAT specific digoxigenin-labeled probes (Schaeren-Wiemers and Gerfin-Moser, 1993). Antibodies used in this study were: monoclonal IgG anti-Hb9 (N-terminal), rabbit anti-HB9 (C-terminal; kindly provided by S. Pfaff), Pax6, MPM2, NF160, BrdU-FITC (Tanabe et al., 1998; Ericson et al., 1997), skeletal -actinin (Sigma), anti-Lim1/2 (Tsuchida et al., 1994); rabbit anti-Lim3, Isl1/2, Isl2, Hb9 (N-terminal), Nkx2.2, Chx10, Brn3.0 (Tanabe et. al., 1998; Ericson et al., 1997), GAP-43 (Aigner et al., 1995), PEA3 (Arber et al., unpublished, generated against the 14 C-terminal a.a. of mouse PEA3 coupled to KLH, used at 1:1000), myc (S. Morton and T. M. Jessell, unpublished, generated against the myc epitope (Evan et al., 1985) coupled to KLH, used at 1:8000), -Galactosidase (Cappel); goat anti- -Galactosidase (Arnel) HRP (Jackson labs); guinea pig anti-Isl1 (Tanabe et al., 1998). Cryostat sections were processed for immunohistochemistry as described (Tsuchida et al., 1994) using fluorophore-conjugated secondary antibodies (Jackson Labs) (1:500 to 1:1000). Rhodamine labeled -bungarotoxin (Jackson Labs) was used at 1:2000. Images were collected on a BioRad MRC 1024 confocal microscope.

BrdU Labeling and Histology

BrdU experiments were performed by intraperitoneal injection of BrdU (Sigma, 50 g/g body weight) 2 h before sacrifice. Detection of BrdU was performed as previously described (Sockanathan et al., 1998). TUNEL assays were performed using a kit from Boehringer, NADPH-diaphorase reactions were performed as described (Wetts et al., 1995), -Galactosidase whole-mount staining was performed as described (Mombaerts et al., 1996).

Retrograde Neuronal Labeling

20% HRP (Boehringer), 1% Isolecithin (ICN) in PBS was injected into the limb of e11.5 mouse embryos or into the ventral funiculus of e13.5 spinal cord and incubated for 2–4 h as described (Landmesser, 1978b) before fixation and immunocytochemical detection of HRP.

References

Aigner, L., Arber, S., Kapfhammer, J. P., Laux, T., Schneider, C., Botteri, F., Brenner, H. R., Caroni, P. (1995). Overexpression of the neural growth-associated protein GAP-43 induces nerve sprouting in the adult nervous system of transgenic mice. Cell 83, 269–278.

Appel, B., (1999). LIMitless combinations? Neuron 22, 3–5.

Bang, A. G. and Goulding, M. D. (1996). Regulation of vertebrate neural cell fate by transcription factors. Curr. Opin. Neurobiol. 6, 25–32.

Barber, R. P., Phelps, P. E. and Vaughn, J. E. (1991). Generation patterns of immunocytochemically identified cholinergic neurons at autonomic levels of the rat spinal cord. J. Comp. Neurol. 311, 509–519.

Briscoe, J., Sussel, L., Serup, P., Hartigan-O'Connor, D., Jessell, T. M., J. L. R. Rubenstein and Ericson, J. (1999). Role of homeobox gene Nkx2.2 in the specification of neuronal identity by graded hedgehog signaling. Nature 398, 622–627.

Cepko, C. L. (1999). The roles of intrinsic and extrinsic cues and bHLH genes in the determination of retinal cell fates. Curr. Opin. Neurobiol. 9, 37–46.

Edlund, T. and Jessell, T. M. (1999). Progression from extrinsic to intrinsic signaling in cell fate specification: a view from the nervous system. Cell 96, 211–224.

Ensini, M., Tsuchida, T. N., Belting H. G., and Jessell, T. M. (1998). The control of rostrocaudal pattern in the developing spinal cord: specification of motor neuron subtype identity is initiated by signals from paraxial mesoderm. Development 125, 969–982.

Ericson, J., Thor, S., Edlund, T., Jessell, T. M., and Yamada, T. (1992). Early stages of motor neuron differentiation revealed by expression of homeobox gene Isl1. Science 256, 1555–60.

Ericson, J., Morton, S., Kawakami, A., Roelink, H., and Jessell, T. M. (1996). Two critical periods of sonic hedgehog signaling required for the specification of motor neuron identity. Cell 87, 661–673.

Ericson, J., Rashbass, P., Schedl, A., Brenner-Morton, S., Kawakami, A., van Heyningen, V., Jessell, T. M., and Briscoe, J. (1997a). Pax6 controls progenitor cell identity and neuronal fate in response to graded Shh signaling. Cell 90, 169–180.

Ericson, J., Briscoe, J., Rashbass, P, van Heyningen, V., and Jessell, T. M. (1997b). Graded Sonic Hedgehog signaling and the specification of cell fate in the ventral neural tube. C. S. H. Symp. Quant. Biol. 62, 451–466.

Evan, G. I., Lewis, G. K., Ramsay, G., Bishop, J. M. (1985). Isolation of monoclonal antibodies specific for human c-myc proto-oncogene product. Mol. Cell Biol. 5, 3610–3616.

Ghattas, I. R., Sanes J. R. and Majors, J. E. (1991). The encephalomyocarditis virus internal ribosome entry site allows efficient coexpression of two genes from a recombinant provirus in cultured cells and in embryos. Mol. Cell Biol. 11, 5848–5859.

Goridis, C. and Brunet, J. F. (1999). Transcriptional control of neurotransmitter phenotype. Current opinion in Neurobiology. 9, 47–53.

Goulding, M. (1998). Specifying motor neurons and their connections. Neuron 21, 943–946.

Harrison, K. A., Druey, K. M., Deguchi, Y., Tuscano, J. M., and Kehrl, J. H. (1994). A novel human homeobox gene distantly related to proboscipedia is expressed in lymphoid and pancreatic tissues. J. Biol. Chem. 269, 19968–19975.

Landmesser, L. (1978a). The distribution of motorneurons supplying chick hind limb muscles. J. Physiol. 284, 371–389.

Landmesser, L. (1978b). The development of motor projection patterns in the chick hind limb. J. Physiol. 284, 391–414.

Lance-Jones, C. and Landmesser, L. (1981). Pathway selection by embryonic chick motoneurons in an experimentally altered environment. Proc. R. Soc. Lond. 214, 19–52.

Lin, J. H., Saito, T., Anderson, D. J., Lance-Jones, C., Jessell, T. M., and Arber, S. (1998). Functionally related motor neuron pool and muscle sensory afferent subtypes defined by coordinate ETS gene expression. Cell 95, 393–407.

Liu, I. S., Chen, J. D. Ploder, L., Vidgen, D., van der Kooy, D., Kalnins, V. I., and McInnes, R. R. (1994). Developmental expression of a novel murine homeobox gene (Chx10): evidence for roles in determination of the neuroretina and inner nuclear layer. Neuron 13, 377–393.

Lo, L., Tiveron, M. C. and Anderson, D. J. (1998). MASH1 activates expression of the paired homeodomain transcription factor Phax2a, and couples pan-neuronal and subtype-specific components of autonomic neuronal identity. Development 125 609–620.

Lo, L., Morin, X., Brunet, J-F., and Anderson, D. J. (1999). Specification of neurotransmitter identity by Phox2 proteins in neural crest stem cells. Neuron, 22, 693–705.

Markham, J. A. and Vaughn, J. E. (1991). Migration patterns of sympathetic preganglionic neurons in embryonic rat spinal cord. J. Neurobiol. 22, 811–822.

Mombaerts, P., Wang, F., Dulac, C., Chao, S. K., Nemes, A., Mendelsohn, M., Edmondson, J., and Axel, R. (1996). Visualizing an olfactory sensory map. Cell, 87, 657–686.

Nornes, H. O. and Carry, M. (1978). Neurogenesis in spinal cord of mouse: an autoradiographic analysis. Brain Res. 159, 1–6.

O'Brien, M. K. and Oppenheim, R. W. (1990). Development and survival of thoracic motoneurons and hindlimb musculature following transplantation of the thoracic neural tube to the lumbar region in the chick embryo: anatomical aspects. J. Neurobiol. 21, 313–340.

O'Brien, M. K., Landmesser, L. and Oppenheim R. W. (1990). Development and survival of thoracic motoneurons and hindlimb musculature following transplantation of the thoracic neural tube to the lumbar region in the chick embryo: functional aspects. J. Neurobiol. 21, 341–355.

Pattyn, A., Morin, X., Cremer, H., Goridis, C., and Brunet, J. F. (1999). The homeobox gene Phox2b is essential for the development of autonomic neural crest derivatives. Nature 399, 366–370.

Pfaff, S. L., Mendelsohn, M., Stewart, C. L., Edlund, T., and Jessell, T. M. (1996). Requirement for LIM homeobox gene Isl1 in motor neuron generation reveals a motor neuron-dependent step in interneuron differentiation. Cell 84, 309–320.

Ross, A. J., Ruiz-Perez, V., Wang, Y., Hagan, D. M., Scherer, S., Lynch, S. A., Lindsay, S., Custard, E., Belloni, E., Wilson, D. I., Wadeym R., Goodman, F., Orstavik, K. H., Monclair, T., Robson, S., Reardon, W., Burn, J., Scambler, P., and Strachan, T. (1998). A homeobox gene, HLXB9, is the major locus for dominantly inherited sacral agenesis. Nat. Genet. 20, 358–361.

Saha, M. S., Miles, R. R., and Grainger, R. M. (1997). Dorsal-ventral patterning during neural induction in Xenopus: assessment of spinal cord regionalization with xHB9, a marker for the motor neuron region. Dev. Biol. 187, 209–223.

Schaeren-Wiemers, N. and Gerfin-Moser, A. (1993). A single protocol to detect transcripts of various types and expression levels in neural tissue and cultured cells: in situ hybridization using digoxigenin-labelled cRNA probes. Histochemistry 100, 431–440.

Sharma, K., Sheng, H. Z., Lettieri, K., Li, H., Karavanov, A., Potter, S., Westphal, H., and Pfaff, S. L. (1998). LIM homeodomain factors Lhx3 and Lhx4 assign subtype identities for motor neurons. Cell 95, 817–828.

Sockanathan, S. and Jessell, T. M. (1998). Motor neuron-derived retinoid signals determine the number and subtype identity of motor neurons in the developing spinal cord. Cell, 94, 503–514.

Tanabe, Y. and Jessell, T. M. (1996). Diversity and pattern in the developing spinal cord. Science 274, 1115–1123.

Tanabe, Y., William, C. and Jessell, T. M. (1998). Specification of motor neuron identity by the MNR2 homeodomain protein. Cell 95, 67–80.

Tosney, K. W. and Landmesser, L. T. (1985). Development of the major pathways for neurite outgrowth in the chick hindlimb. Dev. Biol. 109, 193–214.

Tsuchida, T., Ensini, M., Morton, S. B., Baldassare, M., Edlund, T., Jessell, T. M., and Pfaff, S. L. (1994) Topographic organization of embryonic motor neurons defined by expression of LIM homeobox genes. Cell 79, 957–970.

Wetts, R., Phelps, P. E., and Vaughn, J. E. (1995). Transient and continuous expression of NADPH diaphorase in different neuronal populations of developing rat spinal cord. Dev. Dyn. 202, 215–228.

Westendorf, J. M. Rao, P. N., and Gerace, L. (1994). Cloning of cDNAs for M-phase phosphoproteins recognized by the MPM2 monoclonal antibody and determination of the phosphorylated epitope. Proc. Natl. Acad. Sci. USA 91, 714–718.

Zhao, D., McCaffery, P., Ivins, K. J., Neve, R. L., Hogan, P., Chin, W. W. and Drager, U. C. (1996) Molecular identification of a major retinoic-acid-synthesizing enzyme, a retinaldehyde-specific dehydrogenase. Eur. J. Biochem. 240, 15–22.

Third Set of Experiments

Figures 22A, 22C, 22E:
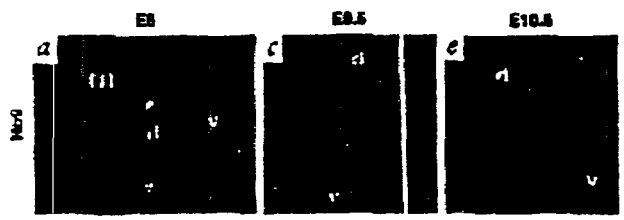
Figures 22B, 22D, 22F:
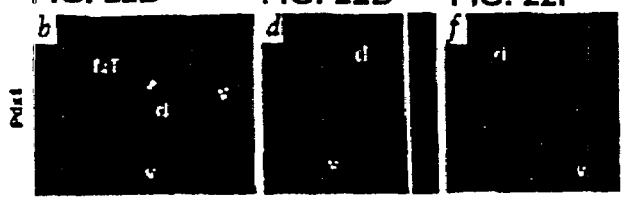
Figures 22G, 22H, 22I:
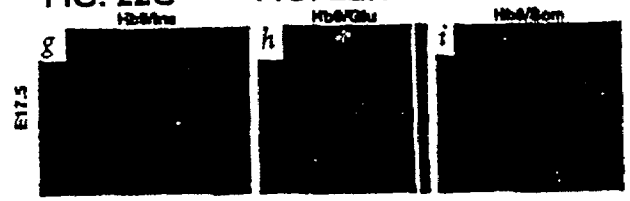

During mouse embryonic development, Hb9 expression is first evident at the approximately 8-somite stage (E8) in the notochord, in the entire dorsal gut endoderm and in the ventral endoderm at the prospective pancreatic level (FIG. 22a, and data not shown). In contrast, Pdx1 at this stage is expressed only in the ventral pancreatic endoderm (FIG. 22b). Thus, in the dorsal pancreatic anlage, the initiation of Hb9 expression appears to precede that of Pdx1, whereas in the ventral anlage both genes are expressed concurrently. By E9.5 the level of Hb9 protein is reduced in both pancreatic buds and notochord (FIG. 22c, and data not shown). At E10.5, only a low level of Hb9 expression remain in the dorsal pancreatic bud and virtually no expression is detected in the ventral bud or in the notochord (FIG. 22e, and data not shown). In contrast, Pdx1 expression is maintained in both pancreatic buds at theses stages (Ohlsson et al. 1993; Ahlgren et al. 1996) (FIG. 22d,f). Thus, cells in both the dorsal and ventral buds express Hb9 transiently at early embryonic stages. At later stages, Hb9 expression reappears in the differentiating pancreas. At E17.5, Hb9 expression was detected in the insulin-producing β-cells (FIG. 22g) but not in glucagon-producing α-cells (FIG. 22h) or somatostatin-producing δ-cells (FIG. 22i). No Hb9 expression was observed in non-endocrine pancreatic cells FIG. 22, and data shown) The β-cell-specific expression persisted in the adult pancreas (data not shown). These results show that Hb9 is expressed in two distinct developmental phases, first during the evagination of the pancreatic buds and later in differentiating β-cells.

To determine the role of Hb9 in the development of the pancreas, we analyzed mice in which Hb9 had been inactivated by homologous recombination in ES cells (Arber et al. submitted for publication). E17.5 $Hb9^{nlslacZ}$ mutant embryos exhibited an overtly normal gastrointestinal tract, although the duodenum appeared expanded (FIG. 23a). Analysis of the pancreas revealed that the dorsal pancreatic epithelial bud was absent, whereas the ventral bud was present (FIG. 23a). The spleen, an organ that develops from the dorsal mesenchyme, was present in Hb9 mutants (FIG. 23a), and analysis of B13.5 embryos showed that the mesenchyme that normally surrounds the dorsal pancreas was present and appeared to have developed normally (FIG. 23b). The lack of the dorsal pancreatic bud, therefore, appears to reflect a selective defect in the specification and development of the presumptive dorsal pancreatic epithelium.

To determine the stage at which the development of the dorsal pancreas is perturbed, we analyzed E9.5–10.5 $Hb9^{nlslacZ}$ homozygous embryos by whole-mount detection of β-galactosidase (β-gal) activity. At E9.5, β-gal activity was observed throughout the dorsal endoderm of both heterozygous and homozygous $Hb9^{nlslacZ}$ embryos (FIG. 23c,d). In homozygous $Hb9^{nlslacZ}$ the evagination of the dorsal pancreatic bud failed to occur (FIG. 23c,d). Analysis of E9.5 $Hb9^{nlslacZ}$ heterozygous and homozygous embryos revealed a complete lack of Pdx1 expression in the presumptive dorsal pancreatic epithelium of $Hb9^{nlslacZ}$ mutant embryos, whereas Pdx1 expression in the ventral pancreatic epithelium appeared normal (FIG. 23e,f). By E10.5, distinct dorsal and ventral pancreatic buds were visible in heterozygous embryos (FIG. 23g,h) but no dorsal bud was discernible in homozygous $Hb9^{nlslacZ}$ embryos (FIG. 23g,h). Transverse sections of E10.5 $Hb9^{nlslacZ}$ mutant embryos suggest that the prospective dorsal bud instead remains a part of the developing duodenum (FIG. 23i,j). These results suggest that Hb9 is required for the evagination and subsequent development of the dorsal pancreatic bud.

To analyze the state of differentiation of the presumptive dorsal bud of $Hb9^{nlslacZ}$ homozygous embryos, we examined the expression of early pancreatic markers in E9.5–10.5 mutant embryos. In E9.5 wild-type embryos, Isl1 (FIG. 24a), Nkx2.2 (FIG. 24c) and glucagon (FIG. 24e) were expressed in the dorsal pancreatic epithelium. Mesenchymal expression of Isl1 in $Hb9^{nlslacZ}$ mutant embryos was indistinguishable from that of wild-type littermates (Ahlgren et al. 1997) but we failed to detect Isl-expressing epithelial cells in the dorsal primordium (FIGS. 24a,b). Similarly, Nkx2.2- and glucagon-positive cells were absent from the dorsal pancreatic anlage (FIGS. 24a–f). In contrast, the Hb9 expression, as well as expression of early pancreatic markers, is detected in a normal temporal and spatial manner in the dorsal pancreatic bud of $Pdx1^{-/-}$ (Ahlgren et al. 1996 and data not shown). These results provide evidence that loss of Hb9 function impairs the initial stages in the dorsal pancreatic program, blocking both epithelial evagination and differentiation of early pancreatic cell types. They also show that the arrest in dorsal pancreatic bud development in the $Hb9^{nlslacZ}$ mutant mice is more severe than that observed in $Pdx1^{-/-}$ mice.

The signaling molecule Sonic hedgehog (Shh) has been shown to exert an inhibitory action on pancreatic development (Apquelvist et al. 1997; Hebrok et al. 1998; Kim et al. 1997). We therefore investigated whether the impairment in initiation of dorsal pancreatic development might result from the ectopic expression of Shh or Indian hedgehog (Ihh: Apquelvist et al. 1997; Bitgood et al. 1995) in the presumptive pancreatic epithelium. The expression of both Shh an Ihh was examined in E9.5 homozygous $Hb9^{nlslacZ}$ embryos. Neither the level nor the domain of expression of Shh or Ihh was changed in the pancreatic epithelium of mutant embryos (FIGS. 24q–j). Thus, the block in the specification of the dorsal pancreatic differentiation program in $Hb_9^{nlslacZ}$ mutants appears not to be a result of altered Shh or Ihh expression.

The presence of ventral pancreatic tissue as assessed in E17.5 $Hb9^{nlslacZ}$ homozygous mutants indicates that the early development of the ventral pancreas is independent of Hb9 function. To analyze whether there is a later defect in the development of ventral pancreatic tissue, we examined the expression of the endocrine hormones insulin (Ins; FIGS. 25a–d,g,h), glucagon (Glu; FIGS. 25a,b), somatostatin (Som; FIGS. 25c,d) and the exocrine enzymes amylase (FIGS. 25e,f) and carboxypeptidase A (data not shown). Each of these markers was expressed in the ventral pancreas of $Hb9^{nlslacZ}$ homozygous neonates and the amount and general organization of endocrine cells into islet-like clusters and of exocrine cells into acinar-like structures appeared normal (FIGS. 25a–f). Double immunohistochemical analysis, however, revealed an approximately 20% decrease in the number of Ins-positive cells and an approximately 3-fold increase in the number of $Som^+$-cells (FIG. 25c,). $Ins^+/Isl1^+$ cells make up approximately 68% in wild-type and 53% in $Hb9^{nlslacZ}$ homozygous neonates; $Som^+/Isl^+$ cells make up approximately 9% in wild-type an 25% $Hb9^{nlslacZ}$ homozygous neonates. The number of Glu-positive cells appeared unchanged in Hb9 mutant mice; $Glu^+/Isl1^+$ cells make up approximately 23% in both wild-type and $Hb9^{nlslacZ}$ homozygous neonates (FIGS. 25a,b).

We also noted a defect in the spatial organization of endocrine cells in individual islets. Thus, although islet cell clusters were present in the ventral pancreas of Hb9 mutants, they failed to organize themselves into the typical structure of maturing islets in which α-cells are located at the periphery and surround a core of β-cells (FIGS. 25a–d). The Ins-positive cells present in the ventral pancreas of Hb9 mutants still expressed the transcription factors (Edlund et al. 1998) Pdx1 (FIGS. 25g,h) and Nkx6.1 (data not shown) as well as glucokinase (data not shown). In contrast, the expression of glucose transporter type 2 (Glut2) was virtually undetectable (FIGS. 25i,j). These histological analyses indicate that the ventral pancreatic epithelium generates both exocrine and endocrine cells in the absence of Hb9 function. These results also provide evidence that although the genesis of pancreatic ventrally derived β-cells is independent of Hb9, the terminal differentiation and maturation of β-cells requires Hb9 function.

Our study provides further insight into the molecular events that control the specification of pancreatic cell fate. Our results show that Hb9 is required selectively for specifying the initial stages of dorsal pancreatic development. As a consequence, the dorsal pancreatic bud does not develop in Hb9 mutant mice. In contrast, the ventral pancreatic epithelium develops and generates both exocrine and endocrine cell types, thus revealing an early molecular distinctions between the programs for dorsal and ventral pancreatic development. Nevertheless, the ventral pancreas of Hb9 mutant embryos exhibits a more subtle perturbation in β-cell differentiation and islet cell organization, indicating a later role for Hb9 in the development of pancreatic β-cells.

The development of the pancreas begins with the dorsal and ventral protrusion of a region of the primitive gut epithelium (Wessells et al. 1967; Pictet et al. 1972; Slack et al. 1995; Edlund et al. 1998. Several homeodomain and basic-helix-loop-helix class transcription factors, notably Isl1, Nkx2.2, Pax4, Pax6, and NeuroD/2, have been shown to exert important functions in the control of pancreatic endocrine cell differentiation (Ahlgren et al. 1997; Naya et al. 1997; Sander et al. 1997; Sosa-Pineda et al. 1997; St. Onge et al. 1997; Sussel et al. 1998). These factors are expressed at early stages of pancreas development but in their absence, the initial steps of pancreatic development proceed normally resulting only later in a perturbation of the differentiation of pancreatic endocrine cell types (Slack et al. 1995). The basic-helix-loop-helix class transcription factor p48, in contrast, is required for exocrine but not endocrine differentiation (Krapp et al. 1998).

The homeodomain protein IPF1/PDX1 is required at an earlier stage in pancreatic development. Mice and humans lacking Ipf1/Pdx1 lack a pancreas (Ahlgren et al. 1996; Jonsson et al. 1994; Offield et al. 1996; Stoffers et al. 1997). Ipf1/Pdx1 appears nevertheless to act at a step downstream of the initial specification of the gut endoderm to a pancreatic fate (Ahlgren et al. 1996; Offield et al. 1996) These findings imply the existence of additional genes involved in the regulation of earlier stages of pancreatic development. Thus, despite increasing information on the identity and function of factors involved in pancreatic cell differentiation, the molecular steps that occur prior to the onset of Ipf1/Pdx1 function to specify early stages in the program of pancreatic differentiation are poorly defined. It also remains unclear how the initially separate (Pictet et al. 1972; Slack et al. 1995; Edlund et al. 1998) programs of dorsal and ventral pancreatic bud development are co-ordinated to produce a convergent developmental program. In this paper we report that in mouse embryos the homeobox gene Hb9 (Harrison et al. 1994) is expressed by cells in early developing dorsal and ventral pancreatic buds and later in insulin-producing -cells. Dorsal pancreatic development is blocked in mice lacking Hb9 function, but the ventral pancreas does develop and contains both endocrine and exocrine cells. However, the relative proportions and spatial organisation of the various endocrine cells in the ventral pancreas are perturbed. Thus, the requirement for Hb9 in pancreatic development reveals a molecular distinction in the dorsal and ventral differentiation programs and sequential actions at both early and late stages of pancreatic differentiation.

Results.

HB9 is Expressed in Two Distinct Phases of Pancreatic Development.

The homeobox gene Hb9 was initially isolated from a human B cell library (Harrison et al. 1994) During mouse embryonic development, the expression of HB9 is first evident at the ~8 somite stage (e8) in the notochord, in the entire dorsal gut endoderm and in the ventral endoderm at the prospective pancreatic level (FIG. 22a and data not shown). In contrast, at this stage IPF1/PDX1 is expressed only in the ventral pancreatic endoderm (FIG. 22b). Thus, in the early dorsal pancreatic anlage the initiation of HB9 expression appears to precede that of IPF1/PDX1 expression, whereas in the ventral anlagen HB9 and IPF1/PDX1 are expressed concurrently. By e9.5 the level of expression of HB9 is reduced in both the dorsal and ventral pancreatic buds, and also in the notochord (FIG. 22c and data no shown). By e10.5, only a low level of HB9 expression remains in the dorsal pancreatic bud and virtually no HB9 expression is detected in the ventral bud or in the notochord (FIG. 22e and data not shown). In contrast, expression of IPF1/PDX1 is maintained in both pancreatic buds at these stages (Ohlsson et al. 1993; Ahlgren et al. 1996) (FIGS. 22d,f). Thus, HB9 is expressed transiently at early stages by cells in both the dorsal and ventral buds, and endodermal expression of HB9 is down regulated prior to that of IPF1/PDX1.

At late embryonic stages, however, HB9 expression reappears in the differentiating pancreas. At e17.5, HB9 expression was detected in the insulin producing -cells (FIG. 22*g*) but not in glucagon producing -cells (FIG. 22*h*) or in somatostatin producing -cells (FIG. 22*i*). No expression of HB9 was observed in non-endocrine pancreatic cells (FIG. 22 and data not shown). The -cell specific expression of HB9 persisted in the adult pancreas (data not shown). Together, these results show that HB9 is expressed in two distinct developmental phases, first during the evagination of the pancreatic buds and later in differentiating -cells.

Hb9-deficient Mice Lack a Dorsal Pancreas.

To determine the role of Hb9 in the development of the pancreas we analysed mice in which the Hb9 gene has been inactivated by homologous recombination in ES cells. The -galactosidase gene, placed downstream of an internal ribosome entry site (IRES), was inserted out-of-frame into the first coding exon of HB9 (Arber et al. submitted for publication) HB9nlslacZ heterozygous offspring survived to adulthood, were fertile, and did not exhibit any overt abnormalities. Hb9nlslacZ homozygous mice survived fetal development but died soon after birth, possibly from respiratory failure (Arber et al. submitted for publication). To investigate the state of pancreatic differentiation in mice lacking Hb9 function we initially examined e17.5 Hb9nlslacZ mutant embryos. These embryos exhibited an overtly normal gastrointestinal tract although the duodenum appeared expanded (FIG. 23*a*) Analysis of the pancreas, however, revealed that the dorsal pancreatic epithelial bud was completely absent whereas the ventral bud was present (FIG. 23*a*). The spleen, an organ that develops from the dorsal mesenchyme was present in Hb9 mutants (FIG. 23*a*) and analysis of younger, e13.5 embryos, showed that the mesenchyme that normally surrounds the dorsal pancreas was present and appeared to have developed normally (FIG. 23*b*). Thus, the lack of the dorsal pancreatic bud appears to reflect a selective defect in the specification and development of the presumptive dorsal pancreatic epithelium.

To begin to determine the stage at which the development of the dorsal pancreas is perturbed, we analysed e9.5–10.5 Hb9nlslacZ homozygous embryos by whole-mount detection of lacZ activity. At e9.5, lacZ activity was observed throughout the dorsal endoderm of both heterozygous and homozygous Hb9nlslacZ embryos (FIGS. 23*c,d*). The lacZ-activity observed in the Hb9nlslacZ homozygous embryos provides evidence that the expression of Hb9 is not positively auto-regulated. One potential explanation for the increase in lacZ expression in homozygous mutants is that HB9 negatively controls its own gene expression. Alternatively, the increased lacZ-expression in the homozygous embryos may be due to expression from the additional copy of the lacZ allele. In favour of the former possibility, analysis of Hb9 expression in the spinal cord has revealed that Hb9 gene expression in motor neurons is negatively auto-regulated (Arber et al. submitted for publication).

In homozygous Hb9nlslacZ embryos the evagination of the dorsal pancreatic bud failed to occur (FIGS. 23*c,d*). Analysis of e9.5 Hb9nlslacZ heterozygous and homozygous embryos revealed a complete lack of IPF1/PDX1 expression in the presumptive dorsal pancreatic epithelium of Hb9nlslacZ mutant embryos, whereas IPF1/PDX1 expression in the ventral pancreatic epithelium appeared normal (FIGS. 23*e,f*). By e10.5, distinct dorsal and ventral pancreatic buds were clearly visible in heterozygous embryos (FIGS. 23*g,h*) but no evidence of a dorsal bud was discernible in the homozygous Hb9nlslacZ embryos (FIGS. 23*g,h*). Transverse sections of e10.5 Hb9nlslacZ mutant embryos suggest that the prospective dorsal bud instead remains a part of the developing duodenum (FIGS. 23*i,j*). These results suggest that Hb9 is required for the evagination and subsequent development of the dorsal pancreatic bud.

Hb9 is Required for Initiation of Dorsal Pancreatic Differentiation.

To analyse the state of differentiation of the presumptive dorsal bud of Hb9nlslacZ homozygous embryos we examined the expression of early pancreatic markers in e9.5–10.5 mutant embryos. In e9.5 wild-type embryos, Isl1 (FIG. 24*a*), Nkx2.2 (FIG. 24*c*), and glucagon (FIG. 24*e*) were expressed in the dorsal pancreatic epithelium. Mesenchymal expression of Isl1 in Hb9nlslacZ mutant_embryos was indistinguishable from that of wild type littermates (Ahlgren et al. 1997) but no Isl+ epithelial cells were detected in the dorsal primordium (FIGS. 24*a,b*). Similarly, Nkx2.2+ and glucagon+cells were absent from the dorsal pancreatic anlage (FIGS. 24*c–f*). In contrast, the expression of HB9 as well as that of early pancreatic markers was detected in a normal temporal and spatial manner in the dorsal pancreatic bud of Ipf1/Pdx1 −/− embryos (Spooner et al. 1970 and data not shown). Together, these results provide evidence that loss of Hb9 function impairs the initial stages in the dorsal pancreatic program, thus obstructing both epithelial evagination and differentiation of early pancreatic cell types. They also show that the arrest in dorsal pancreatic bud development in the Hb9nlslacZ deficient mice is more severe than that observed in Ipf1/Pdx1−/− mice.

The signalling molecule, Sonic hedgehog (Shh), has been shown to exert an inhibitory action on pancreatic development 20–22 (Apelqvist et al. 1997; Hebrok et al. 1998; Kim et al. 1997). We therefore investigated whether the impairment in initiation of dorsal pancreatic development might result from the ectopic expression of Shh or Indian Hedgehog (Ihh) (Apelqvist et al. 1997; Bitgood et al. 1995) in the presumptive pancreatic epithelium. The expression of both Shh and Ihh was examined in e9.5 homozygous Hb9nlslacZ embryos. However, the domain of expression of both Shh and Ihh was not expanded into the pancreatic epithelium of Hb9nlslacZ mutant embryos (FIGS. 24*g–j*). Thus, the block in the specification of the dorsal pancreatic differentiation program in Hb9nlslacZ mutants is not due to the de-restriction of Shh or Ihh expression.

The Ventral Pancreas of Hb9-deficient Mice Exhibits Abnormal Islets that Contain Immature -Cells.

The presence of ventral pancreatic tissue as assessed in e17.5 Hb9nlslacZ homozygous mutants_indicates that the early development of the ventral pancreas is independent of Hb9 function. To analyse whether there is a late defect in the development of ventral pancreatic tissue we examined the expression of the endocrine hormones insulin (Ins) (FIGS. 25*a–d,g,h*), glucagon (Glu) (FIGS. 25*a,b*), somatostatin (Som) (FIGS. 25*c,d*), and the exocrine enzymes amylase (FIGS. 25*e,f*) and carboxypeptidase A (data not shown). Each of these markers was expressed in the ventral pancreas of Hb9nlslacZ homozygous neonates and the amount and general organisation of endocrine cells into islet-like clusters and of exocrine cells into acinar-like structures appeared normal (FIGS. 25*a–f*). However, double immunohistochemical analysis revealed a ~20% decrease in the number of Ins+-cells (Ins+/Isl1+ cells=~68% in wild-types and ~53% in Hb9nlslacZ homozygous neonates), and a ~3-fold increase in the number of Som+-cells (Som+/Isl+ cells=~9% in wild-types and ~25% in Hb9nlslacZ homozygous neonates) (FIGS. 25c,d). The number of Glu+-cells appeared unchanged in the Hb9 mutant mice (Glu+/Isl1+ cells ~23% in both wild-types and Hb9nlslacZ homozygous neonates) (FIGS. 25a,b).

We also noted a defect in the spatial organisation of endocrine cells within individual islets. Thus, although islet cell clusters were present in the ventral pancreas of Hb9 mutants they failed to organise themselves into the typical structure of maturing islets in which -cells are located at the periphery and surrounds a core of -cells (FIGS. 25a–d). The Ins+-cells present in the ventral pancreas of Hb9 mutant mice still expressed the transcription factors (Edlund et al. 1998) IPF1/PDX1 (FIGS. 25g,h) and Nkx6.1 (data not shown), as well as glucokinase (data not shown). In contrast the expression of glucose transporter type 2 (Glut2) was virtually undetectable (FIG. 25i,j). Together, these histological analyses indicate that the ventral pancreatic epithelium generates both exocrine and endocrine cells in the absence of Hb9 function. These results also provide evidence that although genesis of pancreatic ventrally derived -cells is independent of Hb9, the terminal differentiation and maturation of -cells requires Hb9 function.

Discussion.

The present study provides further insight into the molecular events that control the specification of pancreatic cell fate. Our results show that Hb9 is required selectively for specifying the initial stages of dorsal pancreatic development and as a consequence the dorsal pancreatic bud does not develop in Hb9 mutant mice. In contrast, the ventral pancreatic epithelium develops and generates both exocrine and endocrine cell-types, thus revealing an early molecular distinction between the programs of dorsal and ventral pancreatic development. Nevertheless, the ventral pancreas of Hb9 mutant embryos exhibits a subtle perturbation in -cell differentiation and islet cell organisation, thus suggesting a later role for Hb9 in the development of pancreatic -cells.

The early stages of dorsal and ventr 1 pancreatic development display several other distinguishing characteristics other than the dorsal dependence on Hb9. First, the organisation and identity of surrounding mesenchyme and other mesodermal tissues differ at dorsal and ventral pancreatic buds (Wessells et al. 1967; Pictet et al. 1972; Ahlgren et al. 1997; Spooner et al. 1970). Second, pancreatic endocrine cells appear earlier in the dorsal than in the ventral bud and third, the generation of dorsal, but not ventral, pancreatic mesenchyme is dependent on Isl1 (Ahlgren et al. 1997). The demonstration of a selective dorsoventral difference in the dependence on HB9 activity thus adds to the evidence that the programs of pancreatic differentiation dorsally and ventrally are initially distinct. How does HB9 control the initial specification of the dorsal pancreatic program? Our results are suggestive of three general possibilities that relate to differences in the timing of HB9 and IPF1/PDX1 expression dorsally and ventrally, to the expression of a redundant activity ventrally, and to a function of Hb9 independent of its expression in the gut endoderm.

The first possibility that is consistent with our data invokes a function for Hb9 in providing the dorsal gut epithelium with the competence to respond to signals that initiate the pancreatic differentiation program, most critically the expression of IPF1/PDX1. In this view Ipf1/Pdx1, once expressed, may be sufficient for the later progression of pancreatic development, obviating the requirement for Hb9 function. The relative timing of onset of Hb9 and Ipf1/Pdx1 expression in the dorsal and ventral pancreatic buds may therefore be a critical factor in the selectivity of the mutant phenotype. Consistent with this model, our results show that IPF1/PDX1 is expressed at an earlier stage ventrally than dorsally. A second possibility is that the function of Hb9 ventrally is compensated for by a factor with a similar activity. The chick MNR2 homeobox gene is closely related to Hb9 and has been shown to have an overlapping function with the Hb9 gene in spinal cord development (Tanabe et al. 1998). Although, a mouse MNR2 gene has not yet been identified, the existence of such an activity could compensate ventrally for the loss of Hb9 function.

A third possibility is that dependence of dorsal pancreatic differentiation on Hb9 does not in fact reflect a function intrinsic to the gut epithelium. Hb9 is transiently expressed by notochord cells from ~e8 to e10. It is therefore possible that Hb9 acts to control dorsal pancreatic specification by regulating the expression of inductive or repressive factors secreted from the notochord. The analysis of Shh and Ihh expression in Hb9nlslacZ homozygous embryos suggests, however, that Hb9 is not involved in establishing the zone of exclusion of Shh or Ihh expression in the presumptive dorsal pancreatic region since the expression of both these genes is restricted normally in Hb9 mutant embryos. Nevertheless, the activation or repression of other genes required for pancreatic development could normally be controlled by signals from the notochord that are missing in Hb9 deficient mice. The notochord appears, however, structurally normal in the Hb9 mutant mice, the floorplate and motorneurons are generated, and both the notochord and floorplate display normal Shh expression (Arber et al. submitted for publication and data not shown). These observations suggest that many of the inducing properties of the notochord are intact in the Hb9nlslacZ homozygous mice. Thus, dorsal pancreatic development: seems to be dependent both on the expression of Hb9 and on the exclusion of hh gene expression.

The specification of the ventral pancreatic differentiation program is independent of Hb9 function and hence a ventral pancreas develops with both exocrine and endocrine cell types. Nevertheless, as judged from the lack of Glut2 expression in Ins+-cells present in the ventral pancreas of Hb9 mutant mice, Hb9 seem to be required for terminal differentiation and/or maturation of -cells. The decreased number of Ins+-cells together with the increase in the number of Som+-cells provides evidence that the establishment of these two cell-types may be coupled and that Hb9 promotes the -cell fate on expense of Som+ -cells. Interestingly, the development of both—and -cells requires Pax4 (Sosa-Pineda et al. 1997). Thus, in the pancreas of Pax4 mutant mice there is a loss of both Ins+- and Som+-cells whereas the number of Glu+-cells increases 14 (Sosa-Pineda et al. 1997). This suggests that the -and -cells originate from a common, Pax4-dependent progenitor cell and that Hb9 might function at a later stage to promote the -cell fate and characteristics. The late, ventral phenotype therefore suggests a role for Hb9 in ensuring proper terminal differentiation of pancreatic -cells in a manner reminiscent of the role proposed for Hb9 in motor neuron differentiation (Arber et al. submitted for publication).

Genetic studies in mice have shown that several transcription factors have important roles for pancreatic development and/or glucose homeostasis (Slack et al. 1995). Many of these genes have been linked to human diabetic or pancreatic syndromes, thus demonstrating a conservation in the function of genes that control pancreatic development in mice and humans (Edlund et al. 1998) In humans as in mice, homozygosity for mutations in the human Ipf1gene results in complete pancreas agenesis (Ahlgren et al. 1996; Jonsson et al. 1994; Offield et al. 1996; Stoffers et al. 1997). Maturity Onset Diabetes of the Young (MODY) 4 has been linked to heterozygosity for mutations in the human Ipf1 gene (Stoffers et al. 1997) and similarly, mice heterozygous for deletions in the Ipf1/Pdx1 gene have impaired glucose tolerance (Ahlgren et al. 1998; Dutta et al. 1998). The human Hb9 gene, HLXB9, has been linked to dominant inherited forms of sacral agenesis. (Ross et al. 1998). No pancreatic or diabetic complications have yet been reporter in these patients but spontaneous forms of this syndrome, are known to occur in infants of type1 diabetic mothers (Ross et al. 1998; Kalter et al. 1993). These observations raise the possibility that expression or function of Hb9 might be sensitive to elevated glucose levels in a manner similar to that reported for Ipf1/Pdx1 (Sharma et al. 1995; Matsuoka et al. 1997; Olson et al. 1998). The apparent immature status of the -cells in the ventral pancreas of Hb9 mutant mice also suggests that impaired Hb9 function, or expression, may turn out to be associated with development of diabetes. Whether mutations in HLXB9 are also associated with human dorsal pancreatic agenesis syndromes (Wildling et al. 1993) remains to be determined.

Methods:

Animals: The generation of Hb9nlslacZ mice has been described elsewhere (Arber et al. submitted for publication) and mutant mice were obtained from our local breeding colony. Mice and embryos were genotyped as described elsewhere (Arber et al. submitted for publication).

In situ hybridization and immunohistochemistry. In situ hybridization using a rat Shh (Arber et al. submitted for publication) and a mouse Ihh probe, (Kim et al. 1997) kindly provided by A. P. McMahon, was carried out as described (Ahlgren et al. 1996). Immunohistochemistry was performed as previously described (Ahlgren et al. 1996). The following primary antibodies were used and diluted as indicated: guinea pig anti-glucagon (Linco) 1:1000, guinea pig anti-insulin (DAKO) 1:10000, mouse anti-HB9, (Tanabe et al. 1998) rabbit anti-HB9 (Arber et al. submitted for publication), 1:10 and 1:200 respectively, rabbit anti-human -amylase (Sigma) 1:4000, rabbit anti-Nkx2.2 (Briscoe et al. manuscript in preparation), 1:2000, rabbit anti-Isl1 (Ahlgren et al. 1997), 1:250, rabbit anti-IPF1/PDX-1 (Ohlsson et al. 1993), 1:400, rat anti-somatostatin antibodies (Bender MedSystems) 1:1000, rabbit anti Glut2 (Ahlgren et al. 1998) (Inst. of Pharm. & Tox., Lausanne, Switzerland), 1:200. When mou e anti-HB9 antibody was used, the blocking step was performed using a Mouse to Mouse kit (ScyTek). When double staining was carried out, a second blocking step using swine anti-rabbit IgG (DAKO) diluted 1:20 was included. The secondary antibodies used were diluted as follows: biotinylated anti-mouse (Jackson) 1:200, biotinylated anti-rat (Vector) 1:200, fluorescein anti-guinea pig (Jackson) 1:200, and Cy3 anti-rabbit (Jackson) 1:200. Streptavidin-FITC (Jackson) 1:2.00 was applied to detect biotinylated secondary antibodies. The numbers of Ins-, Glu and Som-positive cells (n=800–1500 cells from 3 different wild-type and mutant mice respectively) were counted using anti Isl-1 antibodies (Ahlgren et al. 1997) as a marker for endocrine cells.

Whole-mount X-gal staining.

Fixed Hb9nlslacZ heterozygous and homozygous embryos were washed in 0.1 M PB (pH 7.4), 2 mM MgCl2, 5 mM EGTA, permeabilized in 0.1 M PB (pH 7.4), 2 mM MgCl2, 0.01% sodium desoxycholate, 0.02% NP40 and X-gal (Saveen) stained for 3 hours or overnight at 37C. Embryos were post-fixed in 4% paraformaldehyde in PBS (pH 7.4) at 4C for 30 minutes before being dehydrated successively from PBS (pH 7.4) to 100% methanol and cleared in 1:2 benzyl alcohol:benzyl benzoate for photography. Later they were rehydrated and incubated overnight at 4C in 30% sucrose in PBS (pH 7.4) before being embedded in Tissue-Tek (Sakura) for cryostat sectioning.

REFERENCES

Wessells, N. K. &. Cohen, J. H. Early pancreas organogenesis: morphogenesis, tissue interactions and mass effects. *Dev. Biology.* 15, 237–270 (1967).

Ohlsson, H., Karlsson, K. & Edlund, T. IPF1, a homeodomain-containing transactivator of the insulin gene. *EMBO J.* 12, 4251–4259 (1993).

Ahlgren, U., Jonsson, J. & Edlund, H. The morphogenesis of the pancreatic mesenchyme is uncoupled from that of the pancreatic epithelium in PDX1/IPF1-deficient mice. *Development* 122, 1409–1416 (1996).

Jonsson, J., Carlsson, L., Edlund, T. & Edlund, H. Insulin-promoter-factor 1 is required for pancreas development in mice. *Nature* 371, 606–609 (1994).

Offield, M. F. et al. PDX-1 is required for pancreatic outgrowth and differentiation of the rostral duodenum. *Development* 122, 983–995 (1996).

Harrison, K. A., Druey, K. M., Deguchi, Y., Tuscano, J. M. & Kerhl, J. H. A novel human homeobox gene distantly related to proboscipedia is expressed in lymphoid and pancreatic tissues. *J. Biol. Chem.* 269, 19968–19975 (1994).

Ross, A. J. et al. A homeobox gene, HLXB9, is the major locus for dominantly inherited sacral agenesis. *Nature Genet.* 20, 358–361 (1998).

Pictet, R., & Rutter, W. J. Development of the embryonic endocrine pancreas. In *Handbook of Physiology*, (ed. D. F. Steiner, and N. Frenkel), pp. 25–66. Williams and Wilkins, Washinton DC (1972).

Slack, J. M. W. Developmental biology of the pancreas. *Development* 121, 1569–1580 (1995).

Edlund, H. Transcribing pancreas. *Diabetes* 47, 1817–1823 (1998).

Ahlgren, U., Pfaff, S., Jessel, T. M., Edlund, T. & Edlund, H. Independent requirement for ISL1 in the formation of the pancreatic mesenchyme and islet cells. *Nature* 385, 257–260 (1997).

Naya, F. J. et al. Diabetes, defective pancreatic morphogenesis, and abnormal enteroendocrine differentiation in BETA2/neuroD-deficient mice. *Genes & Dev.* 11, 2323–2334 (1997).

Sander M. et al. Genetic analysis reveals that PAX6 is required for normal transcription of pancreatic hormone genes and islet development. *Genes Dev.* 11, 1662–1673 (1997).

Sosa-Pineda, B., Chowdhury, K., Torres, M., Oliver, G., & Gruss, P. The Pax4 gene is essential for differentiation of insulin-producing beta cells in the mammalian pancreas. *Nature* 386, 399–402 (1997).

St-Onge, L., Sosa-Pineda, B., Chowdhury, K., Mansouri, A. & Gruss, P. Pax6 is required for differentiation of glucagon-producing alpha-cells in mouse pancreas. *Nature* 387, 406–409 (1997).

Sussel, L. et al. Mice lacking the homeodomain transcription factor Nkx2.2 have diabetes due to arrested differentiation of pancreatic beta cells. *Development* 19, 2213–2221 (1998).

Krapp, A. et al. The bHLH protein PTF1-p48 is essential for the formation of the exocrine and the correct spatial organization of the endocrine pancreas. *Genes & Dev.* 12, 3752–3763 (1998).

Stoffers, D. A., Zinkin, N. T., Stanojevic, V., Clarke, W. L. & Habener, J. F. Pancreatic agenesis attributable to a single nucleotide deletion in the human IPF1 gene coding sequence. *Nature Genet.* 15, 106–110 (1997).

Arber, S. et al. Requirement for the homeobox gene Hb9 in the establishment of motor neuron subtype identity. Submitted for publication.

Apelqvist, A., Ahlgren, U. & Edlund, H. Sonic hedgehog directs specialised mesoderm differentiation in the intestine and pancreas. *Current Biology* 7, 801–804 (1997).

Hebrok, M., Kim, S. K. & Melton, D. A. Notochord repression of endodermal sonic hedgehog permits pancreas development. *Genes & Dev.* 12, 1705–1713 (1998).

Kim, S. K., Hebrok, M. & Melton, D. A. Notochord to endoderm signalling is required for pancreas development. *Development* 124, 4243–4252 (1997).

Bitgood, M. J. & McMahon, A. P. Hedgehog and Bmp genes are coexpressed at many diverse sites of cell-cell interaction in the mouse embryo. *Dev. Biol.* 172, 126–138 (1995).

Spooner, B. S., Walther, B. T. & Rutter, W. J. The development of the dorsal and ventral mammalian pancreas in vivo and in vitro. *J. Cell Biol.* 47, 235–246 (1970).

Tanabe, Y., William, C. & Jessell, T. M. Specification of motor neuron identity by the MNR2 homeodomain protein. *Cell* 95, 67–80 (1998).

Stoffers, D. A., Ferrer, J., Clarke, W. L. & Habener, J. F. Early-onset type-II diabetes mellitus (MODY4) linked to IPF1. *Nature Genet.* 17, 138–139 (1997).

Ahlgren, U., Jonsson, J., Jonsson, L., Simu, K. & Edlund, H. -cell specific inactivation of the mouse Ipf1/Pdx1 gene results in impaired glucose transporter expression and late onset diabetes. *Genes & Dev.* 12, 1763–1768 (1998).

Dutta, S., Bonner-Weir, S., Montminy, M., & Wright, C. Regulatory factor linked to late-onset diabetes? *Nature* 392, 560 (1998).

Kalter, H Case reports of malformations associated with maternal diabetes: history and critique. *Clin. Genet.* 43, 174–179 (1993).

Sharma. A., Olson, L. K., Robertson, R. P. & Stein, R. The reduction of insulin gene transcription in HIT-T15 beta cells chronically exposed to high glucose concentration is associated with the loss of RIPE3b1 and STF-1 transcription factor expression. *Mol. Endocrinol* 9, 1127–1134 (1995).

Matsuoka, T. et al. Glycation-dependent, reactive oxygen species-mediated suppression of the insulin gene promoter activity in HIT cells. *J. Clin. Invest.* 99, 144–150 (1997).

Olson, L. K., Qian, J. & Poitout, V. Glucose rapidly and reversibly decreases INS-1 cell insulin gene transcription via decrements in STF-1 and C1 activator transcription factor activity. *Mol. Endocrinol* 12, 207–219 (1998).

Wildling, R. et al. Agenesis of the dorsal pancreas in a woman with diabetes mellitus and in both her sons. *Gastroenterology* 104, 1182–1186 (1993).

What is claimed is:

1. An isolated protein comprising consecutive amino acids having the amino acid sequence set forth in SEQ ID NO: 1.

2. An isolated protein comprising consecutive amino acids having the amino acid sequence set forth in SEQ ID NO:1 which encodes a homeobox motor neuron restricted pattern protein designated MNR2.

3. The protein of claim 2, wherein the protein is a vertebrate protein.

4. The protein of claim 3, wherein the protein is a chick protein.

5. A pharmaceutical composition comprising the protein of claim 2 and a pharmaceutically acceptable carrier.

* * * * *